(12) United States Patent
Shiner et al.

(10) Patent No.: US 12,376,885 B2
(45) Date of Patent: *Aug. 5, 2025

(54) EXTERNAL FIXATOR ASSEMBLY

(71) Applicant: GLOBUS MEDICAL, INC., Audubon, PA (US)

(72) Inventors: Zachary C. Shiner, Philadelphia, PA (US); David R. Jansen, Glenmoore, PA (US); Sergio Muniz, Philadelphia, PA (US); David Laird, Brandamore, PA (US); Barclay Davis, Glenmoore, PA (US)

(73) Assignee: Globus Medical, Inc., Audubon, PA (US)

( * ) Notice: Subject to any disclaimer, the term of this patent is extended or adjusted under 35 U.S.C. 154(b) by 214 days.

This patent is subject to a terminal disclaimer.

(21) Appl. No.: 18/193,112

(22) Filed: Mar. 30, 2023

(65) Prior Publication Data

US 2023/0233231 A1 Jul. 27, 2023

Related U.S. Application Data

(63) Continuation of application No. 16/735,752, filed on Jan. 7, 2020, now Pat. No. 11,672,566, which is a continuation of application No. 15/862,713, filed on Jan. 5, 2018, now Pat. No. 10,682,160, which is a continuation-in-part of application No. 15/473,891, filed on Mar. 30, 2017, now Pat. No. 10,070,890, which is a continuation-in-part of application No. 15/455,317, filed on Mar. 10, 2017, now Pat. No.
(Continued)

(51) Int. Cl.
*A61B 17/64* (2006.01)

(52) U.S. Cl.
CPC .......... *A61B 17/64* (2013.01); *A61B 17/6416* (2013.01); *A61B 17/645* (2013.01); *A61B 17/6466* (2013.01); *A61B 17/6483* (2013.01); *A61B 17/6425* (2013.01); *A61B 17/6441* (2013.01)

(58) Field of Classification Search
CPC ... A61B 17/64; A61B 17/6416; A61B 17/645; A61B 17/6466; A61B 17/6483; A61B 17/6425; A61B 17/6441
USPC ................................ 606/54, 57, 58, 59, 277
See application file for complete search history.

(56) References Cited

U.S. PATENT DOCUMENTS

| 4,135,505 A * | 1/1979 | Day ................... A61B 17/6466 403/177 |
| 4,244,360 A | 1/1981 | Dohogne |

(Continued)

FOREIGN PATENT DOCUMENTS

| CN | 201168944 Y | 12/2008 |
| JP | 2006-055647 A | 3/2006 |

(Continued)

*Primary Examiner* — Eduardo C Robert
*Assistant Examiner* — David C Comstock

(57) ABSTRACT

External fixator assemblies, systems, and methods thereof. An external fixator system may include a plurality of fixator assemblies configured to connect a plurality of pins, for example, positioned on opposite sides of a fractured bone, with one more rods. The fixator assemblies may include a plurality of clamp assemblies that are configured to clamp onto the rods. A distractor/compression instrument is used to adjust the location of a clamp assembly along the length of its rod.

17 Claims, 55 Drawing Sheets

Related U.S. Application Data 10,136,919, which is a continuation-in-part of application No. 15/151,843, filed on May 11, 2016, now Pat. No. 9,943,337, which is a continuation-in-part of application No. 14/958,961, filed on Dec. 4, 2015, now Pat. No. 9,539,029, which is a continuation of application No. 14/957,793, filed on Dec. 3, 2015, now Pat. No. 9,872,707.

(56) References Cited

U.S. PATENT DOCUMENTS

| | | |
|---|---|---|
| 4,299,520 A | 11/1981 | Iwata |
| 4,548,199 A | 10/1985 | Agee |
| 4,600,000 A | 7/1986 | Edwards |
| 4,600,344 A | 7/1986 | Sutenbach et al. |
| 4,628,919 A | 12/1986 | Clyburn |
| 4,684,284 A | 8/1987 | Bradley, Jr. |
| 4,828,444 A | 5/1989 | Oshida |
| 4,978,350 A | 12/1990 | Wagenknecht |
| 4,990,044 A | 2/1991 | Kimak |
| 5,591,164 A | 1/1997 | Nazre et al. |
| 5,630,815 A | 5/1997 | Pohl et al. |
| 5,662,650 A | 9/1997 | Bailey et al. |
| 5,752,954 A | 5/1998 | Mata et al. |
| 5,770,255 A | 6/1998 | Burrell et al. |
| 5,906,464 A | 5/1999 | Wedenig |
| 6,022,348 A * | 2/2000 | Spitzer ............... A61B 17/6466 606/53 |
| 6,080,153 A | 6/2000 | Mata et al. |
| 6,565,564 B2 | 5/2003 | Hoffman et al. |
| 6,663,634 B2 | 12/2003 | Ahrens et al. |
| 6,702,814 B2 | 3/2004 | Walulik et al. |
| 6,942,664 B1 | 9/2005 | Voor et al. |
| 7,004,943 B2 | 2/2006 | Ferrante et al. |
| 7,041,103 B2 | 5/2006 | Hoffmann-Clair et al. |
| 7,048,735 B2 * | 5/2006 | Ferrante ............... A61B 90/57 606/59 |
| 7,179,038 B2 | 2/2007 | Reindl |
| 7,291,148 B2 * | 11/2007 | Agee ............... A61B 17/6425 606/54 |
| 7,338,242 B2 | 3/2008 | Ellis et al. |
| 7,491,008 B2 | 2/2009 | Thomke et al. |
| 7,527,626 B2 | 5/2009 | Lutz et al. |
| 7,608,074 B2 | 10/2009 | Austin et al. |
| 7,618,417 B2 | 11/2009 | Thomke et al. |
| 7,699,848 B2 | 4/2010 | Hoffman et al. |
| 7,717,916 B2 | 5/2010 | Hajianpour |
| 7,722,609 B2 | 5/2010 | Bordeaux |
| 7,758,582 B2 | 7/2010 | Ferrante et al. |
| 7,806,623 B2 | 10/2010 | Thomke et al. |
| 7,875,030 B2 | 1/2011 | Hoffman-Clair et al. |
| 8,029,505 B2 | 10/2011 | Hearn et al. |
| 8,057,473 B2 | 11/2011 | Orsak et al. |
| 8,070,785 B2 | 12/2011 | Biscup |
| 8,100,971 B2 | 1/2012 | Trieu |
| 8,123,747 B2 | 2/2012 | Hajianpour |
| 8,147,490 B2 | 4/2012 | Bauer |
| 8,231,318 B2 | 7/2012 | Pitsch et al. |
| 8,372,073 B2 | 2/2013 | Hoffman et al. |
| 8,382,804 B2 | 2/2013 | Thomke et al. |
| 8,403,928 B2 | 3/2013 | Bordeaux |
| 8,523,858 B2 | 9/2013 | Lessig et al. |
| 8,540,713 B2 | 9/2013 | Zandona et al. |
| 8,585,702 B2 | 11/2013 | Orsak et al. |
| 8,628,530 B2 | 1/2014 | Hajianpour |
| 8,657,819 B2 | 2/2014 | Murner et al. |
| 8,685,023 B2 | 4/2014 | Dorawa et al. |
| 8,808,289 B2 | 8/2014 | Busch et al. |
| 8,827,997 B2 | 9/2014 | Cremer et al. |
| 8,945,129 B2 | 2/2015 | Dominik et al. |
| 8,998,902 B2 | 4/2015 | Hoffman et al. |
| 9,050,135 B2 | 6/2015 | Dominik et al. |
| 9,066,757 B2 | 6/2015 | Tan et al. |
| 9,084,632 B2 | 7/2015 | Orsak et al. |
| 9,155,562 B2 | 10/2015 | Cremer et al. |
| 9,273,715 B2 | 3/2016 | Bordeaux |
| 9,301,782 B2 | 4/2016 | Myers et al. |
| 9,539,029 B1 | 1/2017 | Muniz et al. |
| 11,672,566 B2 * | 6/2023 | Shiner ............... A61B 17/6466 606/59 |
| 2002/0077629 A1 | 6/2002 | Hoffman et al. |
| 2005/0245939 A1 | 11/2005 | Ferrante et al. |
| 2006/0039750 A1 | 2/2006 | Thomke et al. |
| 2006/0255521 A1 | 11/2006 | Brunner et al. |
| 2009/0088751 A1 | 4/2009 | Mullaney |
| 2009/0297294 A1 | 12/2009 | Li et al. |
| 2009/0299368 A1 | 12/2009 | Bauer |
| 2010/0262143 A1 | 10/2010 | Bordeaux |
| 2011/0066151 A1 | 3/2011 | Muerner et al. |
| 2012/0089142 A1 | 4/2012 | Mullaney et al. |
| 2012/0209264 A1 | 8/2012 | Zandona et al. |
| 2013/0144289 A1 | 6/2013 | Dorawa |
| 2014/0018803 A1 | 1/2014 | Lessig et al. |
| 2014/0336649 A1 | 11/2014 | Dorawa et al. |
| 2014/0350558 A1 | 11/2014 | Triplett et al. |
| 2014/0364853 A1 | 12/2014 | Mullaney et al. |
| 2015/0204635 A1 | 7/2015 | Blish |
| 2015/0209081 A1 | 7/2015 | Venturini |
| 2015/0320446 A1 | 11/2015 | Cremer et al. |
| 2016/0038184 A1 | 2/2016 | Erickson |
| 2016/0199098 A1 | 7/2016 | Slagle |
| 2016/0199099 A1 | 7/2016 | Myers et al. |
| 2016/0367291 A1 | 12/2016 | Erickson et al. |
| 2017/0156757 A1 | 6/2017 | Muniz et al. |

FOREIGN PATENT DOCUMENTS

| | | |
|---|---|---|
| JP | 2008539012 A | 11/2008 |
| JP | 2010-540112 A | 12/2010 |
| JP | 2014512854 A | 5/2014 |
| JP | 2014521383 A | 8/2014 |
| JP | 2018008029 A | 1/2018 |
| WO | 9959490 A1 | 11/1999 |
| WO | 2005085658 A1 | 9/2005 |
| WO | 2016035053 A1 | 3/2016 |

* cited by examiner

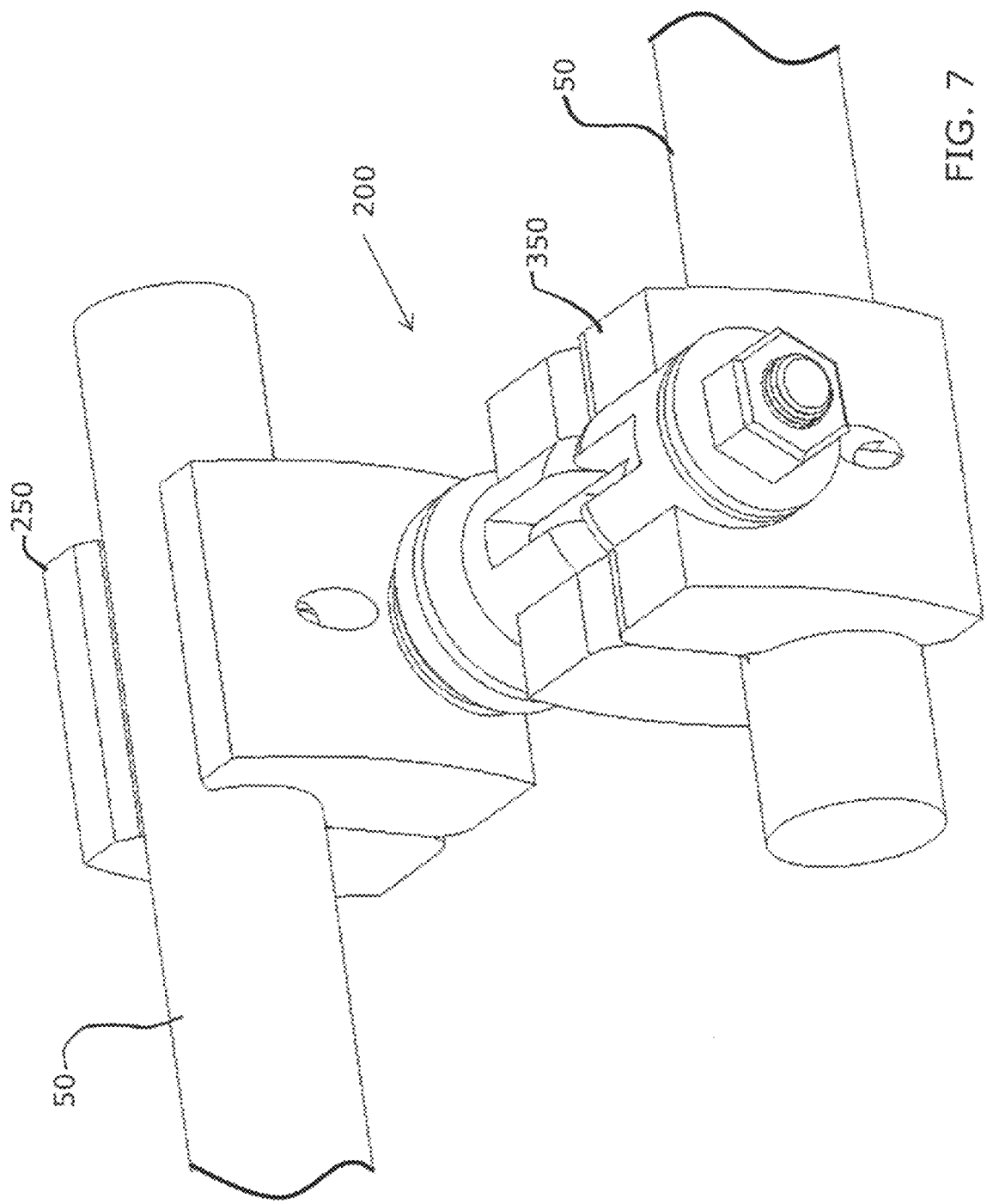

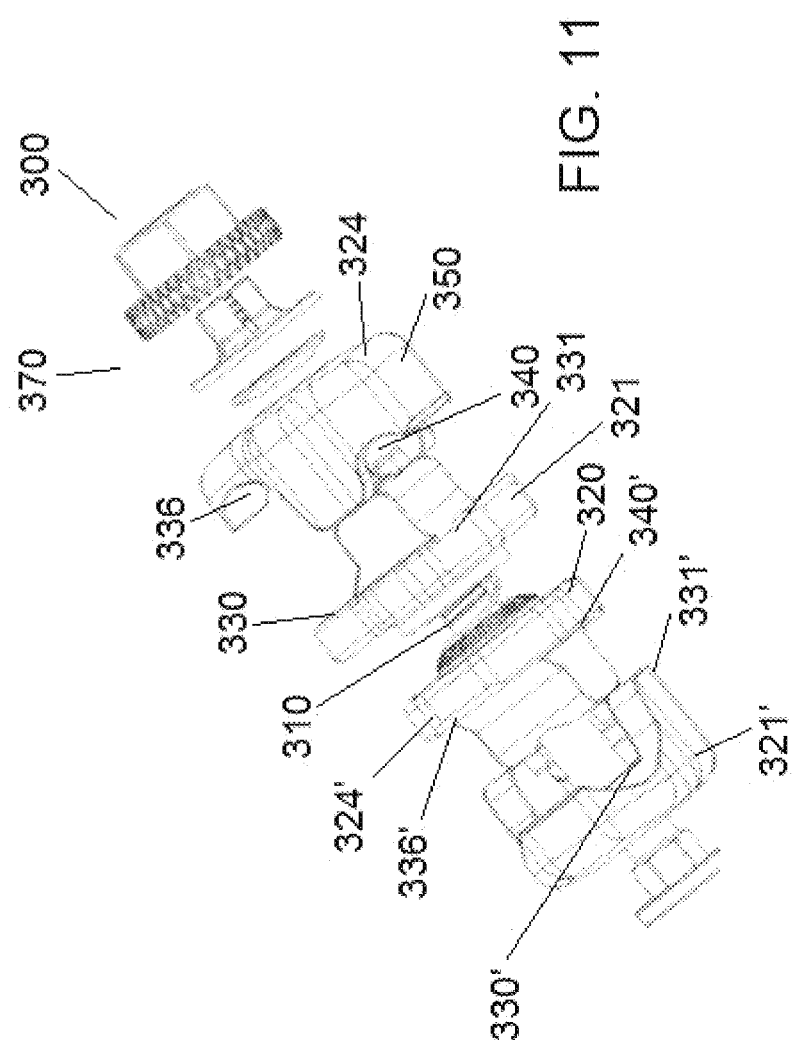

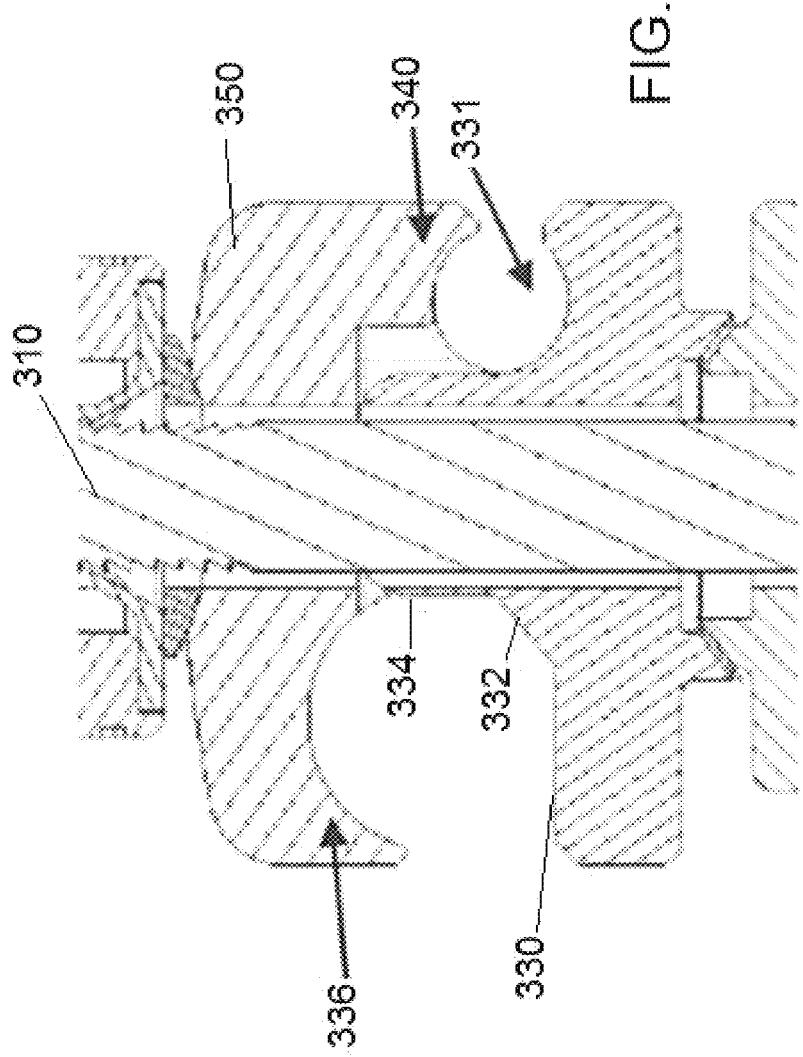

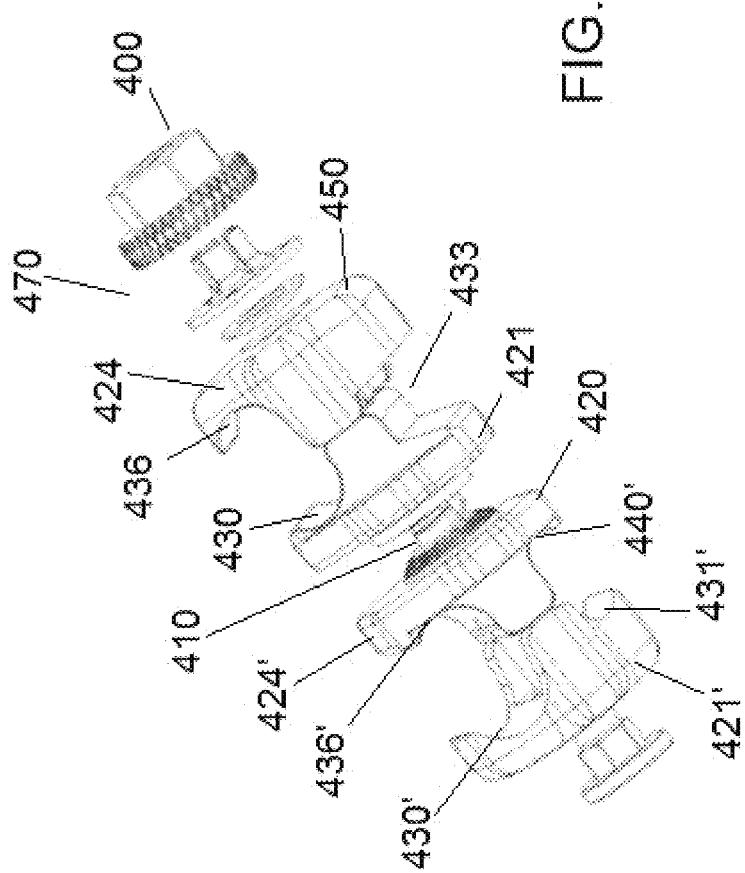

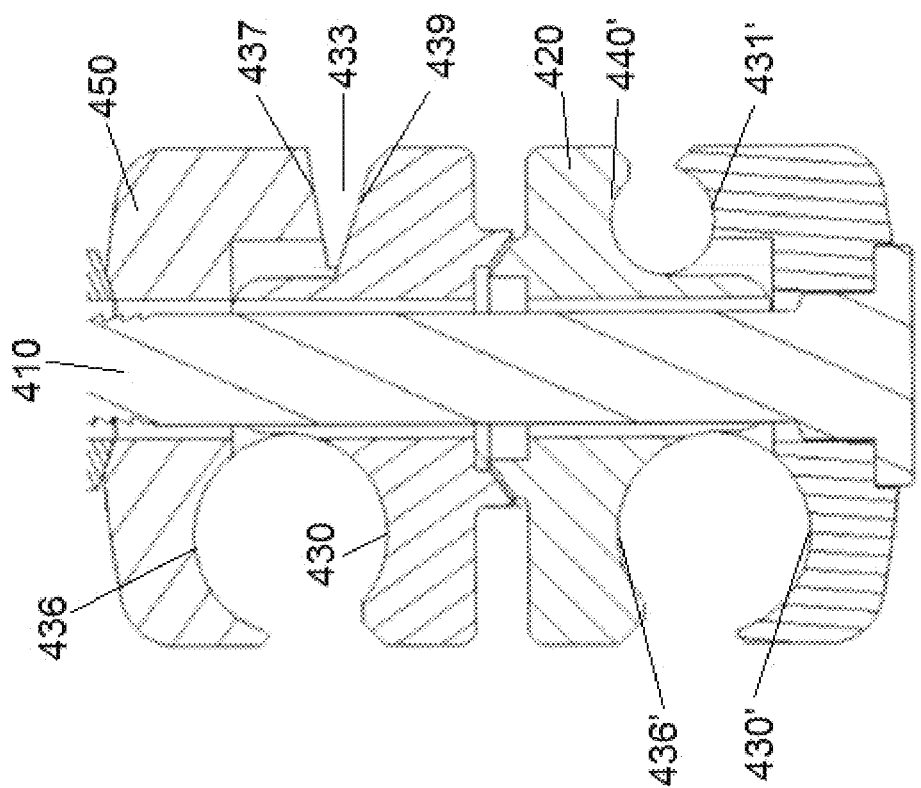

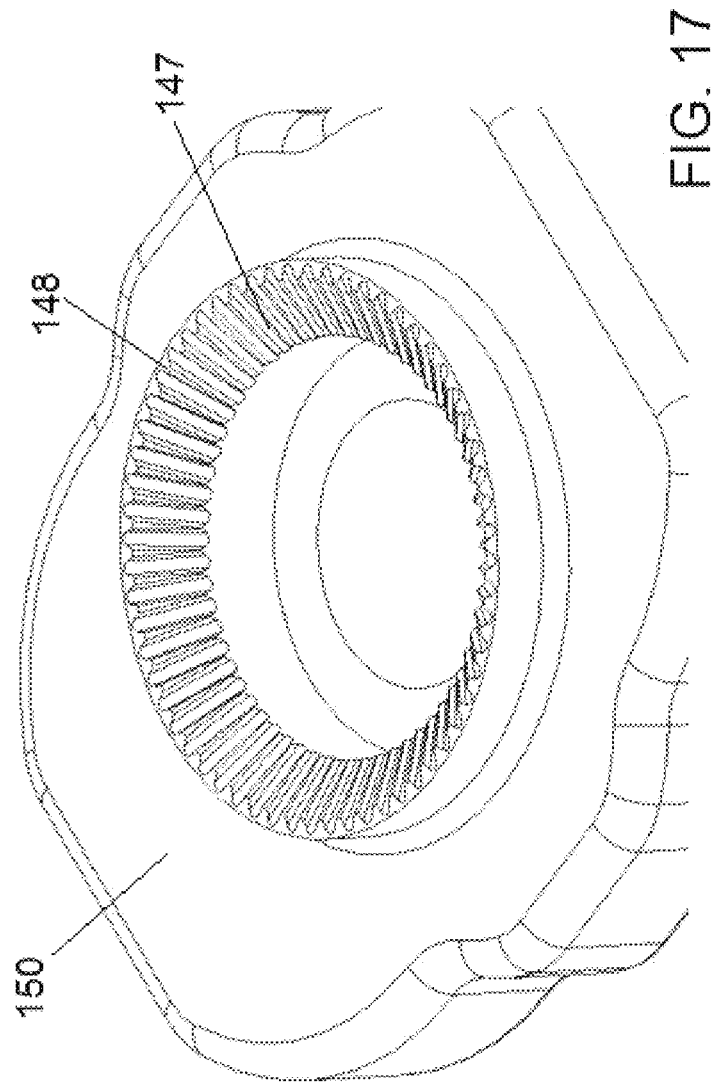

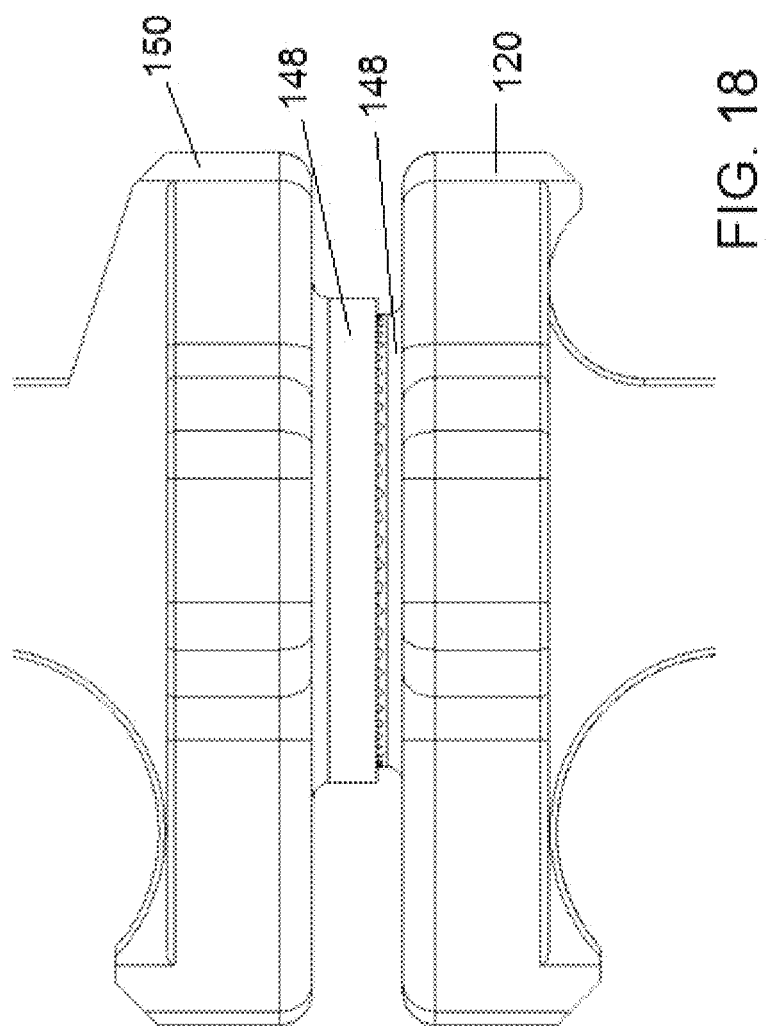

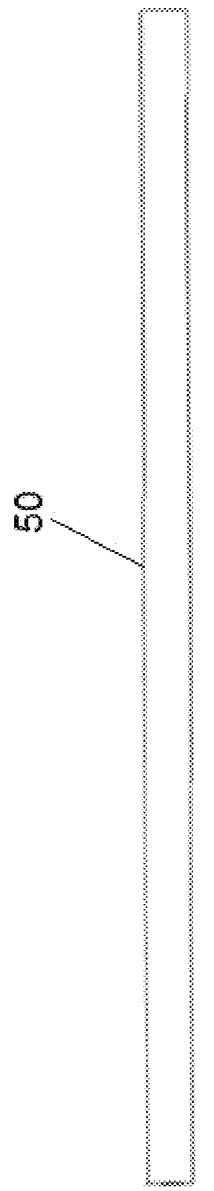

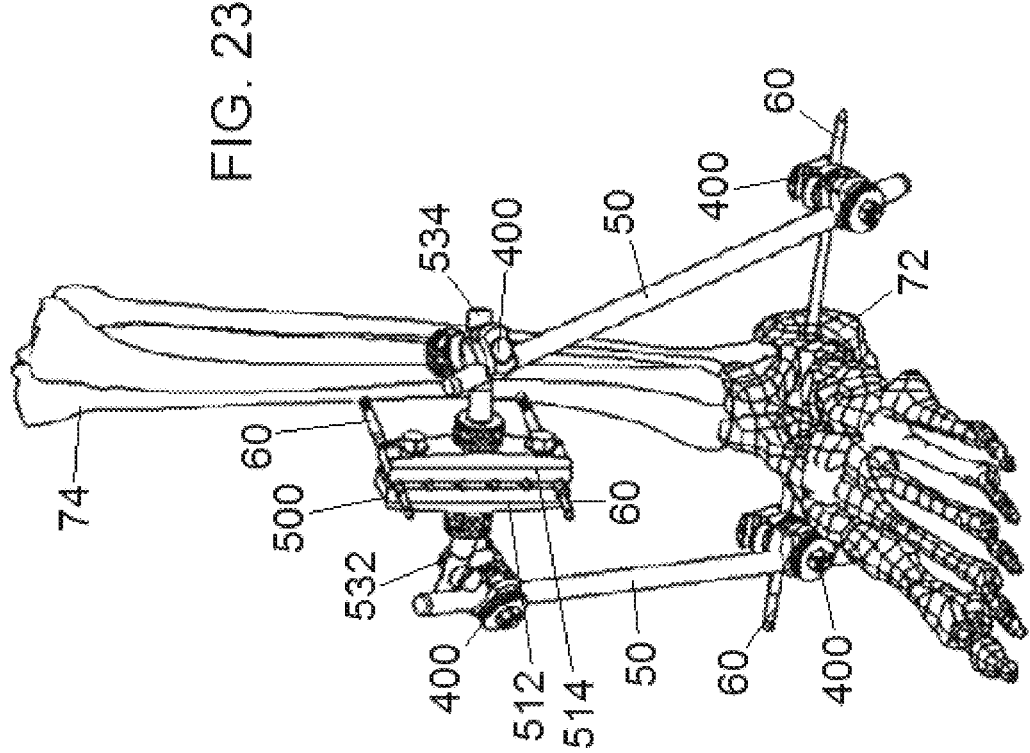

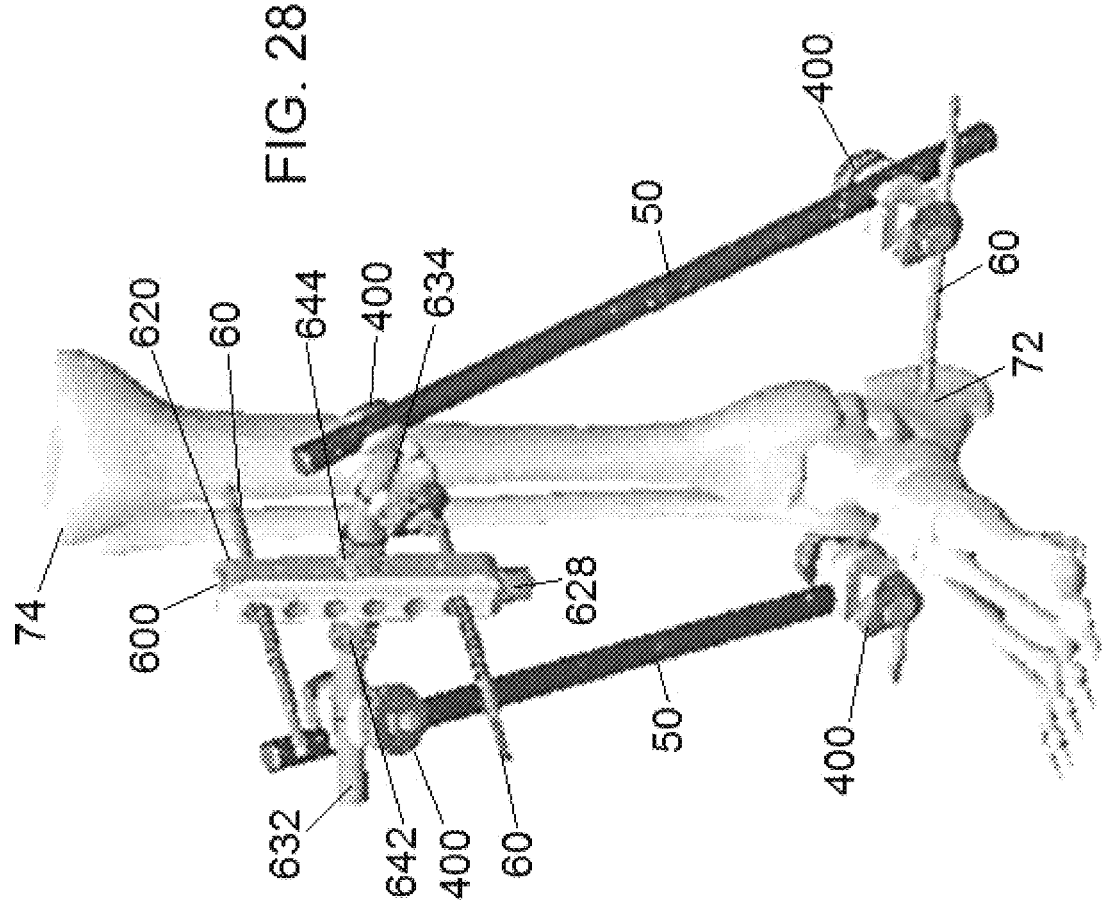

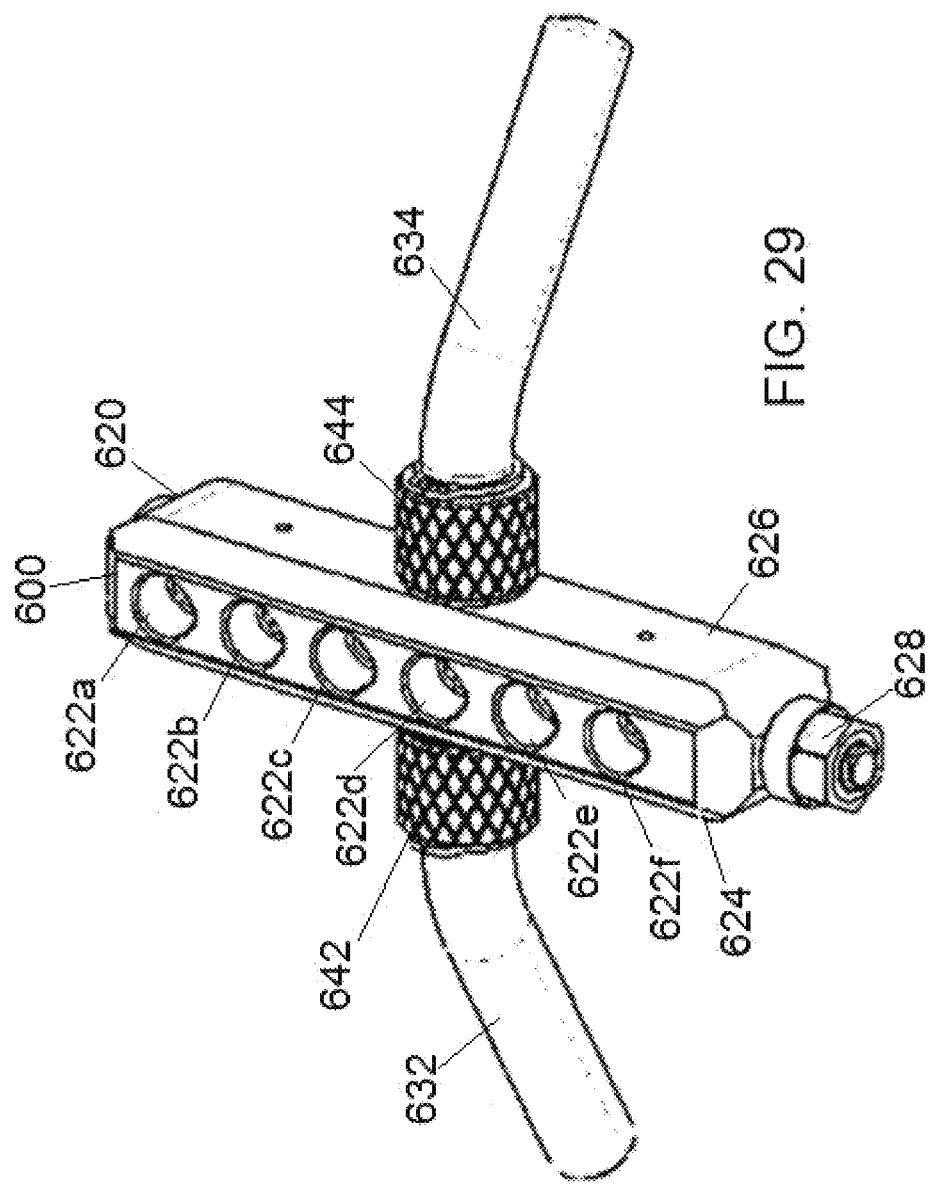

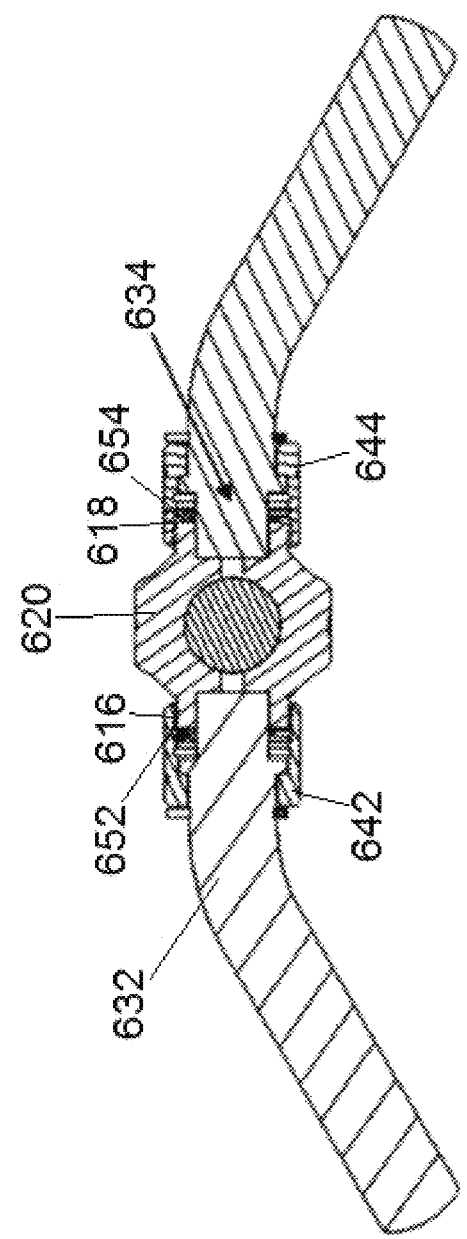

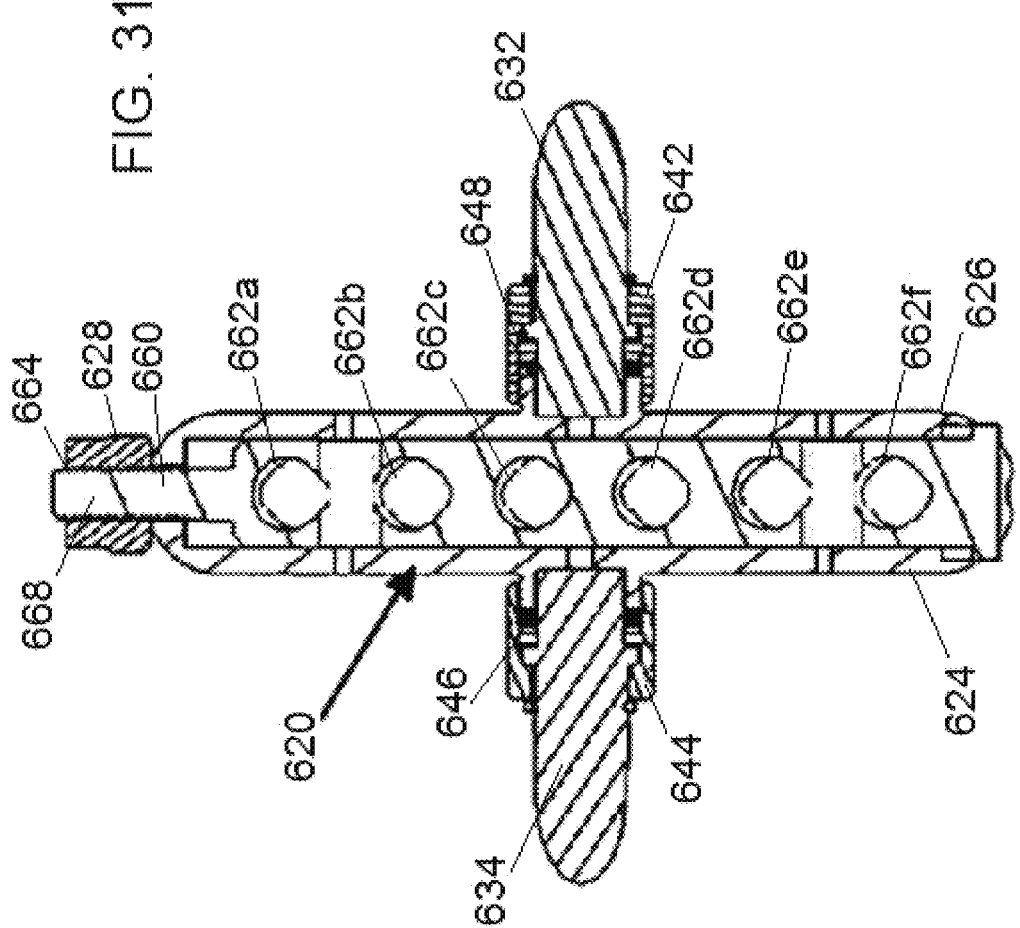

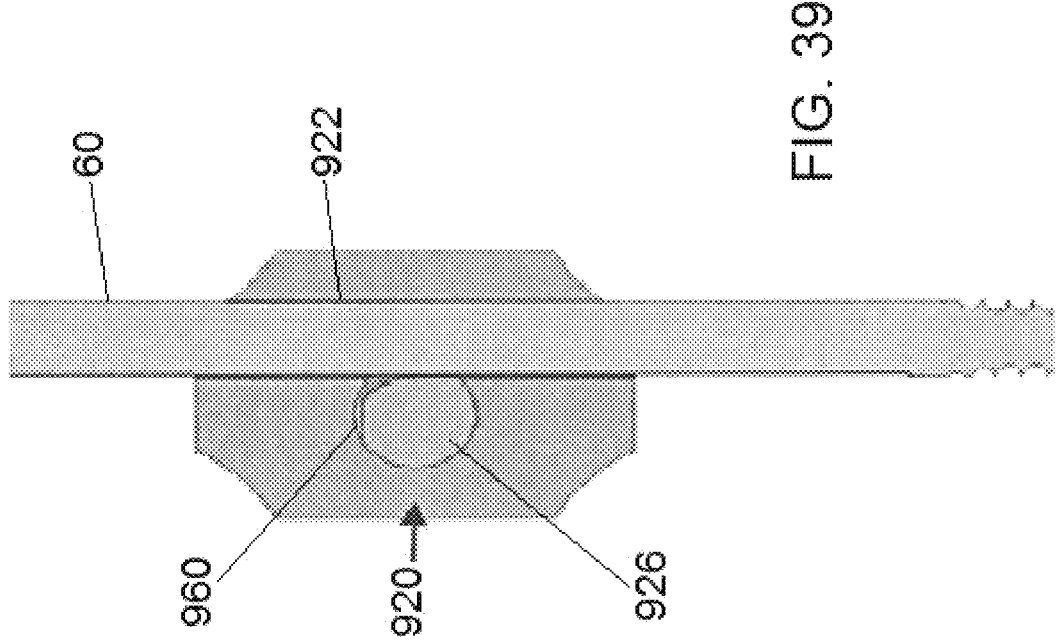

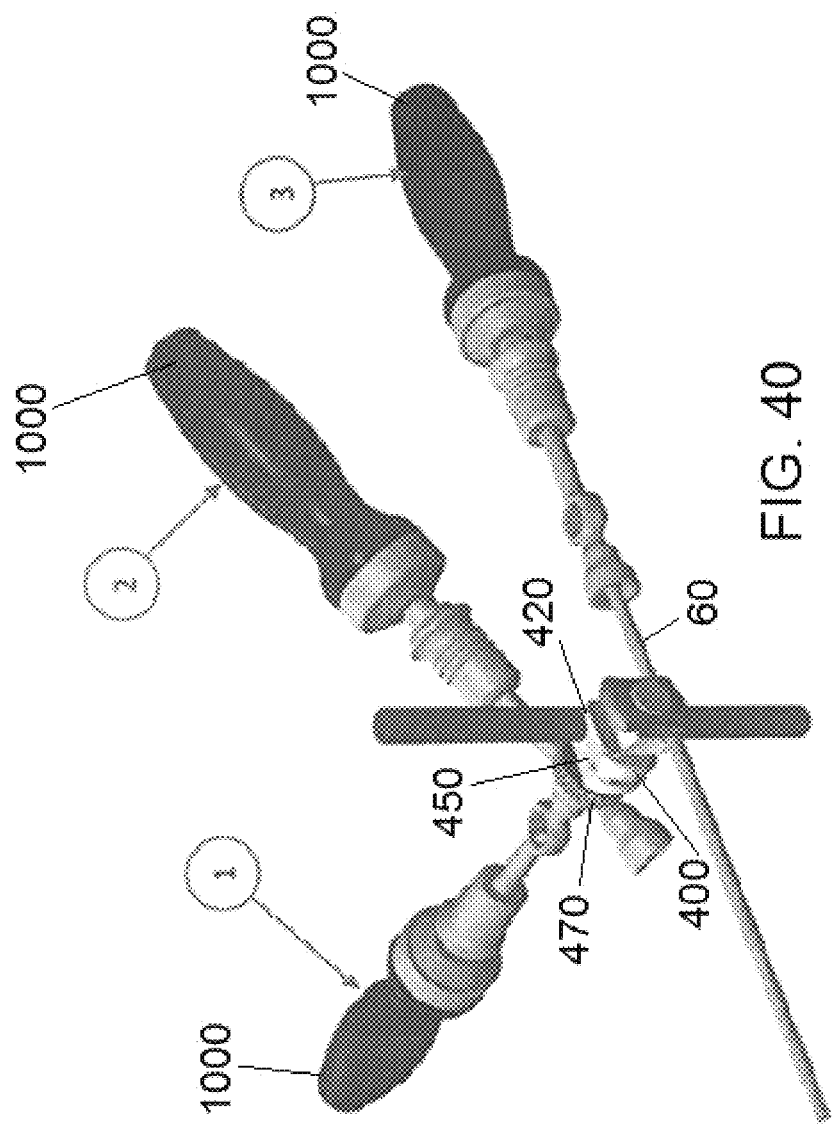

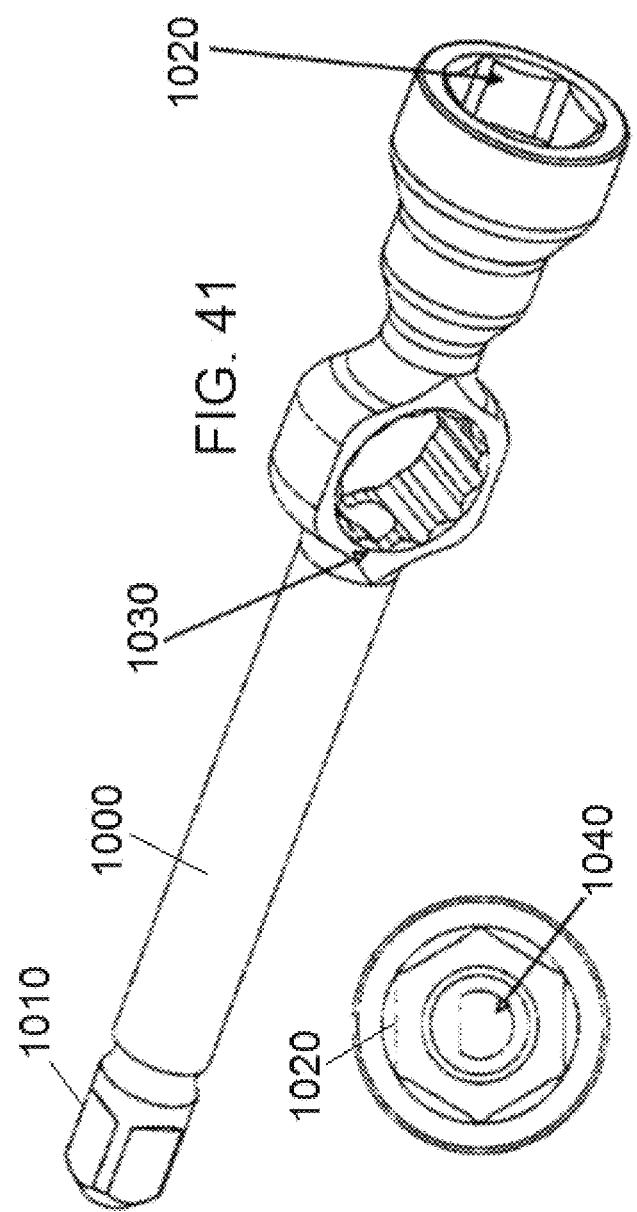

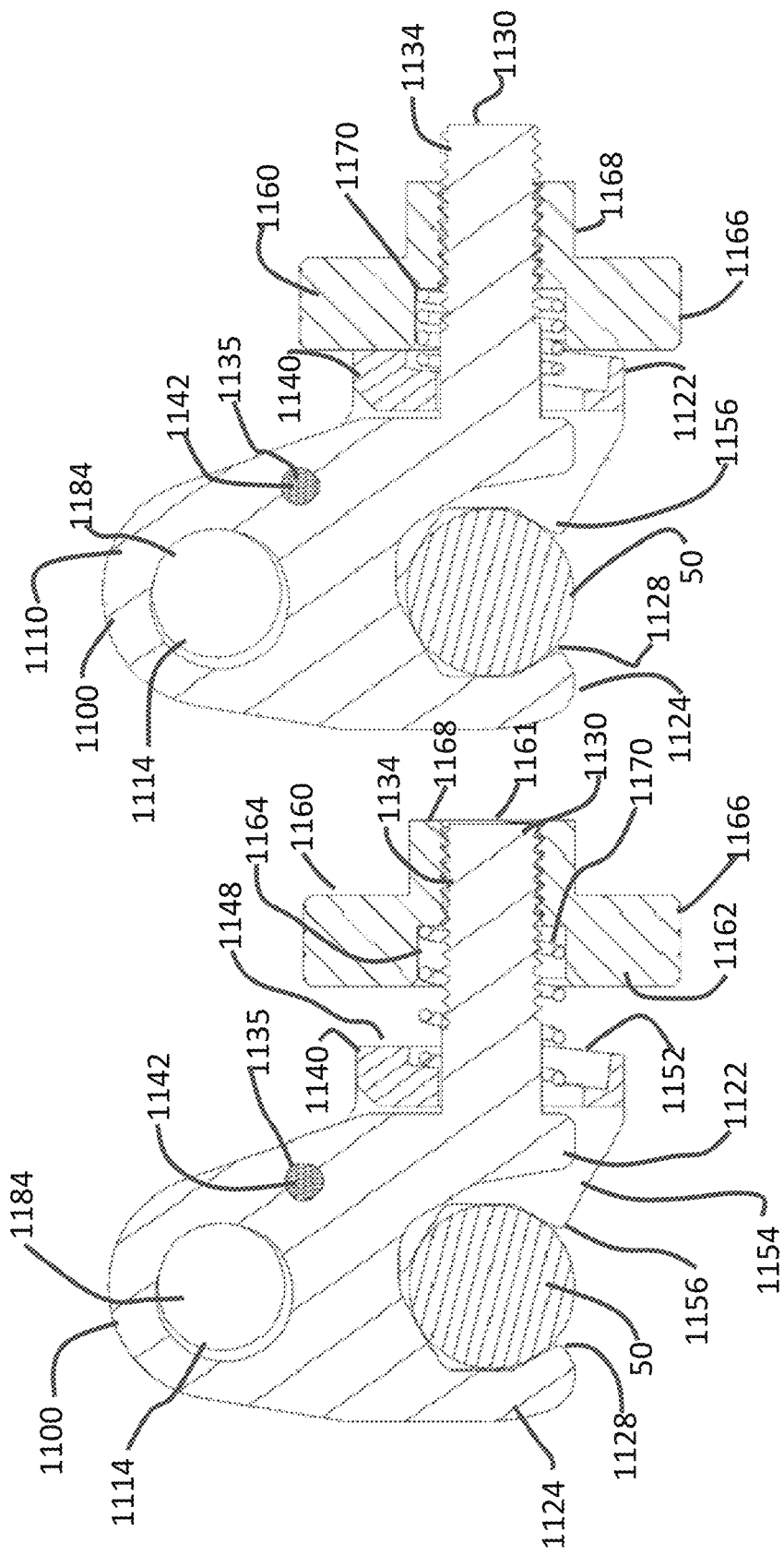

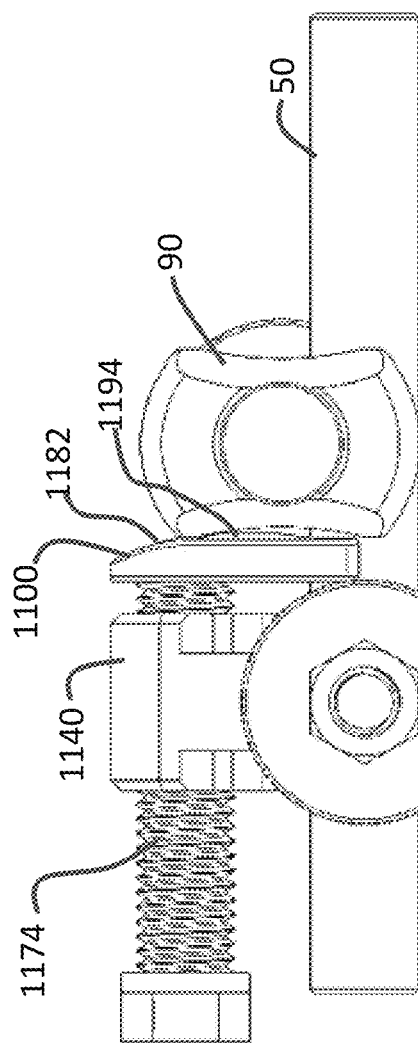
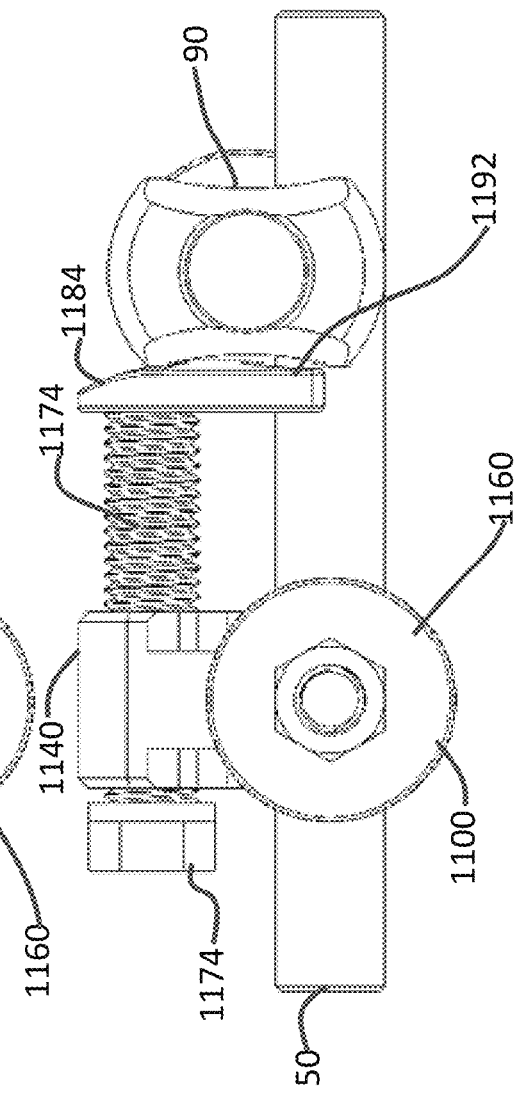

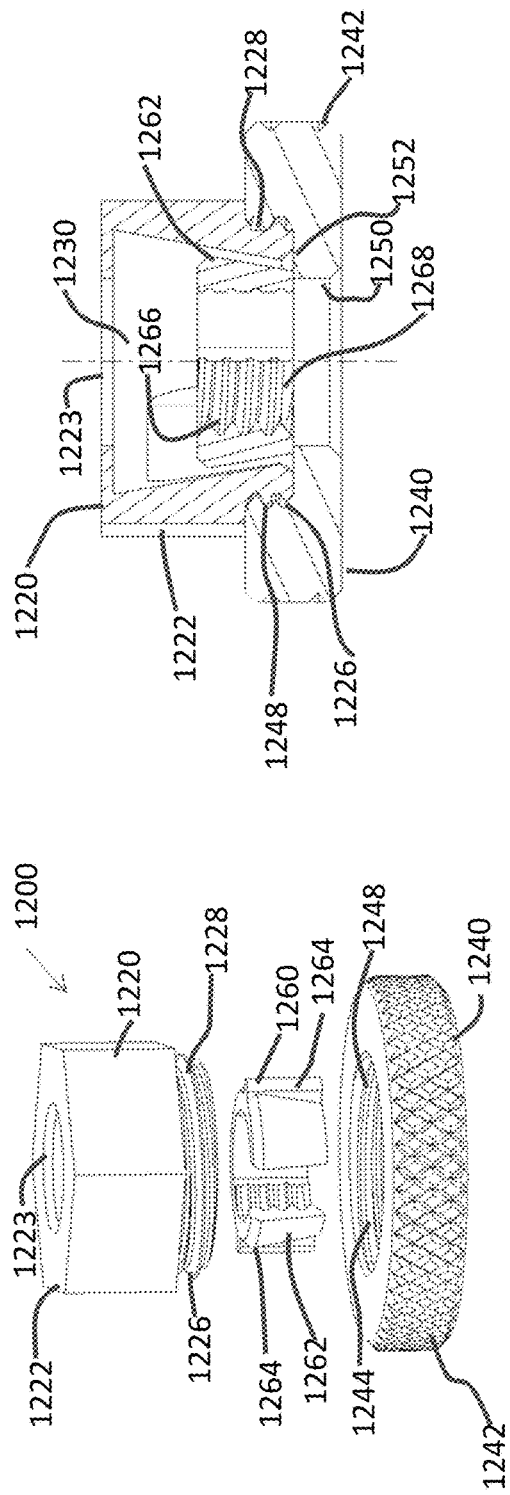
FIG. 53
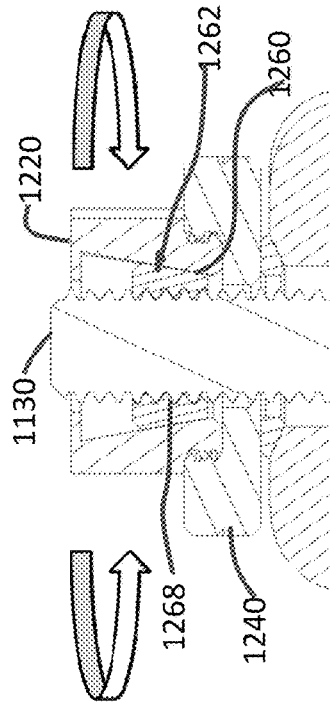
FIG. 54
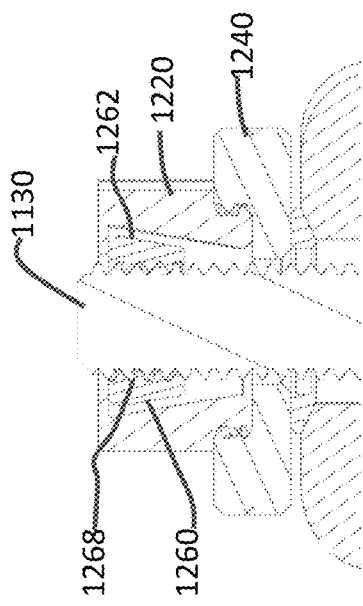
FIG. 55
FIG. 56

EXTERNAL FIXATOR ASSEMBLY

REFERENCE TO RELATED APPLICATIONS

The present application is a continuation application of U.S. Ser. No. 16/735,752, filed Jan. 7, 2020 (published as U.S. Pat. Pub. No. 2020-0138479), which is a continuation application of U.S. Ser. No. 15/862,713, filed Jan. 5, 2018, now U.S. Pat. No. 10,682,160, which is a continuation-in-part application of U.S. Ser. No. 15/473,891, filed Mar. 30, 2017, now U.S. Pat. No. 10,070,890, which is a continuation-in-part application of U.S. Ser. No. 15/455,317, filed on Mar. 10, 2017, now U.S. Pat. No. 10,136,919, which is a continuation-in-part application of U.S. Ser. No. 15/151,843, filed on May 11, 2016, now U.S. Pat. No. 9,943,337, which is a continuation-in-part application of U.S. Ser. No. 14/958,961, filed on Dec. 4, 2015, now issued as U.S. Pat. No. 9,539,029, which is a continuation application of U.S. Ser. No. 14/957,793, filed Dec. 3, 2015, now U.S. Pat. No. 9,872,707, which are each incorporated herein by reference in their entireties for all purposes.

BACKGROUND

Field of the Invention

The present invention relates to external fixator assemblies, and, in particular, to external fixator assemblies having a plurality of clamps.

Description of the Related Art

External fixators have long been used in trauma incidents as a long-term care solution for reducing fractures and promoting bone healing. Recently, however, external fixators have been used for poly-traumatic patients as a way to stabilize fractures until a more definitive method of fixation can be determined and applied. The use of current external fixators to perform this temporary stabilization can be bulky and time-consuming.

Accordingly, there exists a need for lightweight, quick-assembly external fixators.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

According to one embodiment, an external fixator system may include a plurality of external fixator assemblies configured to connect a plurality of pins, for example, positioned on opposite sides of a fractured bone, with one more rods. The fixator assemblies may include a plurality of clamp assemblies which are configured to rotate relative to one another when the fixator assembly is in an unlocked position. Once the relative positioning of the pins and/or rods is achieved, for example, to stabilize the bone or bones, the fixator assemblies may be moved to a locked position, such that the clamp assemblies are fixed in position and no longer able to rotate relative to one another.

In one embodiment, the external fixator assembly includes a shaft having a distal end and a proximal end. The proximal end has at least one external thread. A plurality of clamp assemblies extends along the shaft from the distal end to the proximal end. A biasing member is disposed between adjacent of the plurality of clamp assemblies. A cap assembly is disposed over the proximal end of the shaft. The cap assembly is adapted to bias the plurality of clamp assemblies toward the distal end of the shaft.

In an alternative embodiment, the external fixator assembly includes a shaft comprising a distal end having a flange and a proximal end having at least one external thread. A clamp assembly is disposed along the shaft, proximal of the distal flange. A ratchet assembly biases the clamp assembly toward the distal flange. The ratchet assembly comprises a ratcheting buttress having a radially extending buttress flange and a hole extending through the flange. The hole is sized to allow the shaft to extend therethrough. A plurality of fingers extends proximally around the hole. Each of the plurality fingers has a plurality of internal ratchet teeth adapted to engage the least one external thread on the proximal end on the shaft. A ratchet housing has a distal end having a radially extending housing flange adapted to engage the buttress flange and a proximal end having at least one internal thread adapted to threadably engage the at least one external thread on the shaft.

In still another alternative embodiment, the external fixator assembly includes a ratchet assembly. The ratchet assembly comprises a ratcheting buttress and a ratchet housing. The ratcheting flange having an annular flange having a buttress axial hole formed therein, a tang extending outwardly from the annular flange in a first direction, and a plurality of fingers extending outwardly from the annular flange in the first direction. The plurality of fingers surrounds the hole. Each of the plurality fingers includes a plurality of internal ratchet teeth. The ratchet housing has an annular flange having a housing axial hole formed therein and a body attached to the flange. The annular flange has an external contoured surface, a first radially extending cavity adapted to receive the annular flange of the wrenching buttress, and an axially extending slot adapted to receive the tang. The body has a plurality of external flat surfaces extending around an outer perimeter thereof, a second radially extending cavity adapted to receive the plurality of fingers, and an internally threaded passage adjacent to the second radially extending cavity.

In yet another alternative embodiment, the external fixator assembly comprises a first shaft having a first coupling end and a first free end, a second shaft having a second coupling end and a second free end, and a coupling pivotally retaining the first coupling end and the second coupling end. A first clamp assembly is disposed on the first shaft between the coupling and the first free end. The first clamp assembly comprises a first inner clamp member disposed proximate to the coupling. The first inner clamp member has a first inner slot. A first outer clamp member is disposed proximate to the first free end. The first outer clamp member has a first outer slot. A first biasing member is disposed in the first inner slot and the first outer slot such that first biasing member biases the first inner clamp member toward the first outer clamp member. A second clamp assembly is disposed on the second shaft between the coupling and the second free end. The second clamp assembly comprises a second inner clamp member disposed proximate to the coupling. The second in the clamp member has a second inner slot. A second outer clamp is disposed proximate to the second free end. The second outer clamp member has a second outer slot. A second biasing member is disposed in the second inner slot and the second outer slot such that the second biasing member biases the second inner clamp member toward the second outer clamp member.

In still another embodiment, a distractor/compression instrument comprises a frame having a superior portion having a through-passage extending therethrough, the through-passage having a first end and a second end; and an inferior portion having a stud extending transverse relative to the through-passage. A jaw is pivotally connected to the frame. The jaw has a through-opening sized such that the stud extends through the through-opening. A distraction bolt has a hollow end portion. The distraction bolt extends through the through-opening from the first end. A foot plate is located at the second end of the through-passage. The foot plate has an insert extending into the hollow end portion.

In yet another embodiment, a distractor/compression instrument comprises a generally U-shaped frame having a first leg having a stud extending therefrom away from the first leg, a second leg, and a connector portion having the through-passage extending therethrough, transverse to the stud. A jaw is pivotally connected to the frame between the first leg and the connector portion. The jaw has an engagement face. A securing device is mounted on the stud and has a securing face adapted for engagement with the engagement face. A distraction bolt has a hollow end portion. The distraction bolt extends through the through-opening. A foot plate has an insert extending into the hollow end portion.

In still another embodiment, a method of advancing a member along a rod construct comprises securing the member to the rod construct; inserting the rod construct into the rod passage of the distractor/compression instrument as described above such that the foot plate engages the member; advancing the securing device toward the first leg such that the jaw engages the rod construct; and advancing the distraction bolt through the through-opening and urging the foot plate against the member such that the member slides along the rod construct.

BRIEF DESCRIPTION OF THE DRAWINGS

Other aspects, features, and advantages of the present invention will become more fully apparent from the following detailed description, the appended claims, and the accompanying drawings in which like reference numerals identify similar or identical elements.

FIG. 7 is a perspective view of the external fixator assembly shown in FIG. 6 with rods connected thereto;

FIG. 11 is a top perspective view of an external fixator assembly according to a third exemplary embodiment being used to fixate adjacent bones;

FIG. 12 is a close-up view of a clamp assembly of the external fixator assembly of FIG. 11;

FIG. 13 is a top perspective view of an external fixator assembly according to a fourth exemplary embodiment being used to fixate adjacent bones;

FIG. 14 is a close-up view of a pair of clamp assemblies of the external fixator assembly of FIG. 13;

FIG. 17 is a close-up view of teeth of a toothed locking half in accordance with some embodiments;

FIG. 18 is a close-up view of a first clamp assembly and a second clamp assembly in a fully tightened construct in accordance with some embodiments;

FIG. 19 is a side view of a rod in accordance with some embodiments; and

FIG. 23 is a perspective view of a multi-pin clamp in use.

FIG. 28 is a perspective view of an alternative multi-pin clamp in use.

FIG. 29 is a top perspective view of an alternative multi-pin clamp having an internal sliding member in accordance with some embodiments.

FIG. 30 is a top cross-sectional view of the multi-pin clamp of FIG. 29.

FIG. 31 is a front cross-sectional view of the multi-pin clamp of FIG. 29.

FIG. 39 is a top cross-sectional view of the multi-pin clamp of FIG. 38 including cam in accordance with some embodiments.

FIG. 40 shows a multi-purpose instrument performing three different functions in accordance with some embodiments FIG. 41 is a top perspective view of a multi-purpose instrument in accordance with some embodiments.

FIG. 42 is a front view of the multi-purpose instrument of FIG. 41.

FIG. 46 is a sectional view of the instrument of FIG. 45 in an unlocked position.

FIG. 47 is a sectional view of the instrument of FIG. 45 in a locked position.

FIG. 48 is a side elevational view of the instrument of FIG. 45 installed on a rod construct having a connecting member.

FIG. 49 is a side elevational view of the instrument and construct of FIG. 48, with the connecting member having been moved by the instrument.

FIG. 53 is an exploded perspective view of an exemplary embodiment of a nut assembly.

FIG. 54 is a side elevational view, in section, of the nut assembly of FIG. 53.

FIG. 55 is a side elevational view, in section of the nut assembly of FIG. 53 initially mounted on a stud.

FIG. 56 is a side elevational view, in section of the nut assembly of FIG. 54 having been secured to the stud.

DETAILED DESCRIPTION

Figure 1:
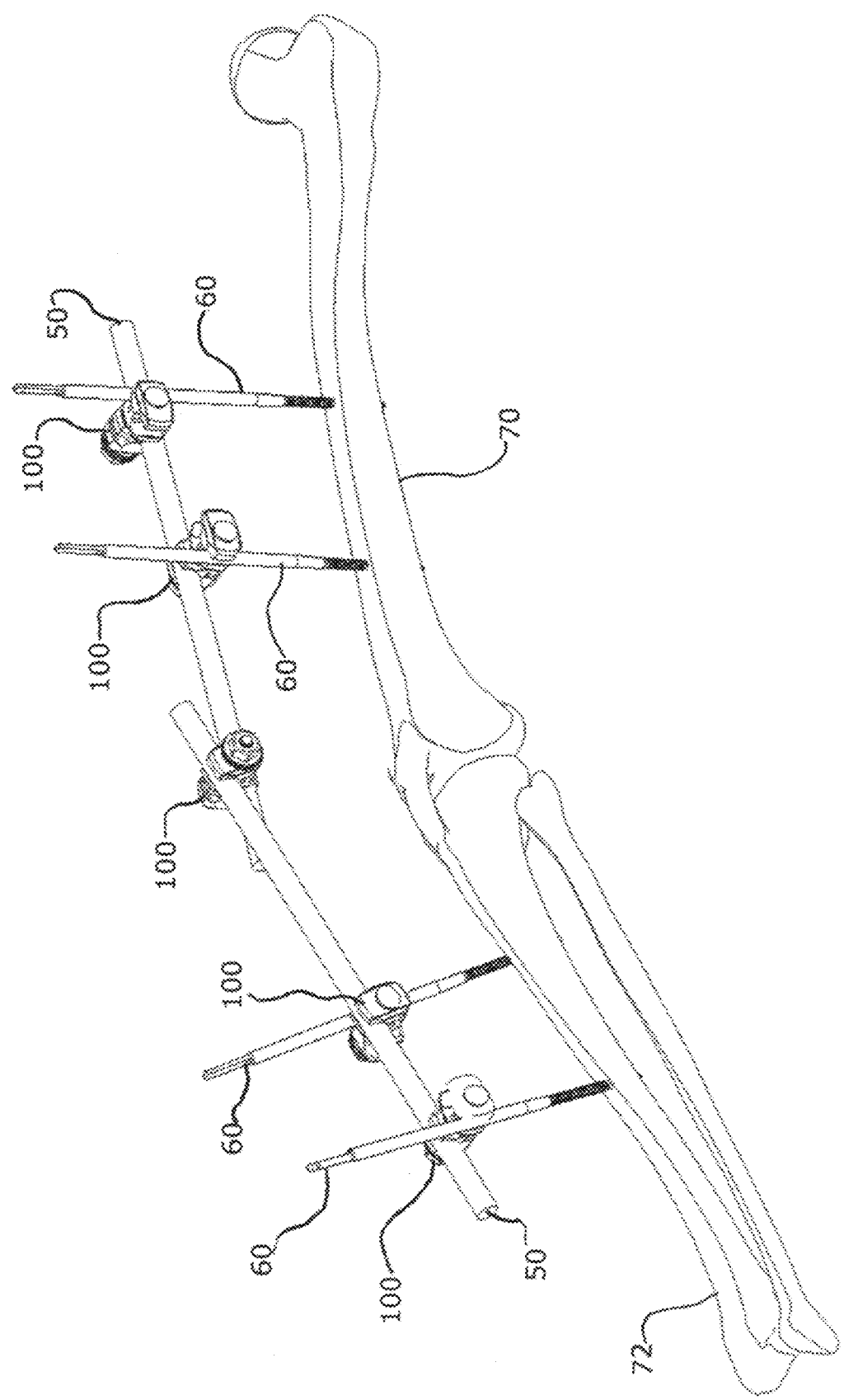
FIG. 1 is a perspective view of an external fixator assembly according to a first exemplary embodiment being used to fixate adjacent bones.

In the drawings, like numerals indicate like elements throughout. Certain terminology is used herein for convenience only and is not to be taken as a limitation on the present invention. The terminology includes the words specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Unless explicitly stated otherwise, each numerical value and range should be interpreted as being approximate as if the word "about" or "approximately" preceded the value of the value or range.

The use of figure numbers and/or figure reference labels in the claims is intended to identify one or more possible embodiments of the claimed subject matter in order to facilitate the interpretation of the claims. Such use is not to be construed as necessarily limiting the scope of those claims to the embodiments shown in the corresponding figures.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments of the present invention.

Although the elements in the following method claims, if any, are recited in a particular sequence with corresponding labeling, unless the claim recitations otherwise imply a particular sequence for implementing some or all of those elements, those elements are not necessarily intended to be limited to being implemented in that particular sequence.

Also for purposes of this description, the terms "couple," "coupling," "coupled," "connect," "connecting," or "connected" refer to any manner known in the art or later developed of joining or connecting two or more elements directly or indirectly to one another, and the interposition of one or more additional elements is contemplated, although not required. Conversely, the terms "directly coupled," "directly connected," etc., imply the absence of such additional elements.

The present disclosure provides embodiments of external fixators that can be used to secure bone fractures. External fixators are used by orthopedic surgeons for various indications to temporarily reduce and fixate fractures that would otherwise be too difficult, cumbersome, or invasive for traditional plate and nail implants. The instruments used in an external fixator are critical to the success of the procedure. The inventive external fixators provide connections that enable a surgeon to rapidly and securely stabilize the fracture.

According to one embodiment, an external fixator system may include a plurality of external fixator assemblies configured to connect a plurality of pins, for example, positioned on opposite sides of a fractured bone, with one more rods. Each fixator assembly may include a plurality of clamp assemblies which are configured to rotate relative to one another when the fixator assembly is in an unlocked position. Once the relative positioning of the pins and/or rods is achieved, for example, to stabilize the fractured bone or bones, the fixator assemblies may be moved to a locked position, such that the clamp assemblies are fixed in position, thereby stabilizing the fracture.

Figure 1A:
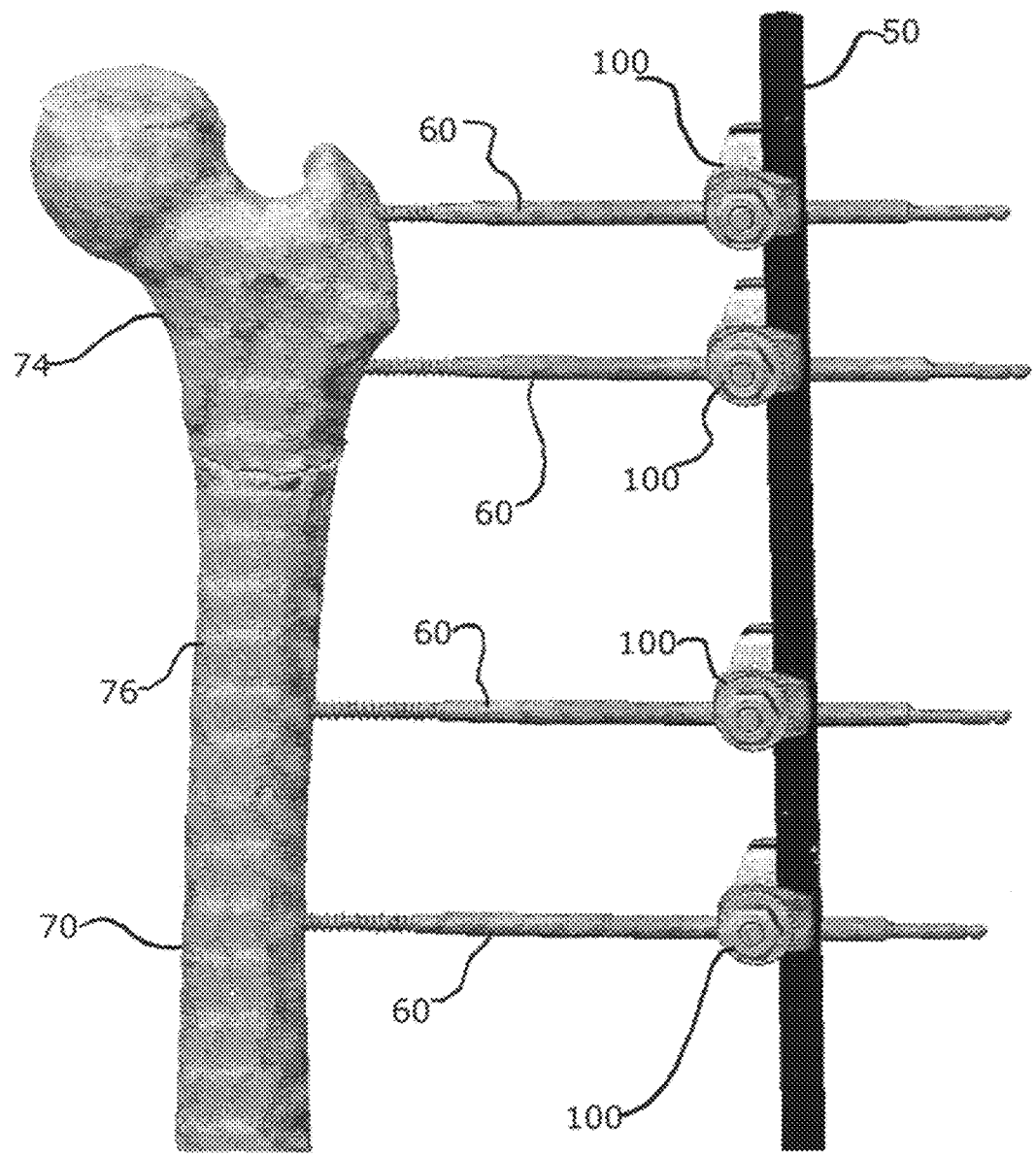
FIG. 1A is a perspective view of the external fixator assembly shown in FIG. 1 being used to fixate broken pieces of the same bone.

Referring to FIGS. 1-5, an external fixator assembly 100 ("fixator assembly 100") according to a first exemplary embodiment is shown. As shown specifically in FIGS. 1 and 1A, fixator assembly 100 is used in conjunction with rods 50 and pins 60 to secure and stabilize adjacent bones 70, 72 (shown in FIG. 1) or to stabilize broken pieces 74, 76 of the same bone 70 (shown in FIG. 1A). While a femur 70 and a tibia 72 are shown in FIG. 1, and femur 70 is shown in FIG. 1A, those skilled in the art will recognize that fixator assembly 100, along with rods 50 and pins 60, can be used to fixate other bones, and other bone pairs as well. Examples of bones may include, but are not limited to, the femur, tibia, fibula, humerus, radius, ulna, and phalanges. Although specific configurations of the external fixator systems are exemplified herein, it will be appreciated that the number, type, and location of rods 50, pins 60, and fixator assemblies 100 can be modified or changed based on the type and location of the bone, fracture, surgeon preference, and the like.

Figure 2:
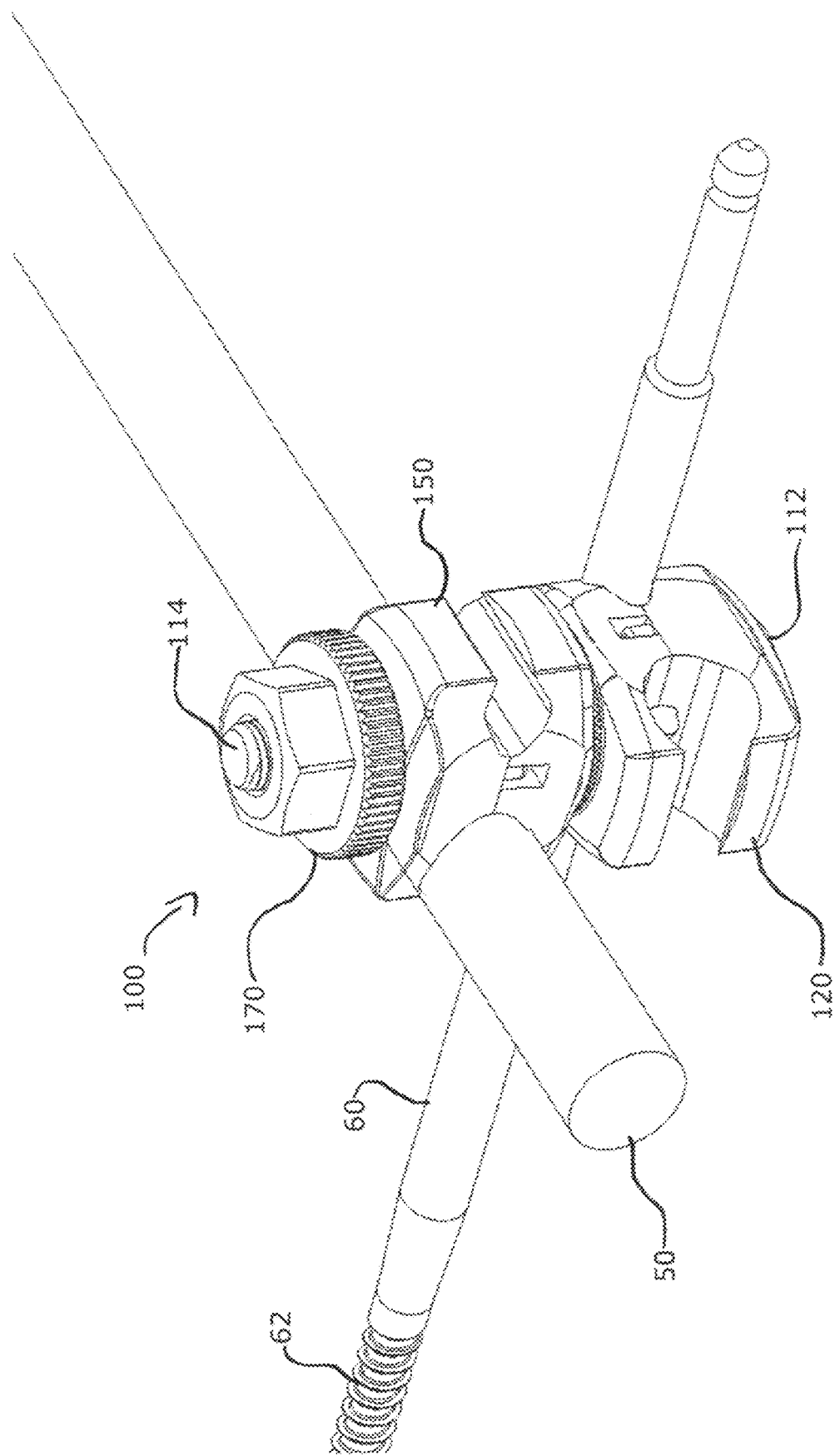
FIG. 2 is a perspective view of the external fixator assembly shown in FIG. 1 with a rod and a pin connected thereto.

As shown in FIG. 2, fixator assembly 100 can be used to releasably secure rod 50 and pin 60 through the use of a plurality of connector assemblies. In an exemplary embodiment, rod 50 can be constructed from a rigid material, such as, for example, a carbon fiber, and can optionally be coated with a material, such as, for example, titanium, to make rod 50 more compatible with MRI use. It is contemplated that the rod 50 may be formed of any suitable material having suitable properties for this application. Rod 50 has a first diameter. The first diameter of rod 50 may range, for example, from 10-12 millimeters, such as, for example, 11 millimeters. The length of rod 50 can be varied depending on the need for a particular application.

Pin 60 can include a bone-engaging end, such as a self-tapping end 62, that is inserted into bone 70, 72. The pin 60 may also be constructed from any suitable biocompatible material. Optionally, end 62 can be coated with an antimicrobial material, such as, for example, silver or silver ions, in order to reduce the likelihood of infection. Pin 60 has a second diameter, smaller than the first diameter of rod 50. The second diameter of the pin 60 may range, for example, from 4-6 millimeters, such as, for example 5 millimeters. The length and diameter of pin 60 can vary, depending on the patient or the injury, as well as surgeon preference.

While FIGS. 1A and 2 show fixator assembly 100 being used to secure a single rod 50 and a single pin 60, those skilled in the art will recognize that fixator assembly 100 can, depending upon the particular situation and injury, be used to connect two rods 50, as shown in FIG. 1, or even two pins 60 (not shown).

Figure 4:
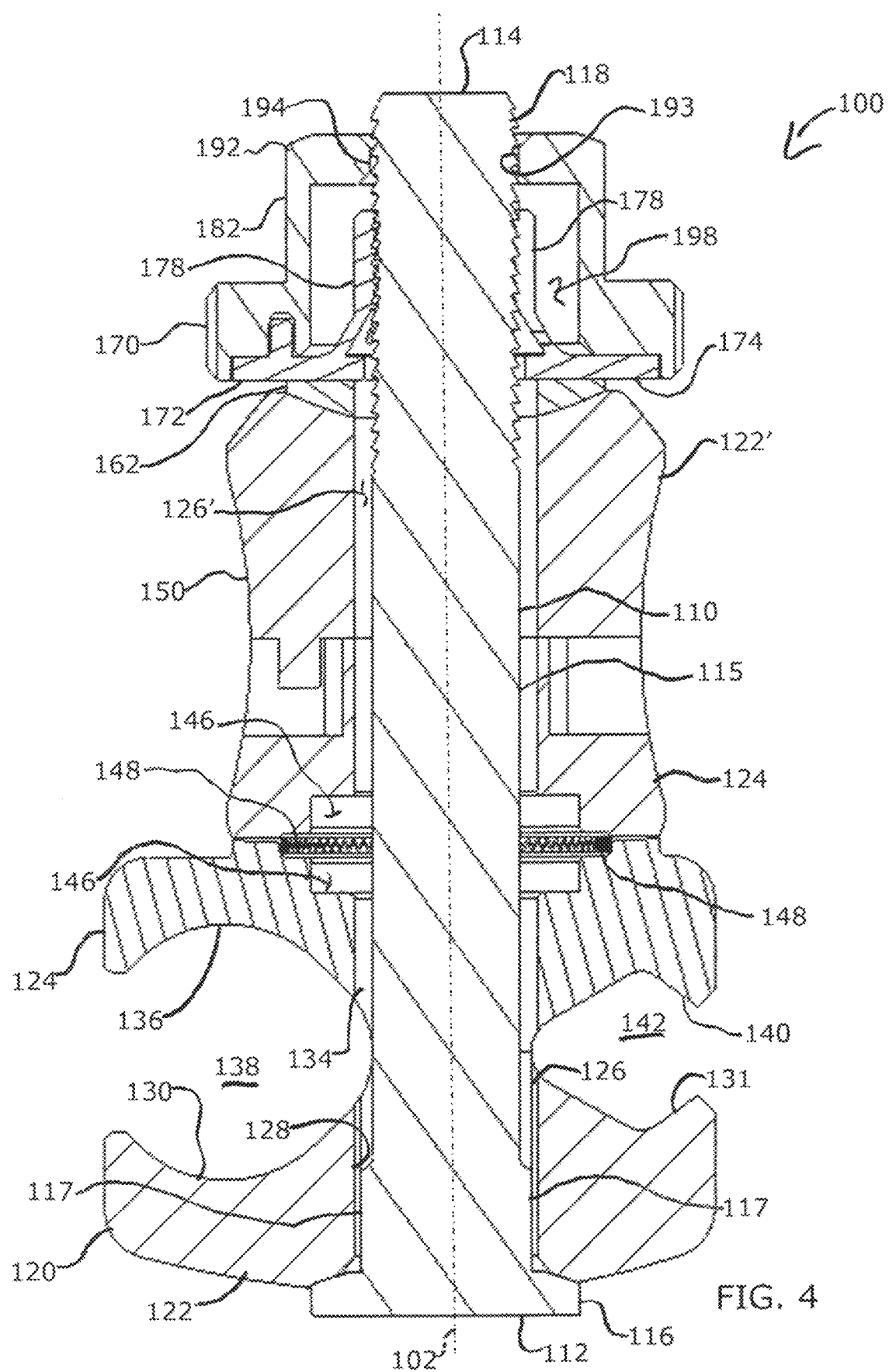
FIG. 4 is a side elevational view, in section, of the external fixator assembly shown in FIG. 1.

As shown in FIG. 4, fixator assembly 100 includes a longitudinal axis 102 extending therethrough. As used herein, the terms "longitudinal", "longitudinally", "axial", and "axially" refer to directions along the length of longitudinal axis 102 or to directions extending parallel to longitudinal axis 102. Further, the terms "radial" and "radially" refer to directions extending perpendicular to or extending outwardly from longitudinal axis 102.

Figure 3:
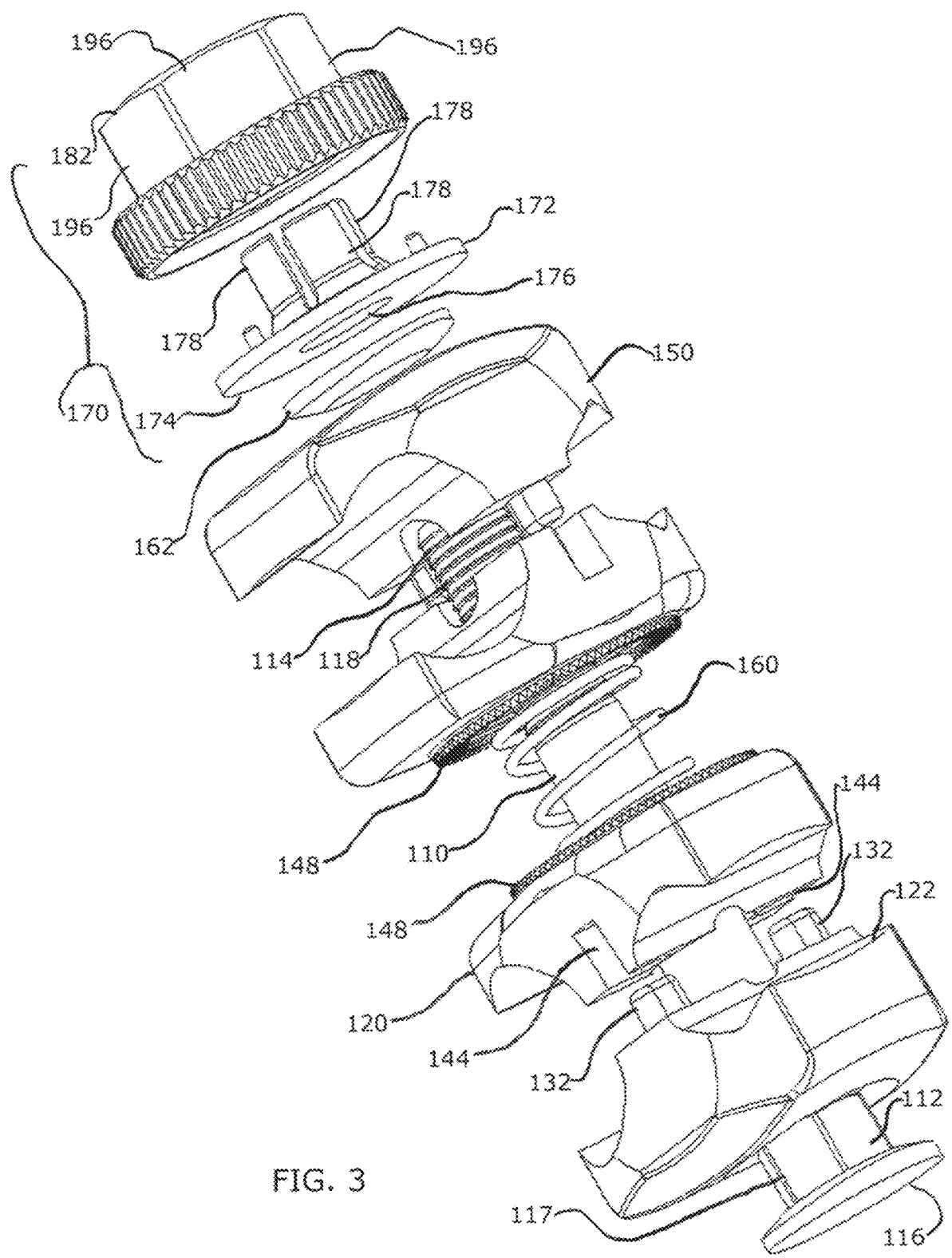
FIG. 3 is an exploded perspective view of the external fixator assembly shown in FIG. 1.

Referring now to FIGS. 2 and 3, fixator assembly 100 includes a shaft 110 and a plurality of clamp assemblies 120, 150 extending along shaft 110. Shaft 110 extends along longitudinal axis 102. A biasing member 160 is disposed between adjacent of the plurality of clamp assemblies 120, 150. A cap, or ratchet, assembly 170 secures clamp assemblies 120, 150 onto shaft 110.

Shaft 110 has a distal end 112 and a proximal end 114 extending away from distal and 112. As used herein with respect to fixator assembly 100, the term "distal" refers to a direction toward the bottom of the page of FIG. 4, and the term "proximal" refers to a direction toward the top of the page of FIG. 4.

Distal end 112 includes a radially extending flange 116 and at least one flat surface 117 extending proximally of flange 116. While FIG. 4 shows two flat surfaces 117, those skilled in the art will recognize that shaft 110 can include more or less than two flat surfaces 117.

Proximal end 114 of shaft 110 has at least one external thread 118. Optionally, a length of shaft 115 between distal end 112 and proximal end 114 can be generally circular, that is, devoid of any flat surfaces or threads. Shaft 110 is sufficiently long to allow for the insertion of clamp assemblies 120, 150 and ratchet assembly 170 thereon.

Clamp assemblies 120, 150 extend along shaft 110 from distal end 112 toward proximal end 114 such that clamp assembly 120 engages flange 116 and clamp assembly 150 engages clamp assembly 120. While two clamp assemblies 120, 150 are shown, those skilled in the art will recognize that more than two clamp assemblies 120, 150 can be used with fixator assembly 100. Alternatively, it can be envisioned that only a single clamp assembly 120 is used with fixator assembly 100.

Clamp assemblies 120, 150 may be, although not necessarily, identical to each other. Clamp assembly 120 includes a lower member 122 and an upper member 124 extending proximally of lower member 122. Lower member 122 includes an axially extending passage 126 that is sized to allow shaft 110 to extend therethrough. Passage 126 can include internal flat surfaces 128 that are adapted to engage with flat surfaces 117 on shaft 110 to prevent lower member 122 of clamp assembly 120 from rotating with respect to shaft 110.

Lower member 122 includes a first generally U-shaped portion 130 having a radius that is sized to receive a portion of rod 50. Lower member 122 also includes a second generally U-shaped portion 131, radially disposed away from first concave portion 130, having a radius that is sized to receive a portion of pin 60. As shown in FIG. 3, lower member 122 also includes a plurality of tangs 132 extending outwardly therefrom in a proximal direction toward upper member 124.

Upper member 124 includes an axially extending passage 134 that is sized to allow shaft 110 to extend therethrough. Upper member 136 further includes a first generally inverted U-shaped portion 136 having a radius that is sized to receive a portion of rod 50, such that, when upper member 124 is biased toward lower member 122, rod 50 is received in a cavity 138 formed by first generally U-shaped portion 130 of lower member 122 and first generally inverted U-shaped portion 136 of upper member 124.

Upper member 124 also includes a second generally inverted U-shaped portion 140, radially disposed away from first generally inverted U-shaped portion 136, having a radius that is sized to receive a portion of pin 60, such that, when upper member 124 is biased toward lower member 122, pin 60 is received in a cavity 142 formed by second generally inverted U-shaped portion 131 of lower member 122 and second generally inverted U-shaped 140 of upper member 124.

As shown in FIG. 3, upper member 124 also includes a plurality of slots 144 formed therein, such that each slot 144 is adapted to releasably receive a tang 132 from lower member 122, thereby preventing upper member 124 from rotating about longitudinal axis 102 relative to lower member 122. Upper member 124 also includes a spring cavity 146 that is sized to receive biasing member 160. A toothed locking half 148 surrounds spring cavity 146.

Clamp assembly 150 is similar to clamp assembly 120 with the exception that, instead of internal flat surfaces 128, clamp assembly 150 includes a member 122' having an axially extending passage 126' sufficiently larger than the diameter of shaft 110 such that clamp assembly 150 is freely rotatable about shaft 110 and is also rotatable relative to clamp assembly 120. As shown in FIGS. 3 and 4, clamp assembly 150 is inserted over shaft 110 "upside down" relative to clamp assembly 120 such that toothed locking half 148 of clamp assembly 150 is engageable with toothed locking half 148 of clamp assembly 120 such that, when clamp assembly 150 is biased against clamp assembly 120, toothed locking half 148 of clamp assembly 150 engages toothed locking half 148 of clamp assembly 120, preventing rotation of clamp assembly 150 with respect to clamp assembly 120.

Each toothed locking half 148 includes a plurality of teeth or the like. In an exemplary embodiment, each toothed locking half 148 includes about 90 teeth, such that clamp assembly 150 can be indexed with respect to clamp assembly 120 about 4°. Those skilled in the art, however, will recognize that each toothed locking half 148 can include more or less than 90 teeth, such that the amount indexing of clamp assembly 150 with respect clamp assembly 120 is adjustable accordingly.

As shown in FIG. 3, biasing member 160 is disposed between clamp assembly 120 and clamp assembly 150 and is retained between clamp assembly 120 and clamp assembly 150 within spring cavities 146. In an exemplary embodiment, biasing member 160 is a helical spring, although those skilled in the art will recognize that other types of biasing members can be used. Biasing member 160 biases clamp assembly 120 and clamp assembly 150 apart from each other, such that clamp assembly 120 and clamp assembly 150 securely engage rod 50 that may be inserted into cavity 138 and/or pin 160 that may be inserted into cavity 142.

Figure 5:
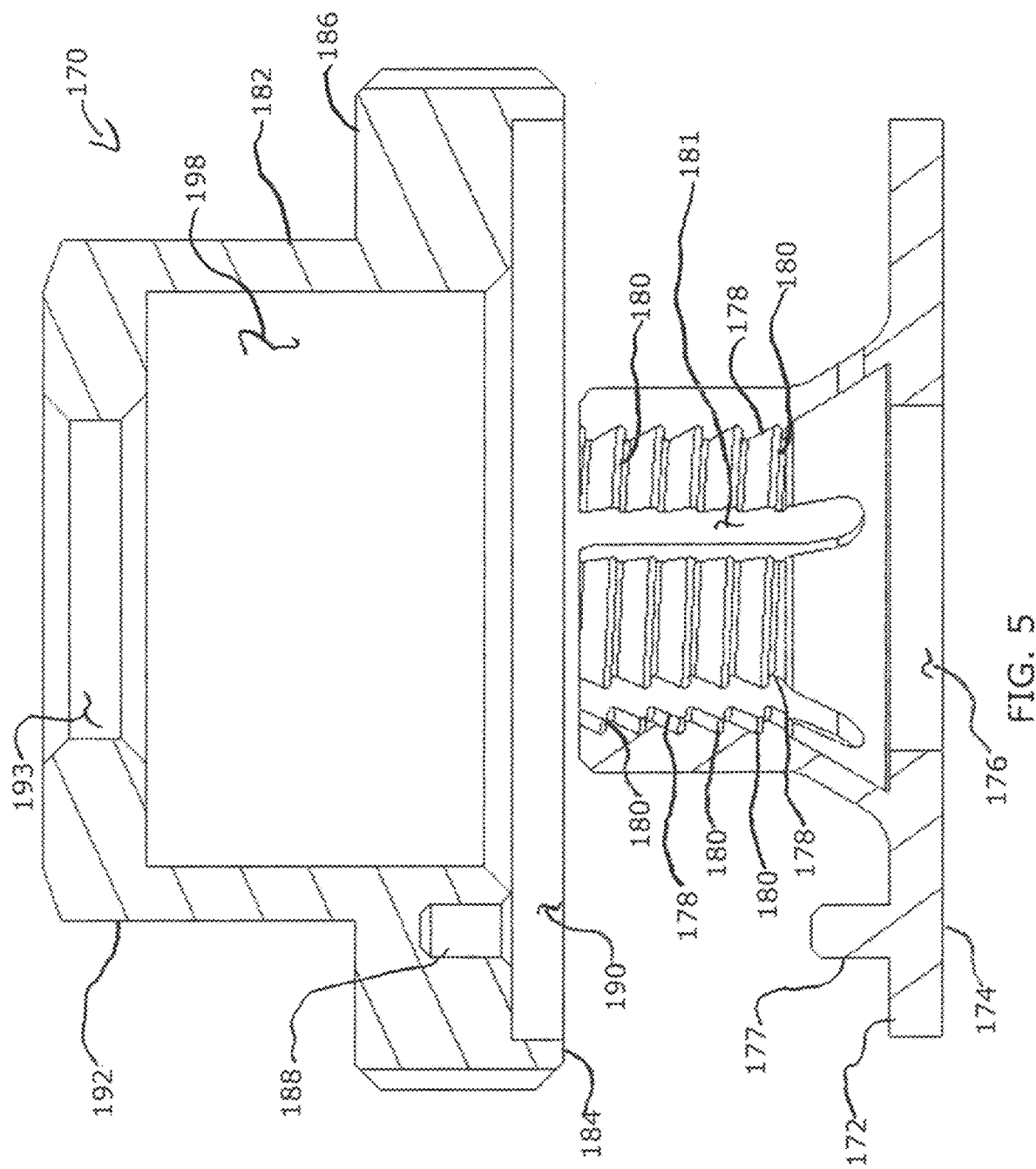
FIG. 5 is an exploded sectional view of a ratchet assembly used with the external fixator assembly shown in FIG. 1.

Referring to FIGS. 3-5, ratchet assembly 170 is disposed over proximal end 114 of shaft 110, such that ratchet assembly 170 biases clamp assemblies 120, 150 toward distal end 112 of shaft 110 and flange 116 so that clamp assemblies 120, 150 are not rotatable with respect to each other. A washer 162 is axially disposed between second clamp assembly 150 and ratchet assembly 170 to distribute compressive forces applied by ratchet assembly 170 onto clamp assembly 150.

Ratchet assembly 170 comprises includes a ratcheting buttress 172 that is adapted to translate axially along shaft 110 from proximal end 114 toward distal end 112. Ratcheting buttress 172 comprises a radially extending annular flange 174 having an axially extending hole 176 therein. Hole 176 is sized to allow shaft 112 to extend therethrough. A tang 177 extends longitudinally outwardly from flange 174.

A plurality of fingers 178 extend proximally around hole 176. Each of the plurality of fingers 178 has a plurality of longitudinally spaced internal ratchet teeth 180 adapted to engage external thread 118 on proximal end 114 of shaft 110. A gap 181 extends between each of adjacent fingers 178 to allow fingers 178 to bias away from longitudinal axis 102, thereby allowing thread 118 to ratchet along ratchet teeth 180 when ratchet assembly 170 is pressed onto shaft 110.

A ratchet housing 182 is disposed over ratcheting buttress 172. Ratchet housing 182 includes a distal end 184 having a radially extending housing flange 186 that is adapted to engage buttress flange 174. Flange 186 includes a slot 188 that is adapted to receive tang 177 from flange 174 such that, when tang 177 is inserted into slot 188, ratchet housing 182 is not rotatable relative to ratcheting buttress 172.

An exterior surface of housing flange 186 includes a contoured surface, such as, for example, a knurled surface, that provides a gripping surface for the user to be able to manually rotate ratchet housing 182 about shaft 110. An interior of housing flange 186 includes a first radially extending cavity 190 adapted to receive annular flange 174 of ratchet buttress 172.

Ratchet housing 182 further includes a proximal body 192 having an internally threaded passage 193 with at least one internal thread 194 adapted to threadably engage external thread 118 on shaft 110. Body 192 further comprises a plurality of flat surfaces 196 extending around a perimeter thereof. Flat surfaces 196 allow for the application of a tool, such as, for example, a wrench or other torqueing devise (not shown) to tighten fixator assembly 100 in order to secure rod(s) 50 and/or pin(s) 60. Body 192 also includes a second radially extending cavity 198 that is adapted to receive the plurality of fingers 178. As shown in FIG. 4, cavity 198 is sufficiently large to allow fingers 178 to bias away from shaft 110 to allow ratcheting buttress 172 to be slid distally along shaft 110.

To assemble fixator assembly 100, first clamp assembly 120 is slid from proximal end 114 of shaft 110 to distal end 112 shaft 110, bottoming out on flange 116. First clamp assembly 120 is aligned such that toothed locking half 148 is facing proximal end 114 of shaft 100. Next, biasing member 160 is slid along shaft 110 such that at least a portion of biasing member 160 is seated within spring cavity 146.

Second clamp assembly 150 is then slid from proximal end 114 of shaft 110, toward first clamp assembly 120. Second clamp assembly 150 is aligned such that toothed locking half 148 is facing distal end 112 of shaft 100 so that at least a remaining portion of biasing member 160 is seated within spring cavity 146 in second clamp assembly 150 and so that toothed locking half 148 of second clamp assembly 150 is facing toothed locking half 148 of first clamp assembly 120.

Washer 162 is slid over shaft 110. Ratchet assembly 170 is then slid over shaft 110 so that internal thread 194 engages external threads 118 on shaft 110. At this point, cavities 138, 142 are sufficiently large to allow rod 50 be slid into cavity 138 and pin 60 to be slid into cavity 142 and also to allow second clamp assembly 150 to axially rotate relative to first clamp assembly 120.

In this condition, the surgeon can align rod 50 and pin 60 in desired positions with respect to fixator assembly 100. The surgeon can then provisionally tighten ratchet assembly 170 by further sliding ratchet assembly 170 distally along shaft 110 and then perform a final tightening of fixator assembly 100 by applying a wrench or other court applying devise (not shown) to flat surfaces 196 on ratchet housing 182 and rotating ratchet housing 182 relative to shaft 110.

Ratchet assembly 170 allows for the rapid application of clamp assemblies 120, 150 onto rod 50 and/or pin 60. Ratchet assembly 170 also provides a quick method for provisional tightening of fixator assembly 100 while the surgeon is assembling fixator assembly 100 with bar(s) 50 and pin(s) 60. Once set, a final tightening of ratchet assembly 170 can be applied using a torque limiting adapter, for example, under power.

According to one embodiment, a method of installing the external fixator system, for example, at the site of one or more broken bones, may include inserting one or more pins 60 into the afflicted bone (for example, on opposite sides of the fracture); attaching one or more fixator assemblies 100 to each pin 60; and securing the one or more pins 60 to adjacent pins 60 by connecting one or more rods 50 between adjacent fixator assemblies 100. If the construct needs to be extended, for example, to bridge multiple bones or multiple fractures, the same fixator assembly 100 can also be used to connect two or more rods 50 together.

Figure 6:
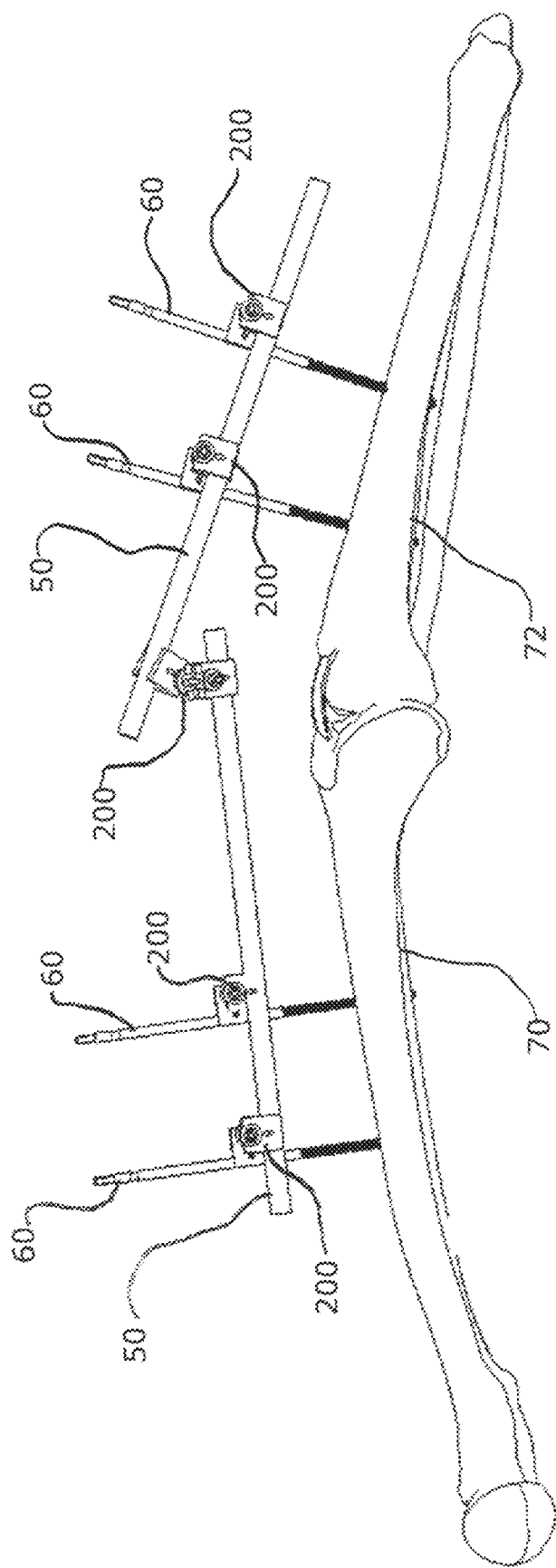
FIG. 6 is a perspective view of external fixator assembly according to a second exemplary embodiment being used to fixate adjacent bones.
Figure 7A:
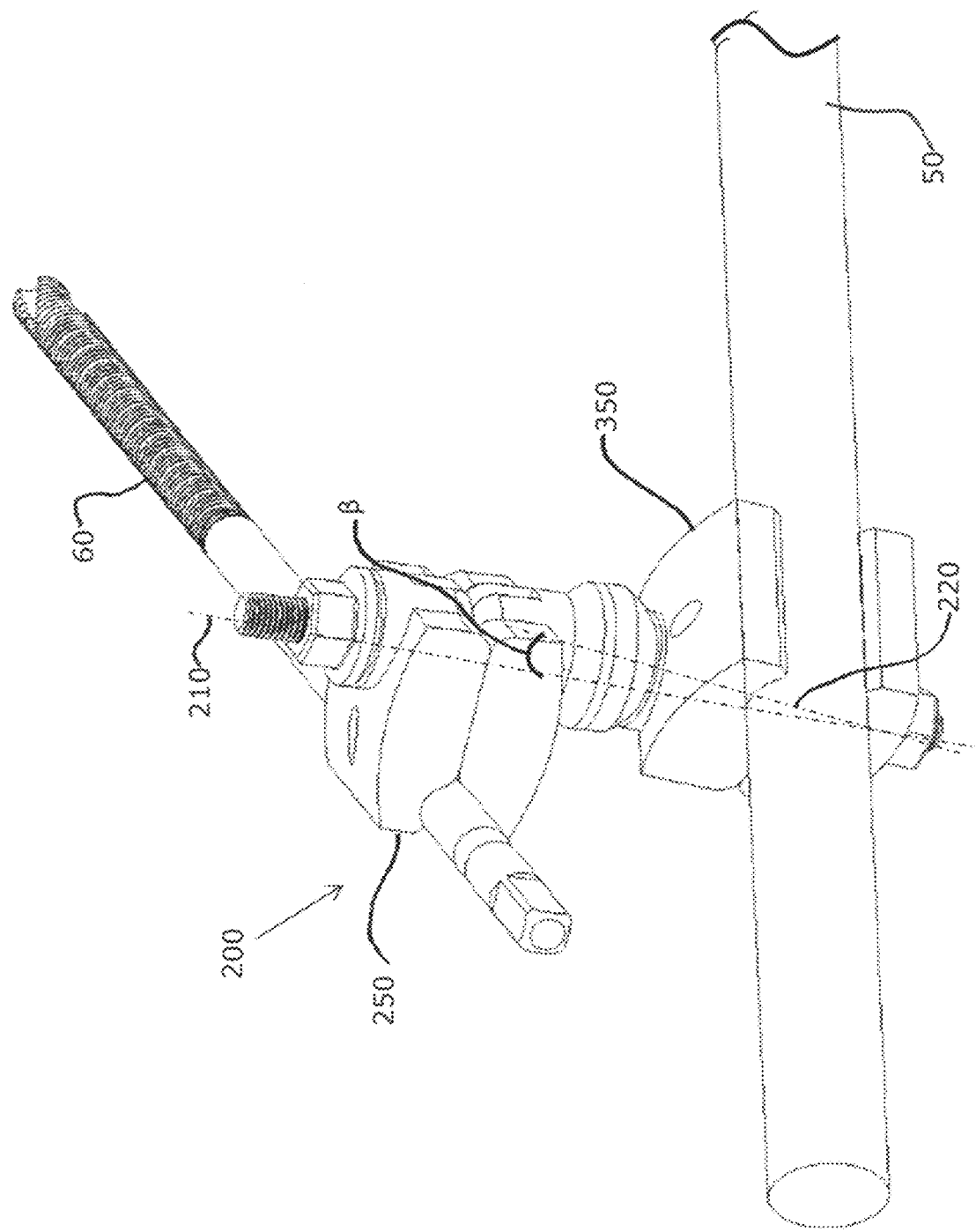
FIG. 7A is a perspective view of the external fixator assembly shown in FIG. 6 with a rod and a pin connected thereto.

An alternative embodiment of an external fixator assembly 200 ("fixator assembly 200") is shown in FIGS. 6-10. FIG. 6 shows fixator assembly 200 being used with both rods 50 and pins 60 to secure and stabilize adjacent bones 70, 72 in a patient. FIG. 7 shows fixator assembly 200 being used to secure two rods 50 in a generally parallel arrangement, while FIG. 7A shows fixator assembly 200 being used to secure a single rod 50 and a single pin 60 in a skewed arrangement.

Figure 8:
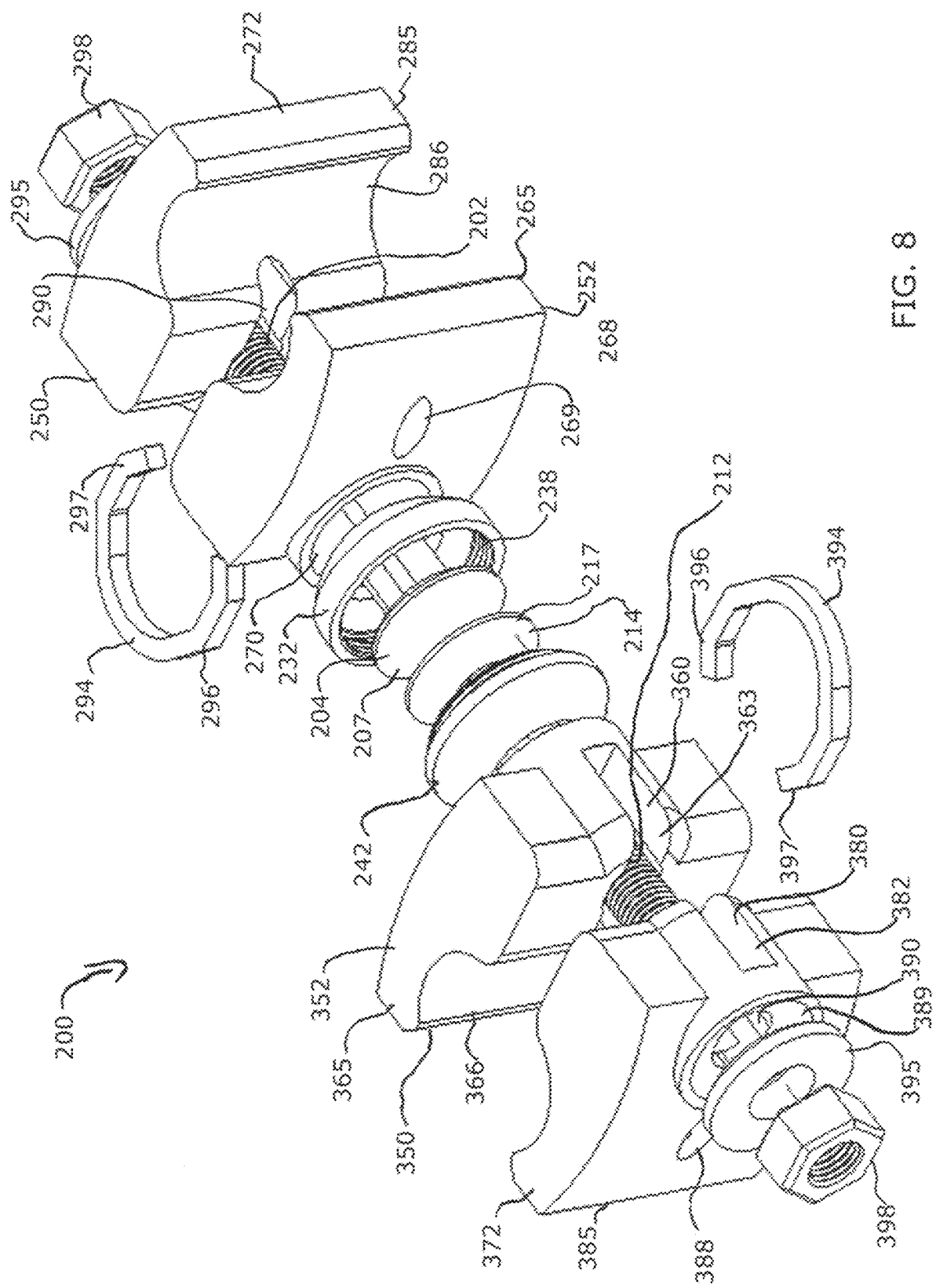
FIG. 8 is an exploded perspective view of the external fixator assembly shown in FIG. 6.
Figure 9:
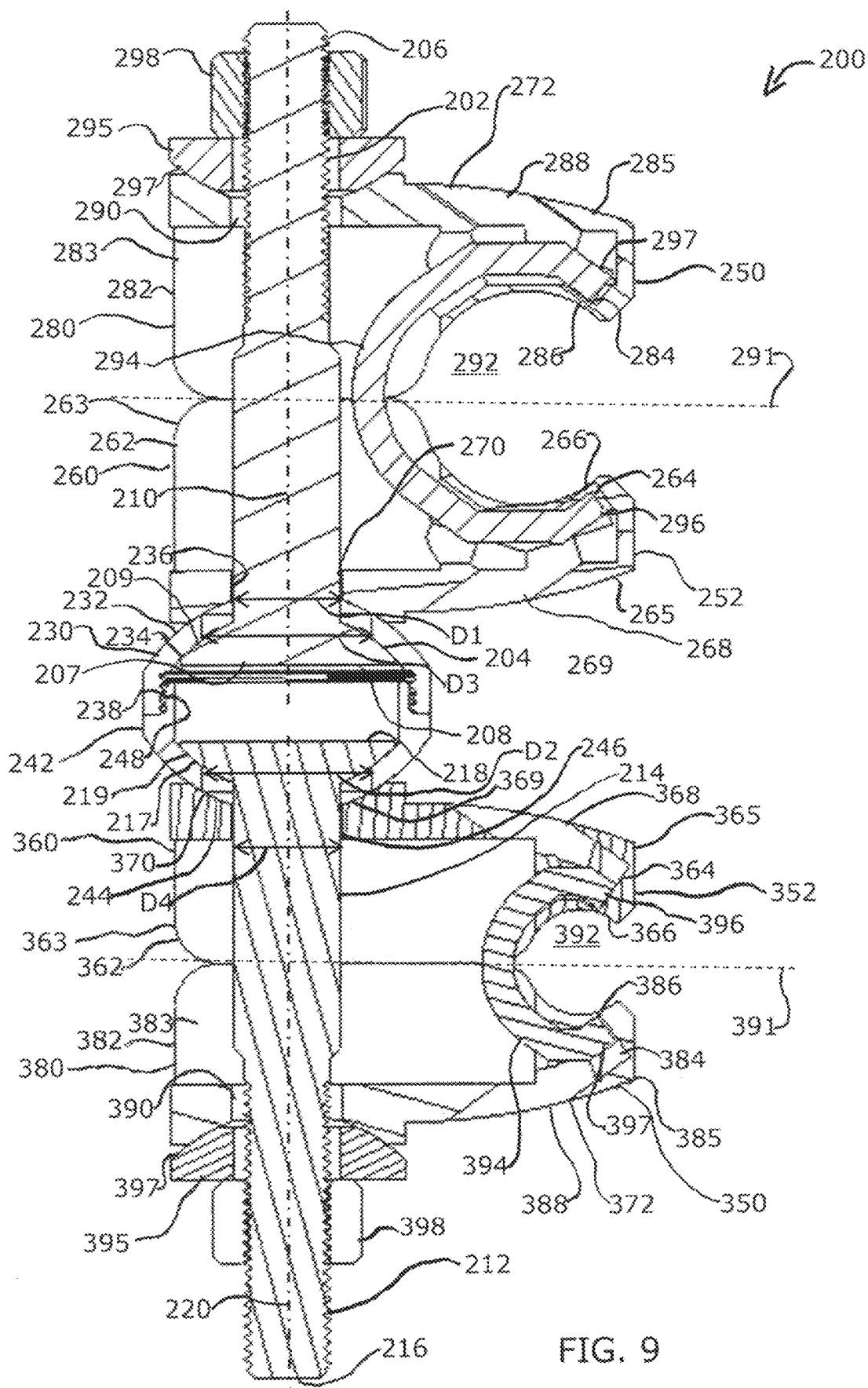
FIG. 9 is a side elevational view, in section, of the external fixator assembly shown in FIG. 6.

Referring to the exploded view of fixator assembly 200, shown in FIG. 8 and the sectional view shown in FIG. 9, fixator assembly 200 includes a first shaft 202 having a first coupling end 204 and a first free end 206. First coupling end 204 has an outer diameter D1. First free end 206 has a narrower diameter than outer diameter D1. First coupling end 204 terminates in a first lip 207, having a generally flat face 208 and a generally convex outer face 209. A first longitudinal axis 210 extends along the length of first shaft 202.

Similarly, a second shaft 212 has a second coupling end 214 and a second free end 216. Second coupling end 214 has an outer diameter D2. Second free end 216 has a narrower diameter than outer diameter D2. Second coupling end 214 terminates in a second lip 217, having a generally flat face 218 and a generally convex outer face 219. A second longitudinal axis 220 extends along the length of second shaft 212.

A coupling 230 pivotally retains first coupling end 204 and second coupling end 214 therein. Coupling 230 includes a first cup, or clamshell portion 232 having a concave interface 234 that is contoured to receive generally convex outer face 209 of first coupling end 204. Additionally, first clamshell portion 232 includes an opening 236, having a diameter D3, such that outer diameter D1 of first coupling end 204 is smaller than the diameter D3, but first lip 207 is larger than the size of opening 236 such that, when first shaft 202 is inserted through opening 236, first lip 207 is retained within first clamshell portion 232.

Likewise, coupling 230 also includes a second cup, or clamshell portion 242 having a concave interface 244 that is contoured to receive generally convex outer face 219 of second coupling end 214. Additionally, second clamshell portion 242 includes an opening 246, having a diameter D4, such that outer diameter D2 of second coupling end 214 is smaller than the diameter D4, but second lip 217 is larger than the size of opening 246 such that, when second shaft 212 is inserted through opening 246, second lip 217 is retained within second clamshell portion 242.

In an exemplary embodiment, first clamshell portion 232 includes female threads 238 and second clamshell portion 242 includes matching male threads 248 such that first clamshell portion 232 can be threadedly connected to second clamshell portion 242. Optionally, to prevent first clamshell portion 232 from being separated from second clamshell portion 242, first clamshell portion 232 can be welded or otherwise permanently secured to second clamshell portion 242 at the connection of female threads 238 and male threads 248.

As used herein, the term "inner" is used to define a direction toward coupling 230, and the term "outer" is used to define a direction away from coupling 230. A first clamp assembly 250 is disposed on first shaft 202 between coupling 230 and first free end 206 of first shaft 202. First clamp assembly 250 includes a first inner clamp member 252 disposed proximate to coupling 230. First inner clamp member 252 has a first inner slot 260. First inner slot 260 has an open end 262, located at a shaft end 263, and a blind end 264, located at a finger end 265. Finger end 265 includes an arcuate cutout 266 that extends in an arc greater than 90°. A drill passage 268 extends obliquely through finger end 265 to allow for the formation of blind end 264.

First inner clamp member 252 also includes a concave surface 269 that engages concave interface 234 of first clamshell portion 232 so that first inner clamp member 252 is slidable along at least a portion of concave interface 234. Additionally, first inner clamp member 252 includes a through-opening 270 sized to allow first shaft 202 to pass therethrough. Through-opening 270 is sized such that a minimum clearance exists between through-opening 270 and first shaft 202.

First clamp assembly 250 further includes a first outer clamp member 272 disposed proximate to first free end 206. First outer clamp member 272 has a first outer slot 280. First outer slot 280 has an open end 282, located at shaft end 283, and a blind end 284, located at a finger end 285. Finger end 285 includes an arcuate cutout 286 that extends in an arc greater than 90°. A drill passage 288 extends obliquely through finger end 285 to allow for the formation of blind end 284. Similar to concave surface 269 in first inner clamp member 252, first outer clamp member 272 also includes a concave surface 289. Additionally, first outer clamp member 272 includes a through-opening 290 sized to allow free end 206 of first shaft 202 to pass therethrough.

In an exemplary embodiment, first outer clamp member 272 is generally a mirror image of first inner clamp member 252 across a transverse axis 291. When first inner clamp member 252 and first outer clamp member 272 are assembled on shaft 202, as shown in FIG. 9, a retaining cavity 292 is formed between finger end 265 and finger end 285. Retaining cavity 292 has a wall portion that extends an arc of greater than 180°. In an exemplary embodiment, retaining cavity 292 is sized to allow the insertion of rod 50 therein.

A first biasing member 294 is disposed in first inner slot 260 and first outer slot 280. In an exemplary embodiment, first biasing member 294 is a C-shaped spring having a first end 296 that is inserted into blind end 264 of first inner slot 260 and a second end 297 that is inserted into blind end 284 of first outer slot 280 such that first biasing member 294 biases first inner clamp member 252 toward first outer clamp member 272.

A first washer 295 is disposed over first shaft 202 and against first outer clamp member 272. First washer 295 has a contoured inner surface 297 for engagement with concave surface 289. A nut 298 is threaded onto first shaft 202 to secure first clamp assembly 250 against coupling 230.

Similar to first clamp assembly 250, a second clamp assembly 350 is disposed on second shaft 212 between coupling 230 and second free end 216. Second clamp assembly 350 includes a second inner clamp member 352 disposed proximate to coupling 230. Second inner clamp member 352 has a second inner slot 360. Second inner slot 360 has an open end 362, located at a shaft end 363 and a blind end 364, located at a finger end 365. Finger end 365 includes an arcuate cutout 366 that extends in an arc greater than 90°. A drill passage 368 extends obliquely through finger end 365 to allow for the formation of blind end 364.

Second inner clamp member 352 also includes a concave surface 369 that engages concave interface 334 of second clamshell portion 242 so that second inner clamp member 352 is slidable along at least a portion of concave interface 334. Additionally, second inner clamp member 352 includes a through-opening 370 sized to allow second shaft 212 to pass therethrough. Through-opening 370 is sized such that a minimum clearance exists between through-opening 370 and second shaft 212.

Second clamp assembly 350 further includes a second outer clamp member 372 disposed proximate to second free end 216. Second outer clamp member 372 has a second outer slot 380. Second outer slot 380 has an open end 382, located at shaft end 383 and a blind end 384, located at a finger end 385. Finger end 385 includes an arcuate cutout 386 that extends in an arc greater than 90°. A drill passage 388 extends obliquely through finger end 385 to allow for the formation of blind end 384. Similar to concave surface 369 in second inner clamp member 352, second outer clamp member 372 also includes a concave surface 389. Additionally, second outer clamp member 372 includes a through-opening 390 sized to allow free end 216 of second shaft 212 to pass therethrough.

In an exemplary embodiment, second outer clamp member 372 is generally a mirror image of second inner clamp member 352 across a transverse axis 391. When second inner clamp member 352 and second outer clamp member 372 are assembled on shaft 212, as shown in FIG. 9, a retaining cavity 392 is formed between finger end 365 and finger end 385. Retaining cavity 392 has a wall portion that extends an arc of greater than 180°. In an exemplary embodiment, retaining cavity 392 is sized to allow the insertion of pin 60 therein.

A second biasing member 394 is disposed in second inner slot 360 and second outer slot 380. In an exemplary embodiment, second biasing member 394 is a C-shaped spring having a first end 396 that is inserted into blind end 364 of second inner slot 360 and a second end 397 that is inserted into blind end 384 of second outer slot 380 such that second biasing member 394 biases second inner clamp member 352 toward second outer clamp member 372.

A second washer 395 is disposed over second shaft 212 and against second outer clamp member 372. Second washer 395 has a contoured inner surface 397 for engagement with concave surface 389. A nut 398 is threaded onto second shaft 212 to secure second clamp assembly 350 against coupling 230.

To assemble fixator assembly 200, first shaft 202 is inserted into first clamshell portion 232, such that first lip 207 is seated in first clamshell portion 232 and second shaft 212 and second shaft 212 is inserted into second clamshell portion 242, such that second lip 217 is seated in second clamshell portion 242. First and second clamshell portion 232, 242 are then fixedly secured to each other.

First inner clamp member 252 and first outer clamp 272 are placed next to each other, such that first inner slot 260 and first outer slot 280 are aligned with each other, forming first clamp assembly 250. First biasing member 294 is then inserted through first inner slot 260 and first outer slot 280 such that first end 296 of first biasing member 294 is inserted into blind end 264 of first inner slot 260 and second end 297 of biasing member 294 is inserted into blind end 284 of first outer slot 280, thereby securing first inner clamp member 252 and first outer clamp member 272 to each other and providing a compressive force to bias finger end 265 of first inner clamp member 252 and finger end 285 of first outer clamp member 272 toward each other.

First clamp assembly 250 is then slid over first shaft 202 such that first shaft 202 extends through through-openings 270, 290 and first shaft 202 extends through first inner slot 260 and first outer slot 280 such that first shaft 202 retains first biasing member 294 in first inner slot 260 and first outer slot 280. Washer 295 is slid over first shaft 202 and nut 298 is then threaded onto first shaft 202 to secure first clamp assembly 250 against coupling 230.

Similarly, second inner clamp member 352 and second outer clamp 372 are placed next to each other, such that second inner slot 360 and second outer slot 380 are aligned with each other, forming second clamp assembly 350. Second biasing member 394 is then inserted through second inner slot 360 and second outer slot 380 such that first end 396 of second biasing member 394 is inserted into blind end 364 of second inner slot 360 and second end 397 of biasing member 394 is inserted into blind end 384 of second outer slot 380, thereby securing second inner clamp member 352 and second outer clamp member 372 to each other and providing a compressive force to bias finger end 365 of second inner clamp member 352 and finger end 385 of second outer clamp member 372 toward each other.

Second clamp assembly 350 is then slid over second shaft 212 such that second shaft 212 extends through through-openings 370, 390 and second shaft 212 extends through second inner slot 360 and second outer slot 280 such that second shaft 212 retains second biasing member 394 in second inner slot 360 and second outer slot 380. Washer 395 is slid over second shaft 212, and nut 398 is then threaded onto second shaft 212 to secure second clamp assembly 350 against coupling 230.

Rod 50 can be inserted into retaining cavity 292. Because retaining cavity 292 has a wall portion that defines an arc of greater than 180°, with rod 50 in retaining cavity 292, the compressive action of biasing member 294 and the tightening of nut 298 securely retain rod 50 within retaining cavity 292.

Similarly, pin 60 can be inserted into retaining cavity 392. Because retaining cavity 392 has a wall portion that defines an arc of greater than 180°, with pin 60 in retaining cavity 392, the compressive action of biasing member 394 and the tightening of nut 298 securely retain pin 60 within retaining cavity 392.

In order to rotate first clamp assembly 250 about first shaft 210, nut 298 can be loosened sufficiently to allow such rotation. The compressive action of first biasing member 294 retains rod 50 within retaining cavity 292 to allow such rotation, without adversely affecting the retention of rod 50 within first clamp assembly 250.

Likewise, in order to rotate second clamp assembly 350 about second shaft 220, nut 398 can be loosened sufficiently to allow such rotation. The compressive action of second biasing member 394 retains pin 60 within retaining cavity 392 to allow such rotation, without adversely affecting the retention of pin 60 within second clamp assembly 350.

Figure 10:
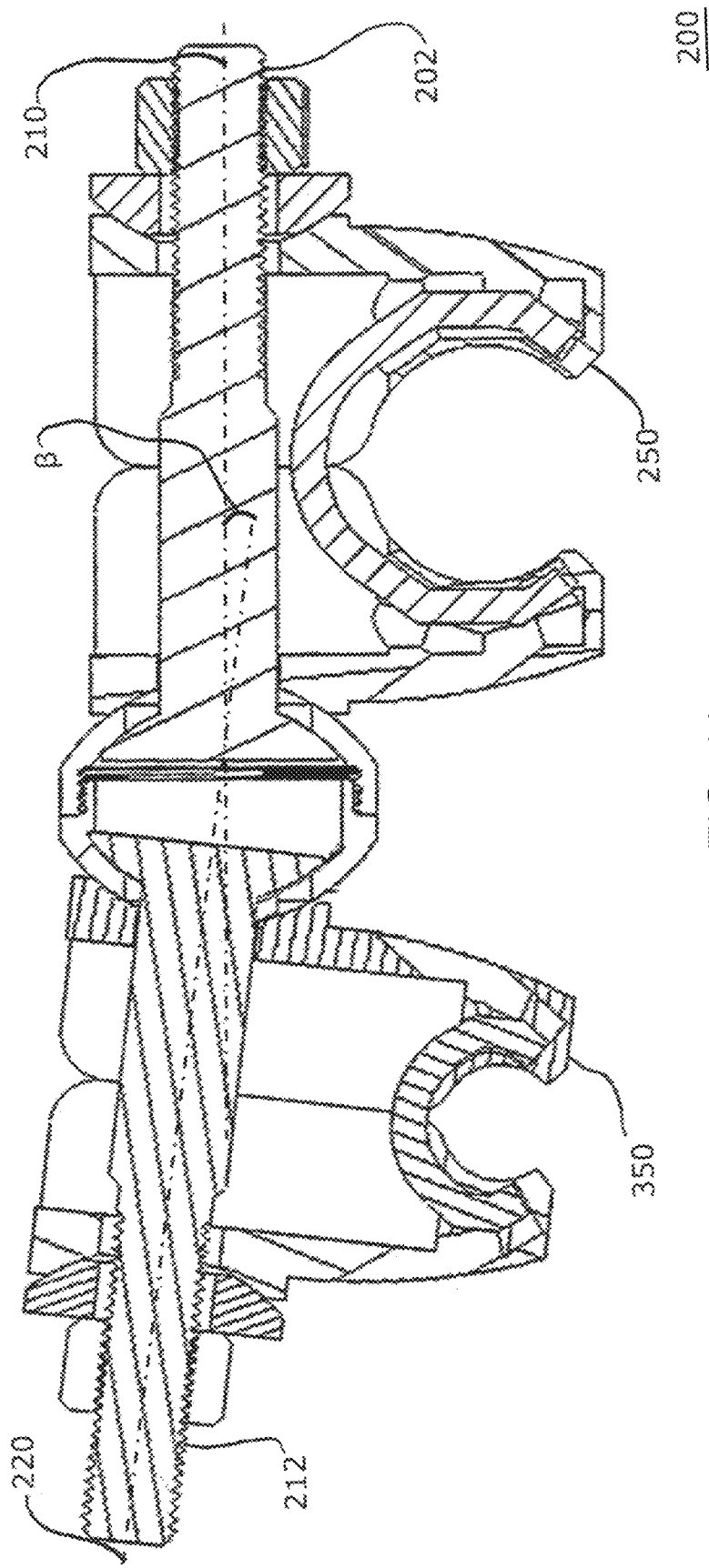
FIG. 10 is a side elevational view, in section, of the external fixator assembly shown in FIG. 9, with one shaft pivoted relative to the other shaft.

Additionally, because diameter D1 of first coupling end 204 is smaller than diameter D3 of opening 236 in first clamshell portion 232 and diameter D2 of second coupling end 214 is smaller than diameter D4 of opening 246 in second clamshell portion 242, first longitudinal axis 210 of first shaft 202 does not necessarily have to be collinear with second longitudinal axis 220 of second shaft 212. As shown in FIG. 10, first longitudinal axis 210 can extend at an oblique angle R relative to second longitudinal axis 220, allowing for first clamp assembly 250 to angularly pivot relative to second clamp assembly 350, thereby allowing for angular adjustment of first clamp assembly 250 relative to second clamp assembly 350. FIG. 7A shows an example of such angular adjustment.

According to one embodiment, a method of installing the external fixator system, for example, at the site of one or more broken bones, may include inserting a first pin 60 into the afflicted bone on one side of the fracture; inserting a second pin 60 on an opposite side of the fracture; attaching a first fixator assembly 200 to the first pin 60 and a second fixator assembly 200 to the second pin 60; articulating the first or second clamp assembly 250, 350 relative to the other of the first or second clamp assembly 250, 350 into a position for receiving the rod 50; connecting the rod 50 between the first and second fixator assemblies 200 in order to secure the first and second pins 60 together. If the construct needs to be extended, for example, to bridge multiple bones or multiple fractures, a third fixator assembly 200 may be articulated and positioned to secure and connect the rod 50 to an additional rod 50.

FIG. 11 is a top perspective view of an external fixator assembly according to a third exemplary embodiment being used to fixate adjacent bones. The external fixator assembly 300 comprises similar features as in prior embodiments, including a first clamp assembly 320, a second clamp assembly 350, a ratchet assembly 370, and a shaft 310 extending through each of the components. The first clamp assembly 320 comprises an upper member 324' operably attached to a lower member 321', thereby forming a pair of slots for receiving one or more pins or rods. Likewise, the second clamp assembly 350 comprises an upper member 324 operably attached to a lower member 321, thereby forming a pair of slots for receiving one or more pins or rods. However, in the present embodiment, at least one of the slots for receiving the one or more pins or rods is formed by one or more flat surfaces (shown in FIG. 12). By providing such flat surfaces, this advantageously provides a distinctly shaped slot that eases both insertion and removal of any pin or rod that is inserted within the slot.

In some embodiments, the first clamp assembly 320 comprises an upper member 324' having a first downward facing recessed portion 336' and a second downward facing recessed portion 340'. In some embodiments, the first downward facing recessed portion 336' and the second downward facing recessed portion 340' are U-shaped or V-shaped. In addition, the first clamp assembly 320 further comprises a lower member 321' having a first upward facing recessed portion 330' and a second upward facing recessed portion 331'. In some embodiments, the first upward facing recessed portion 330' and the second upward facing recessed portion 331' are U-shaped or V-shaped. In some embodiments, the first downward facing recessed portion 336' faces the first upward facing recessed portion 330', thereby forming a first slot in the first clamp assembly for receiving a rod or pin. In some embodiments, the second downward facing recessed portion 340' faces the second upward facing recessed portion 331', thereby forming a second slot in the first clamp assembly for receiving a rod or pin. In some embodiments, the first slot and the second slot in the first clamp assembly 320 are the same size. In other embodiments, the first slot and the second slot in the first clamp assembly 320 are of different sizes.

In some embodiments, the second clamp assembly 350 comprises an upper member 324 having a first downward facing recessed portion 336 and a second downward facing recessed portion 340. In some embodiments, the first downward facing recessed portion 336 and the second downward facing recessed portion 340 are U-shaped or V-shaped. In addition, the second clamp assembly 350 comprises an upward facing flat portion 330 and an upward facing recessed portion 331. In some embodiments, the first downward facing recessed portion 336 faces the first upward facing flat portion 330, thereby forming a first slot in the second clamp assembly for receiving a rod or pin. In some embodiments, the second downward facing recessed portion 340 faces the second upward facing recessed portion 331, thereby forming a second slot in the second clamp assembly for receiving a rod or pin.

FIG. 12 is a close-up view of a clamp assembly of the external fixator assembly of FIG. 11. From this view, one can see how the clamp assembly 350 includes a first slot for receiving a rod or a pin and a second slot for receiving a rod or a pin, wherein the first slot is different from the second slot. The first slot in the clamp assembly 350 is formed by a first downward facing recessed portion 336 which opposes an upward facing flat portion 330, while the second slot in the clamp assembly 350 is formed by a second downward facing recessed portion 340 which opposes an upward facing recessed portion 331. In other words, the first slot is formed by a single arc opposing a flat surface, while the second slot is formed by opposing double arcs.

As shown in FIG. 12, the first slot further includes flat surfaces 332, 334 that extend between the flat portion 330 and the recessed portion 336, thereby connecting the portions to form the first slot. By providing a first slot with the flat surfaces, this advantageously creates a slot whereby a rod or pin can be easily inserted, but also easily removed from the first slot. As shown in FIG. 12, the second slot is formed by the second downward facing recessed portion 340 transitioning into the upward facing recessed portion 331, thereby forming a slot formed of double arcs.

FIG. 13 is a top perspective view of an external fixator assembly according to a fourth exemplary embodiment being used to fixate adjacent bones. The external fixator assembly 400 comprises similar features as in prior embodiments, including a first clamp assembly 420, a second clamp assembly 450, a ratchet assembly 470, and a shaft 410 extending through each of the components. The first clamp assembly 420 comprises an upper member 424' operably attached to a lower member 421', thereby forming a pair of slots for receiving one or more pins or rods. However, the second clamp assembly 450 comprises an upper member 424 operably attached to a lower member 421, whereby only a single slot is formed for receiving a single rod. As shown in FIG. 13, the single slot is opposed to a rod/pin free zone 433. In other words, the external fixator 400 including the first clamp assembly 420 and the second clamp assembly 450 includes a total of three slots for receiving one or more pins or rods. By providing a second clamp assembly 450 having a single slot for receiving a rod, this advantageously provides a more simplistic connection mechanism and reduces the risk of confusion to a surgeon during surgery.

FIG. 14 is a close-up view of a pair of clamp assemblies of the external fixator assembly of FIG. 13. From this view, one can see how the clamp assembly 450 includes a first slot for receiving a rod that is opposed to a rod/pin free zone 433. The first slot in the clamp assembly 450 is formed by a first downward facing recessed portion 436 which opposes a first upward facing recessed portion 430. The rod/pin free zone 433 is formed of two flat surfaces 437, 439 forming a V-opening relative to one another. The two flat surfaces 437, 439 are sized and shaped such that neither a rod nor pin will not be retained (or in some cases, received) in the recess formed therebetween.

In contrast to the clamp assembly 450, the clamp assembly 420 includes two opposing slots for receiving one or more rods and/or pins. The first slot is formed of a first downward facing recessed portion 436' which opposes a first upward facing recessed portion 430', while the second slot is formed of a second downward facing recessed portion 440' which opposes a second upward facing recessed portion 431'. As shown in FIG. 14, the first slot for receiving a rod is larger than the second slot for receiving a pin.

Figure 15:
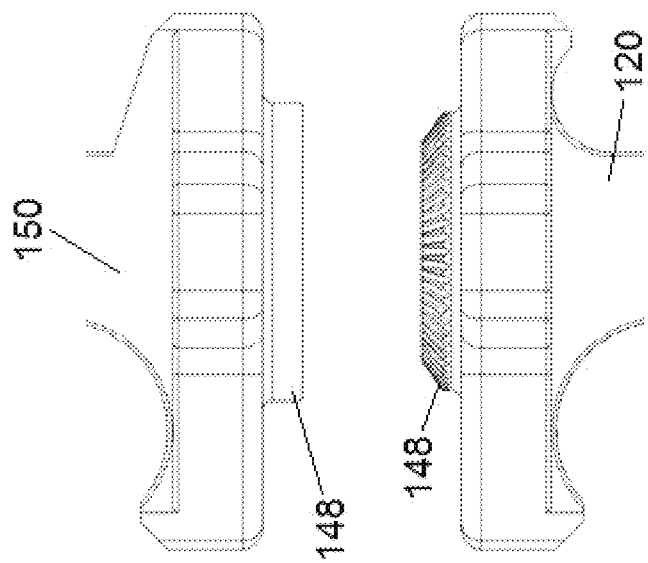
FIG. 15 is a front view of an interface between a first clamp assembly and a second clamp assembly in accordance with some embodiments.

FIG. 15 is a front view of an interface between a first clamp assembly and a second clamp assembly in accordance with some embodiments. The first clamp assembly 120 comprises an upwardly extending toothed locking half 148, while the second clamp assembly 150 comprises a downwardly extending toothed locking half. In some embodiments, the first clamp assembly 120 comprises an upwardly extending toothed locking half 148 in the form of a female mating feature, while the second clamp assembly 150 comprises a downwardly extending toothed locking half 148 in the form of a male mating feature that is received in the female mating feature. In some embodiments, both the downwardly extending toothed locking half 148 and the upwardly extending toothed locking half comprise grooves in the form of a beveled star grind. When both of the locking halves 148 are engaged with one another, the beveled star grinds engage one another, thereby preventing relative rotation between the first clamp assembly 120 and the second clamp assembly 150. In addition, advantageously the elevated and indented portions of the male and female mating features also allow for the grooves of the star grinds to self-align once tightened. Once the first clamp assembly 120 and the second clamp assembly 150 are tightened, the beveled star grinds are completely enclosed and not visible externally (as shown in FIG. 18). The beveled star grinds disclosed herein can be used with any of the embodiments above of external fixators.

Figure 16:
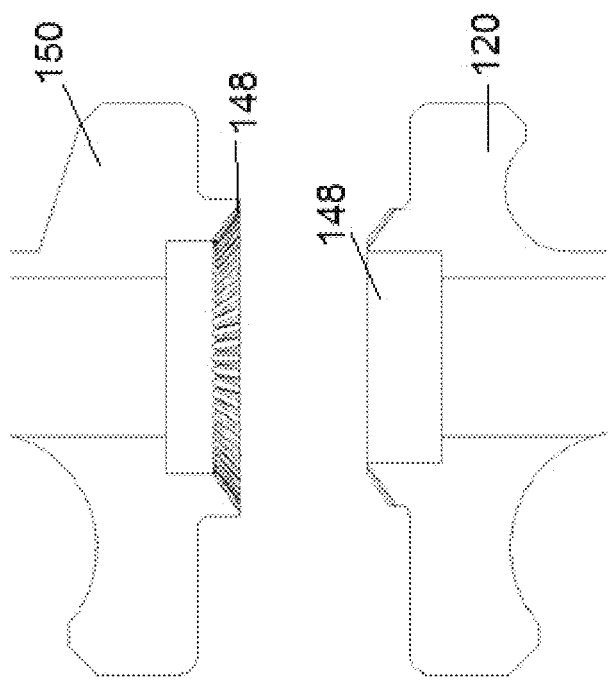
FIG. 16 shows a cross-sectional view of the first clamp assembly and the second clamp assembly of FIG. 15.

FIG. 16 shows a cross-sectional view of the first clamp assembly and the second clamp assembly of FIG. 15. From this view, one can see how the second clamp assembly 150 includes a toothed locking half 148 in the form of an internal beveled star grind. The beveled star grind of the second clamp assembly 150 engages the beveled star grind of the first clamp assembly 120, as noted above.

FIG. 17 is a close-up view of teeth of a toothed locking half in accordance with some embodiments. The teeth 147 of the toothed locking half 148 are arranged concentrically around an opening for receiving a shaft (e.g., shaft 110) of the clamp assembly 150, thereby forming a beveled star grind. In some embodiments, the teeth 147 are formed continuously around the opening, while in other embodiments, the teeth 147 are formed intermittently around the opening.

FIG. 18 is a close-up view of a first clamp assembly and a second clamp assembly in a fully tightened construct in accordance with some embodiments. In the fully tightened construct, the first clamp assembly 120 and the second clamp assembly 150 are engaged with one another such that their star grind components are not visible. Advantageously, the beveled star grinds will allow for the clamp assemblies to resist rotation relative to one another. In addition, they will also provide a strong consistent hold each time the clamp assemblies are tightened.

FIG. 19 is a side view of a rod to be used with any of the external fixators above in accordance with some embodiments. The rod 50 can be formed of a biocompatible material. In some embodiments, the rod 50 is formed of carbon fiber. In some embodiments, the rod 50 can be coated with an additional material to make it more compatible for MRI use.

Figure 20:
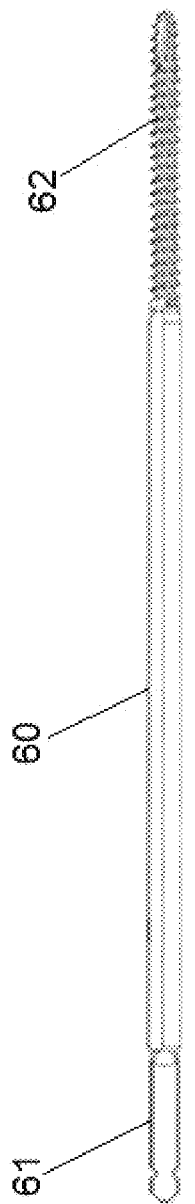
FIG. 20 is a side view of a pin in accordance with some embodiments.

FIG. 20 is a side view of a pin to be used with any of the external fixators above in accordance with some embodiments. The pin 60 can be comprised of a proximal portion 61 and a distal portion 62. The proximal portion 61 can comprise one or more grooves or features that allow for quick connection to a hand-held tool. In some embodiments, the proximal portion 61 comprises an AO quick connect adapter. The distal portion 62 can comprise one or more threads that can be inserted into bone. In some embodiments, two or more pins will be used with any of the external fixators described above. The pins that can be self-tapping and/or self-tapping/self-drilling pins. In some embodiments, the pins may have a coating, such as a hydroxyapatite coating in order to prevent pin tract infection. The length and diameter of the pins can vary depending on the patients and surgeon preference. In some embodiments, a pin is provided that can have grooves cut along its shank such that if the end of the pin is cut off, removal can still be easily achieved with another instrument (e.g., a keyless chuck). One skilled in the art that different types of pins can be used with any of the external fixators described above. For example, in some embodiments, two pins can be used with an external fixator whereby the first pin has an AO quick connect adapter, while the second pin does not have an AO quick connect adapter.

Figure 22:
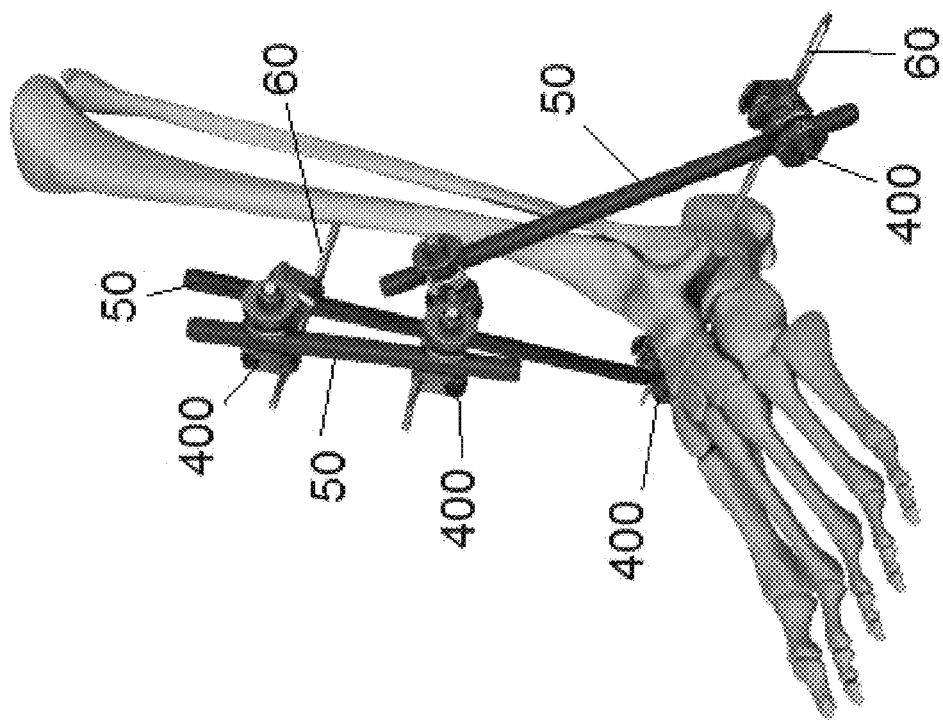
FIG. 22 is a front perspective view of several external fixator assemblies in operation with bones of a foot.
Figure 21:
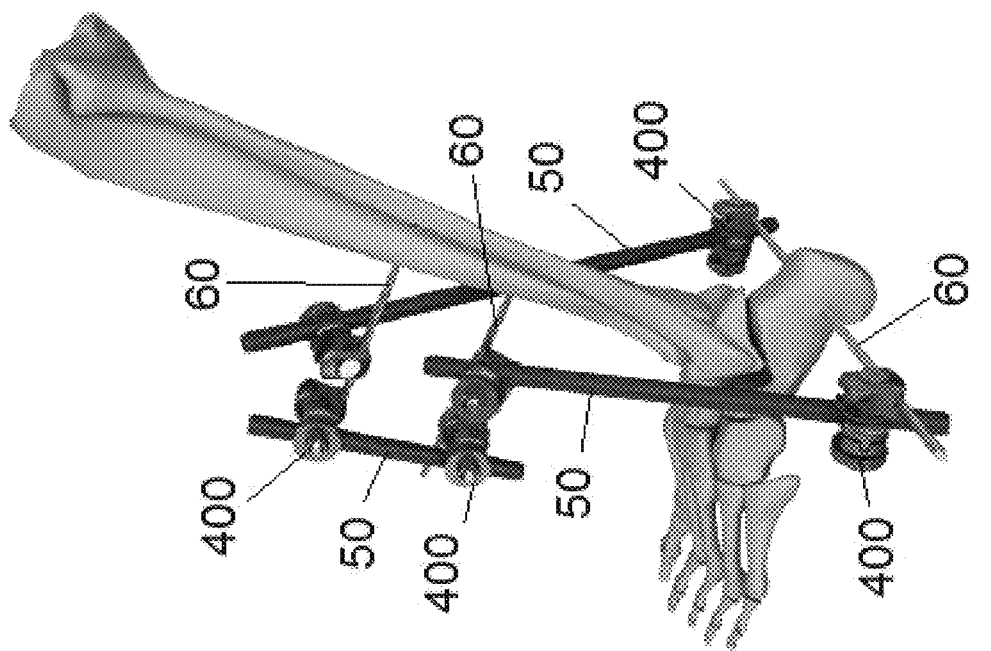
FIG. 21 is a rear perspective view of several external fixator assemblies in operation with bones of a foot.

FIG. 21 is a rear perspective view of several external fixator assemblies in operation with bones of a foot. FIG. 22 is a front perspective view of several external fixator assemblies in operation with bones of a foot. In these embodiments, one or more external fixator assemblies 400 are assembled with one or more rods 50 or pins 60 to stabilize the bones of a foot. In some embodiments, a pair of external fixator assemblies 400 receive one or more pins 60 therethrough that extend into a tibia bone 74. These external fixator assemblies 400 also receive one or more rods 50 that connect them to lower external fixator assemblies 400. These lower external fixator assemblies 400 include one or more pins 60 that extend into a calcaneus (or heel) bone 72. One skilled in the art will appreciate that the construct shown in FIGS. 21 and 22 is not limiting, and that the rods 50 and pins 60 can extend into other bones of the leg or foot, including the fibula, tarsals, metatarsals, and/or phalanges.

In some embodiments, one or more multi-pin clamps can be used with any of the external fixator assemblies disclosed above. The multi-pin clamps are configured to receive bone pins therethrough that engage with bone members. Advantageously, the multi-pin clamps accommodate constructs that would otherwise require even more external fixator assemblies, thereby making an overall system less bulky to a patient.

FIG. 23 is a perspective view of a multi-pin clamp in use. The multi-pin clamp 500 is configured to be used with one or more external fixator assemblies 400 (four in the present embodiment) to create a construct that is ideal for specific patients. Advantageously, the multi-pin clamp 500 helps to reduce the number of external fixator assemblies 400 in the overall system, thereby making it less bulky.

As shown in FIG. 23, the multi-pin clamp 500 comprises a first vise plate 512 and a second vise plate 514 capable of receiving one or more pins 60 therethrough. The pins 60 through the multi-pin clamp 500 are capable of engaging one or more bone members. In the present embodiment, the pins 60 engage a tibia 74. In addition, the multi-pin clamp 500 further comprises a pair of angled posts 532, 534. The angled posts 532, 534 are each capable of being received in an external fixator assembly 400. Each of these external fixator assemblies is also capable of receiving a rod 50 that is attached to lower external fixator assemblies 400. The lower external fixator assemblies 400 each include a pin 60 therethrough capable of engaging one or more bone members. In the present embodiment, the lower pins 60 engage a calcaneus or heel bone. While the multi-pin clamp 500 is shown in use with one or more external fixator assemblies 400 as shown in FIG. 13, one skilled in the art will appreciate that the multi-pin clamp 500 can be used with any of the external fixator assemblies described herein.

Figure 24:
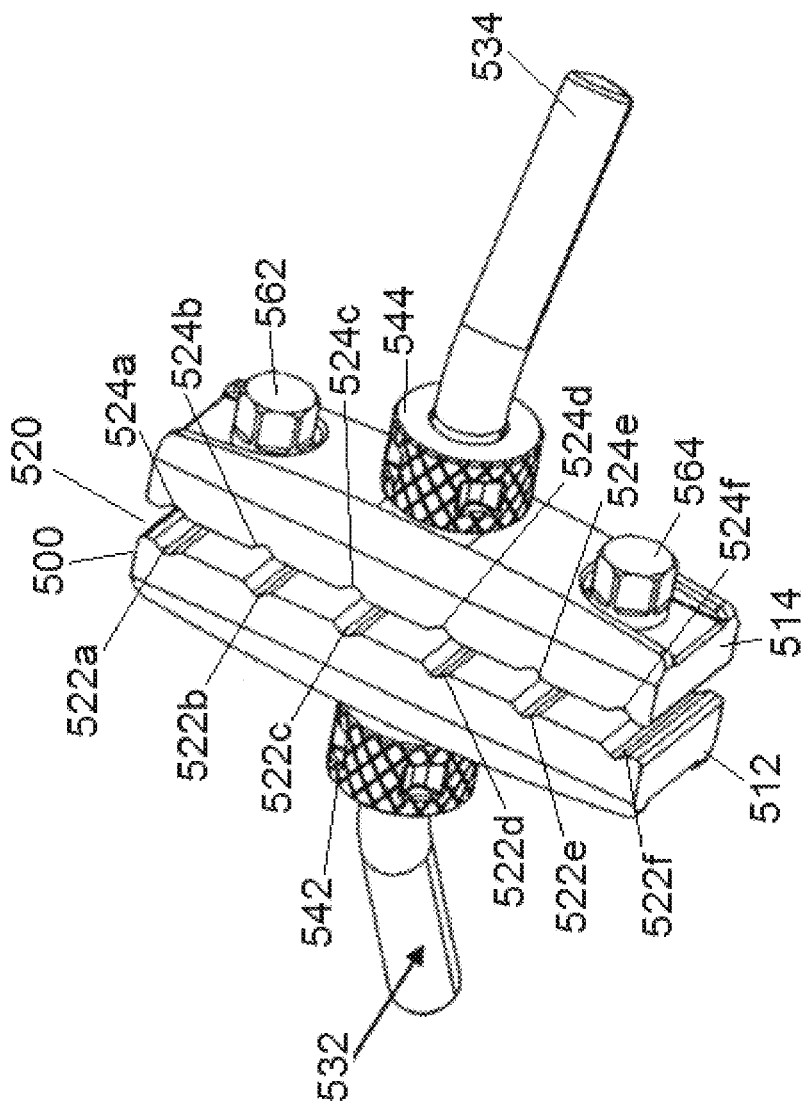
FIG. 24 is a top perspective view of a multi-pin clamp in accordance with some embodiments.

FIG. 24 is a top perspective view of a multi-pin clamp in accordance with some embodiments. The multi-pin clamp 500 comprises a first vise plate 512, a second vise plate 514, a first angled post 532 connected to the first vise plate 512 via a first retention nut 542, and a second angled post 534 connected to the second vise plate 514 via a second retention nut 544. The multi-pin clamp 500 is configured to receive one or more pins 60 through a channel 520 formed between the first vise plate 512 and the second vise plate 514. When the one or more pins 60 are inserted through the channel 520, the channel 520 can be narrowed by bringing the first vise plate 512 and second vise plate 514 closer to one another. The first vise plate 512 and second vise plate 514 can be brought closer together via first and second tightening bolts 562, 564.

As shown in FIG. 24, the multi-pin clamp 500 utilizes a pair of vise plates 512, 514 to receive one or more pins 60 therein. In some embodiments, the first vise plate 512 is a mirror image of the second vise plate 514. As shown in FIG. 24, the first vise plate 512 is parallel or substantially parallel to the second vise plate 514. In other embodiments, the first vise plate 512 is at a non-parallel angle relative to the second vise plate 514. The vise plates 512, 514 in combination form a channel 520 therebetween for receiving one or more pins 60 therein.

In some embodiments, the first vise plate 512 can include one or more grooves 522 formed along an inner wall. As shown in FIG. 24, the first vise plate 512 includes grooves 522a, 522b, 522c, 522d, 522e, and 522f. In addition, the second vise plate 514 can include one or more corresponding grooves 524 formed along an inner wall. As shown in FIG. 24, the second vise plate 514 includes grooves 524a, 524b, 524c, 524d, 524e, and 524f. Advantageously, the grooves 522, 524 provide spaced apart receiving surfaces for receiving one or more pins 60 therein. When the one or more pins 60 are compressed by the vise plates 512, 514, the vise plates 512, 514 advantageously provide at least four lines of contact one each pin 60, thereby ensuring a firm grasp and stable construct.

When one or more pins 60 are received within the channel 520, the channel 520 can be narrowed by rotating tightening bolts 562, 564. Advantageously, the tightening bolts 562, 564 are provided in different areas of the multi-pin clamp 500. For example, tightening bolt 562 is on an upper portion of the multi-pin clamp 500, while tightening bolt 564 is on a lower portion of the multi-pin clamp 500. This allows each of the tightening bolts 562, 564 to be controlled independently, and to allow a tighter clamping if desired on one part of the multi-pin clamp 500 relative to another part. In some embodiments, the multi-pin clamp 500 can comprise a single tightening bolt. In other embodiments, three or more tightening bolts can be provided. On skilled in the art will appreciate that rotation of the tightening bolts 562, 564 in a first direction causes the channel 520 to narrow onto one or more pins 60, while rotation of the tightening bolts 562, 564 in a second direction opposite the first causes the channel 520 to widen, thereby releasing one or more pins 60.

In some embodiments, the multi-pin clamp 500 further includes a first angled post 532 and a second angled post 534. The first angled post 532 extends outwardly from the first vise plate 512, while the second angled post 534 extends outwardly from the second vise plate 514. Each of these posts 532, 534 is capable of being received in a clamp of an external fixator assembly (as shown in FIG. 23), thereby creating a secure construct. In some embodiments, only one of the posts 532, 534 is angled, while the other can be straight. In some embodiments, both of the posts 532, 534 are straight.

Figure 25:
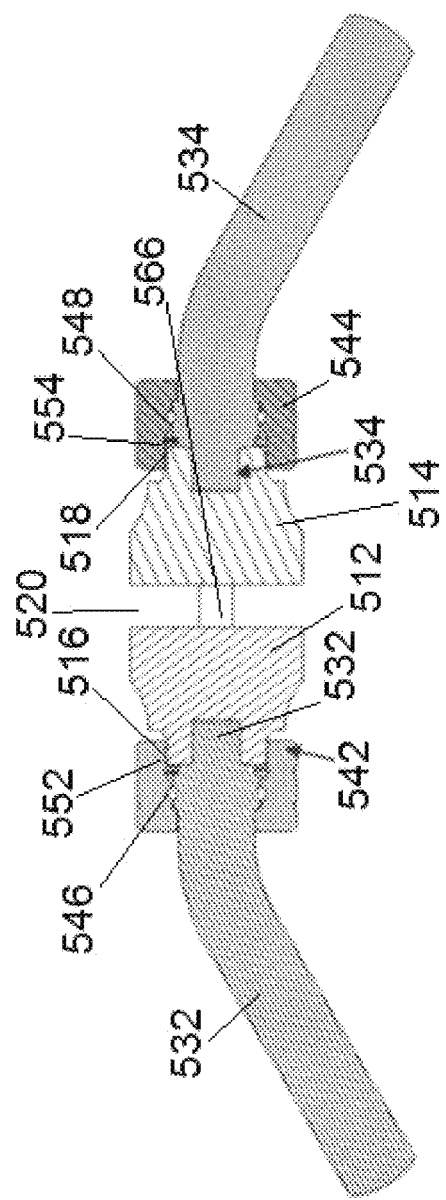
FIG. 25 is a cross-sectional view of the multi-pin clamp of FIG. 24.

As shown in FIG. 24, the first angled post 532 is connected to a first retention nut 542. Likewise, the second angled post 534 is connected to a second retention nut 544. The retention nuts 542, 544 may serve to secure the angled posts 532, 534 to their respective vise plates 512, 514. In some embodiments, the angled posts 532, 534 can be secured to their respective retention nuts 542, 544 via retaining rings 546, 548 (shown in FIG. 25). In other embodiments, the angled posts 532, 534 can be secured to their respective retention nuts 542, 544 via an interference or snap fit. And in yet other embodiments, the angled posts 532, 534 can be welded to a respective retention nut 542, 544, or directly to a respective vise plate 512, 514. As shown in FIG. 25, the first retention nut 542 can be threadingly attached to the first vise plate 512, while the second retention nut 544 can be threadingly attached to the second vise plate 514.

FIG. 25 is a cross-sectional view of the multi-pin clamp of FIG. 24. From this cross-sectional view, one can see how the first angled post 532 is attached to the first retention nut 542 via a first retaining ring 546, while second angled post 534 is attached to the second retention nut 544 via a second retaining ring 548. The first retention nut 542 can comprise inner threads 552 that engage with outer threads 516 of the first vise plate 512, thereby securing the first angled post 532 thereto. Likewise, the second retention nut 544 can comprise inner threads 554 that engage with outer threads 518 of the second vise plate 514, thereby securing the second angled post 534 thereto. In some embodiments, the angled posts 532, 534 can be preassembled to their respective retention nuts 542, 544 before attaching to the retention nuts 542, 544 to their respective vise plates 512, 514.

As shown in FIG. 25, the vise plates 512, 514 form a channel 520 for receiving one or more pins therethrough. One or more tightening bolts 562, 564 (shown in FIG. 24) are used to bring the vise plates 512, 514 together via rotation. From the view in FIG. 25, one can see a bolt shaft 566 of one of the tightening bolts 562, which extends across the channel 520 to connect the vise plates 512, 514.

Figure 27:
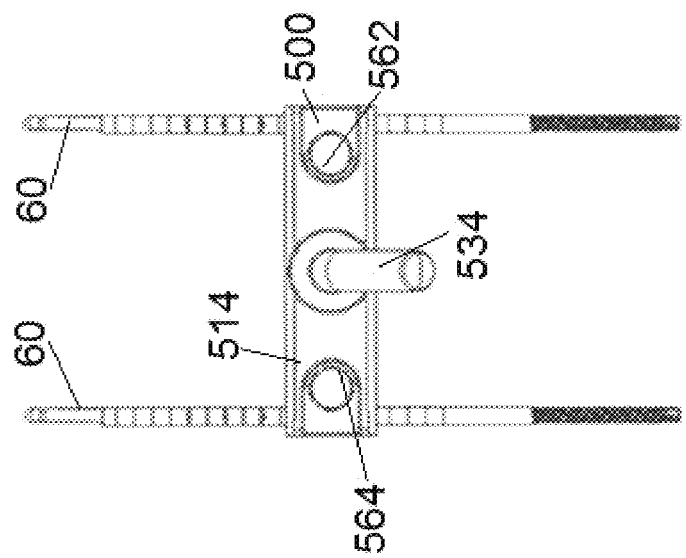
FIG. 27 is a side view of the multi-pin clamp of FIG. 26 with the drill sleeves removed.
Figure 26:
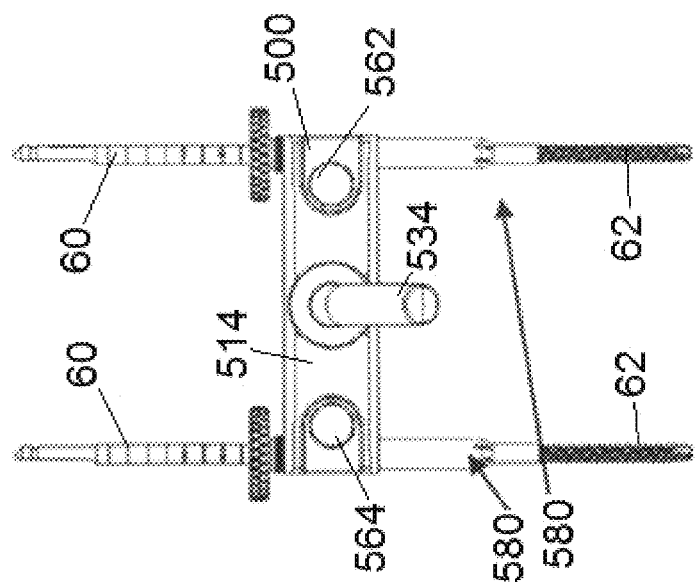
FIG. 26 is a side view of the multi-pin clamp of FIG. 24 having drill sleeves and used as a drill guide.

In some embodiments, the multi-pin clamp 500 can itself be used as a drill guide to guide pins into bone. FIGS. 26 and 27 show how the multi-pin clamp 500 can be used as a drill guide.

FIG. 26 is a side view of the multi-pin clamp of FIG. 24 having drill sleeves and operating as a drill guide. The multi-pin clamp 500 is capable of receiving one or more drill sleeves 580 prior to inserting pins therethrough. Each of the one or more drill sleeves 580 can be a tubular member having an inner lumen for receiving a pin therein. One or more pins 60 can then be guided into bone using the drill sleeves 580 as guides. Once the pins 60 are properly positioned, the drill sleeves 580 can be removed from the multi-pin clamp 500, and the multi-pin clamp 500 can be tightened onto the one or more pins 60.

FIG. 27 is a side view of the multi-pin clamp of FIG. 26 with the drill sleeves removed. With the drill sleeves 580 removed, the vise plates 512, 514 can clamp down on the one or more pins 60 via rotation of the tightening bolts 562, 564.

FIG. 28 is a perspective view of an alternative multi-pin clamp in use. The alternative multi-pin clamp 600 comprises a body 620 for receiving one or more pins 60 therein. The body 620 houses an internal sliding member 660 (shown in FIG. 31) that can translate via a tightening nut 628, thereby advantageously providing a one-step locking mechanism, as will be discussed in greater detail below. The multi-pin clamp comprises a first angled post 632 connected to a first retention nut 642 and a second angled post 634 connected to a second retention nut 644. The first angled post 632 is connected to a first outer sidewall of the multi-pin clamp 600, while the second angled post 634 is connected to a second outer sidewall of the multi-pin clamp 600. The rest of the construct is comparable to that shown in FIG. 23, and includes several external fixator assemblies 400, pins 60 and rods 50.

FIG. 29 is a top perspective view of an alternative multi-pin clamp having an internal sliding member in accordance with some embodiments. The multi-pin clamp 600 comprises a body 650 having a first outer sidewall 624, a second outer sidewall 626, and a series of openings or holes 622 for receiving one or more pins 60 formed therebetween. The multi-pin clamp 600 further comprises a first angled post 632 that is attached to the first outer sidewall 624 via a first retention nut 642 and a second angled post 634 that is attached to the second outer sidewall 626 via a second retention nut 644.

As shown in FIG. 29, the multi-pin clamp 600 comprises a body 620 having a first outer sidewall 624 and a second outer sidewall 626. The body 620 is substantially enclosed, and includes one or more openings 622 for receiving one or more pins 620 therethrough. In some embodiments, the body 620 comprises openings 622a, 622b, 622c, 622d, 622e, and 622f, each of which is capable of receiving a pin 60 therethrough. In some embodiments, the openings 622 are rounded, while in other embodiments, the openings 622 are non-rounded. In some embodiments, the openings 622 are evenly spaced from one another, while in other embodiments, the spacing between the openings 622 can vary.

The body 620 of the multi-pin clamp 600 encloses an internal sliding member 660 (shown in FIG. 31). The sliding member 660 includes one or more holes or openings 662 that correspond with the openings 622 of the body 620. When the openings 662 of the internal sliding member 660 are aligned with the openings 622 of the body 620, bone pins 60 can be received therethrough. Once the bone pins 60 are received therethrough, a tightening nut 628 that is attached to the body 620 can be rotated. Rotation of the tightening nut 628 causes the internal sliding member 660 to translate within the body 620, thereby causing the openings 662 of the internal sliding member 660 to misalign with the openings 622 of the body 620. This misalignment causes a bone pin 60 to be clamped between an opening 662 of the internal sliding member 660 and an opening 622 of the body 620, thereby securing the bone pin 60 therein. Advantageously, the multi-pin clamp 600 can tighten on one or more bone pins 60 received therein via a single rotation of the tightening nut 628, thereby providing a one-step locking mechanism. Reverse rotation of the tightening nut 628 can cause the openings 662 of the internal sliding member 660 to align with the openings 622 of the body 620, thereby untightening the clamp on the one or more pins.

In some embodiments, the multi-pin clamp 600 further includes a first angled post 632 and a second angled post 634. The first angled post 632 extends outwardly from a first outer sidewall 624 of the body 620, while the second angled post 634 extends outwardly from a second outer sidewall 626 of the body 620. Each of these posts 632, 634 is capable of being received in a clamp of an external fixator assembly (as shown in FIG. 28), thereby creating a secure construct. In some embodiments, only one of the posts 632, 634 is angled, while the other can be straight. In some embodiments, both of the posts 632, 634 are straight.

As shown in FIG. 29, the first angled post 632 is connected to a first retention nut 642. Likewise, the second angled post 634 is connected to a second retention nut 644. The retention nuts 642, 644 serve to secure the angled posts 632, 634 to their respective sidewalls 624, 626. In some embodiments, the angled posts 632, 634 can be secured to their respective retention nuts 642, 644 via retaining rings 646, 648 (shown in FIG. 31). In other embodiments, the angled posts 632, 634 can be secured to their respective retention nuts 642, 644 via an interference or snap fit. And in yet other embodiments, the angled posts 632, 634 can be welded to a respective retention nut 642, 644, or directly to a respective outer sidewall 624, 626 of the body 620. As shown in FIG. 31, the first retention nut 642 can be threadingly attached to the first outer sidewall 624, while the second retention nut 644 can be threadingly attached to the second outer sidewall 626.

FIG. 30 is a top cross-sectional view of the multi-pin clamp of FIG. 29. From this cross-sectional view, one can see how the first angled post 632 is attached to the first retention nut 642 via a first retaining ring 646, while second angled post 634 is attached to the second retention nut 644 via a second retaining ring 648. The first retention nut 642 can comprise inner threads 652 that engage with outer threads 616 of the first outer sidewall of the body 620, thereby securing the first angled post 632 thereto. Likewise, the second retention nut 644 can comprise inner threads 654 that engage with outer threads 618 of the second outer sidewall of the body 620, thereby securing the second angled post 634 thereto. In some embodiments, the angled posts 632, 634 can be preassembled to their respective retention nuts 642, 644 before attaching to the retention nuts 642, 644 to their sidewalls.

FIG. 31 is a front cross-sectional view of the multi-pin clamp of FIG. 29. From this view, one can see the internal sliding member 660 that is received in the body 620 of the multi-pin clamp 600. The internal sliding member 660 comprises a plurality of holes or openings 662a, 662b, 662c, 662d, 662e, and 662f for receiving one or more bone pins 60 therein. The internal sliding member 660 further includes a first end and a second end, wherein the first end comprises a threaded post 668. The threaded post 668 is configured to extend through an opening in the body 620 and threadingly engage internal threads 664 of the tightening nut 628.

Figure 32:
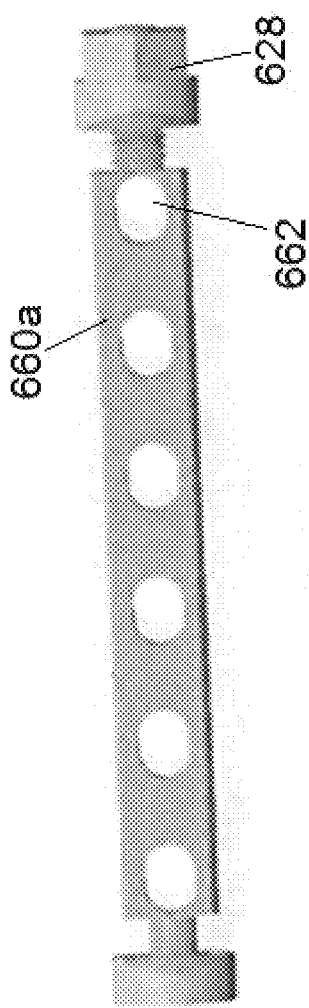
FIG. 32 is a top view of one version of an internal sliding member in accordance with some embodiments.

FIG. 32 is a top view of one version of an internal sliding member in accordance with some embodiments. The internal sliding member 660a is capable of being received within the body 620 of the multi-pin clamp 600. The internal sliding member 660a comprises an elongate body including a plurality of openings 662 therethrough. The openings in the present embodiment are oval shaped. Translation of the internal sliding member 660a can be controlled via rotation of the locking nut 628.

Figure 33:
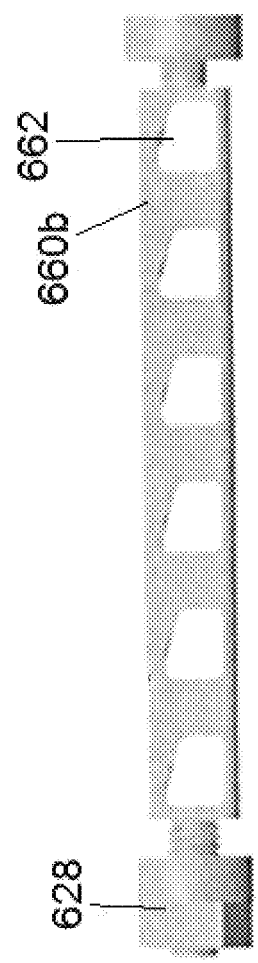
FIG. 33 is a top view of a second version of an internal sliding member in accordance with some embodiments.

FIG. 33 is a top view of a second version of an internal sliding member in accordance with some embodiments. The internal sliding member 660b is capable of being received within the body 620 of the multi-pin clamp 600. The internal sliding member 660a comprises an elongate body including a plurality of openings 662 therethrough. The openings in the present embodiment are non-symmetrical and have angled or ramped features. In some embodiments, the ramped features help to induce earlier compression on one or more pins 60 received in the internal sliding member 660b. Translation of the internal sliding member 660b can be controlled via rotation of the locking nut 628.

Figure 34:
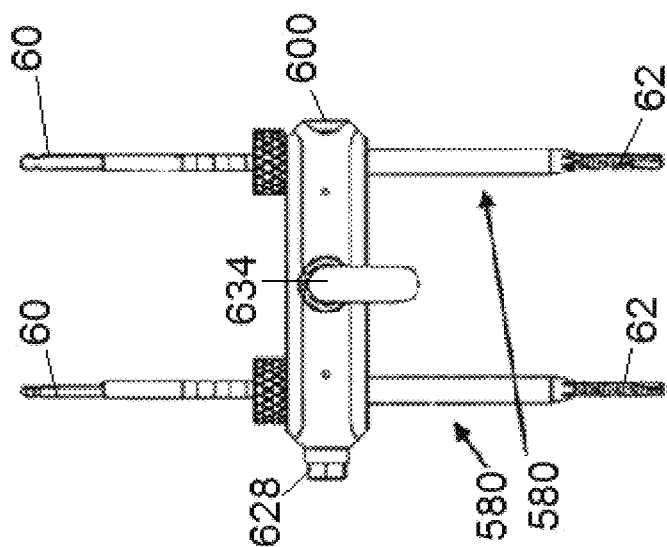
FIG. 34 is a side view of the multi-pin clamp of FIG. 29 having drill sleeves and used as a drill guide.

FIG. 34 is a side view of the multi-pin clamp of FIG. 29 having drill sleeves and operating as a drill guide. The multi-pin clamp 600 is capable of receiving one or more drill sleeves 580 prior to inserting pins therethrough. Each of the one or more drill sleeves 580 can be a tubular member having an inner lumen for receiving a pin therein. One or more pins 60 can then be guided into bone using the drill sleeves 580 as guides. Once the pins 60 are properly positioned, the drill sleeves 580 can be removed from the multi-pin clamp 600, and the multi-pin clamp 600 can be tightened onto the one or more pins 60.

Figure 35:
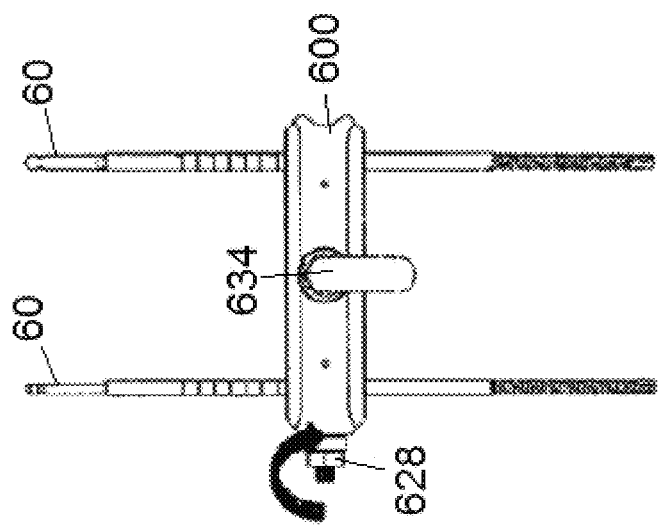
FIG. 35 is a side view of the multi-pin clamp of FIG. 34 with the drill sleeves removed.

FIG. 35 is a side view of the multi-pin clamp of FIG. 34 with the drill sleeves removed. With the drill sleeves 580 removed, the internal sliding member 660 can be translated via rotation of the tightening nut 628, thereby clamping down on the one or more pins 60 received therein.

Figure 36:
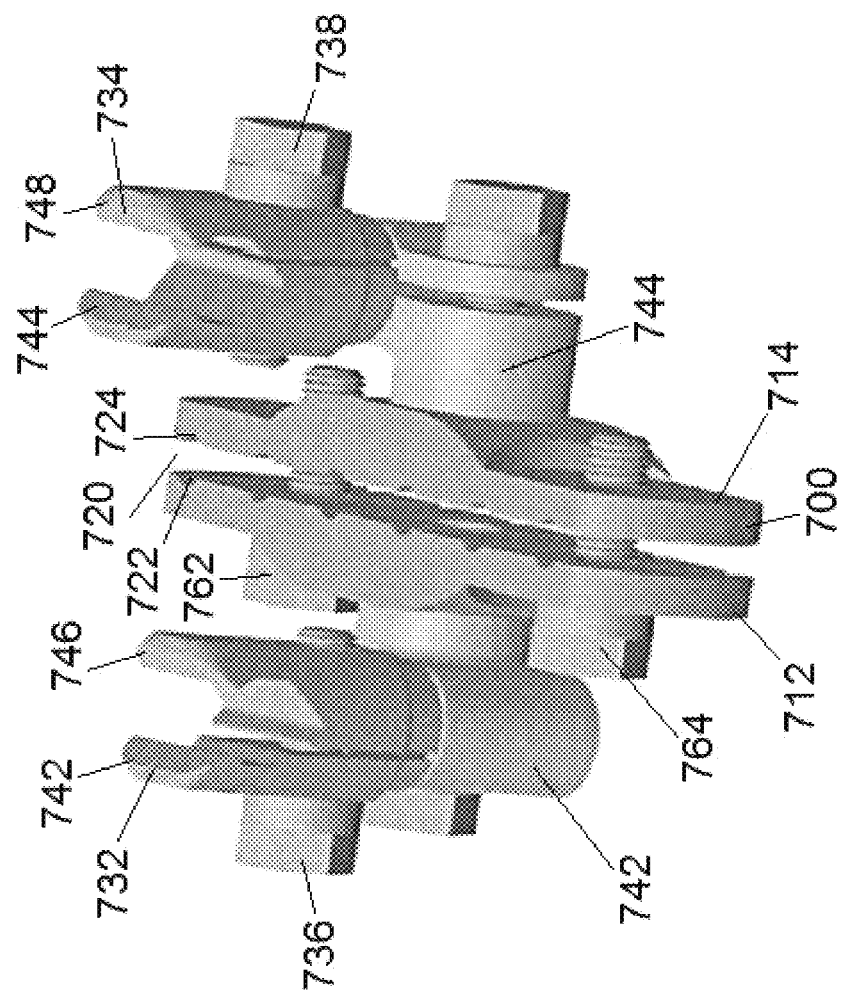
FIG. 36 is a top perspective view of an alternative multi-pin clamp attached to integrated clamps in accordance with some embodiments.

FIG. 36 is a top perspective view of an alternative multi-pin clamp attached to integrated clamps in accordance with some embodiments. Like the multi-pin clamp in FIG. 24, the multi-pin clamp 700 comprises a first vise plate 712, a second vise plate 714, a channel 720 formed between the first vise plate and second vise plate, and a pair of tightening bolts 762, 764 for narrowing the width of the channel 720. However, in the present embodiment, the multi-pin clamp 700 further includes a first joint 742 and a second joint 744, wherein the first joint 742 is attached to a first U-shaped clamp 732 and the second joint 744 is attached to a second U-shaped clamp 734.

The first joint 742 can be attached to the first vise plate 712 via threading, interference fit, or welding. A U-shaped clamp 732 extends upwardly from the first joint 742. The U-shaped clamp 732 comprises a first jaw 742 and a second jaw 746 that form a channel for receiving a rod or pin therein. The jaws 742, 746 can be controlled via a clamp bolt 736. The second joint 744 can be attached to the second vise plate 714 via threading, interference fit, or welding. A U-shaped clamp 734 extends upwardly from the second joint 744. The U-shaped clamp 734 comprises a first jaw 744 and a second jaw 748 that form a channel for receiving a rod or pin therein. The jaws 742, 746 can be controlled via a clamp bolt 738.

Figure 37:
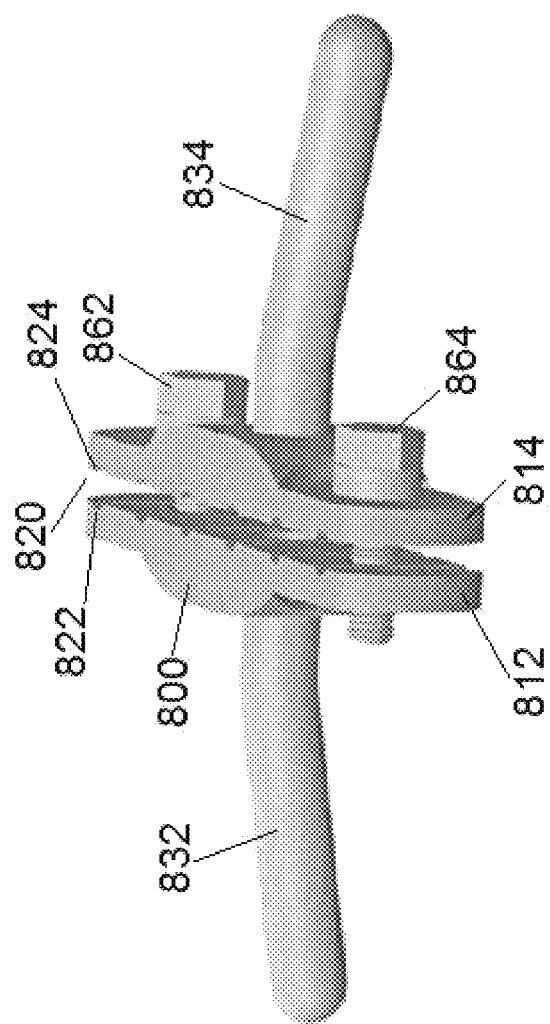
FIG. 37 is a top perspective view of an alternative multi-pin clamp with angled rods in accordance with some embodiments.

FIG. 37 is a top perspective view of an alternative multi-pin clamp with angled rods in accordance with some embodiments. Like the multi-pin clamp in FIG. 24, the multi-pin clamp 800 comprises a first vise plate 812, a second vise plate 814, a channel 820 formed between the first vise plate and second vise plate, and a pair of tightening bolts 862, 864 for narrowing the width of the channel 820. However, in the present embodiment, the multi-pin clamp 800 further includes a first angled bar or rod 832 and a second angled bar or rod 834, each of which is directly connected to respective first and second vise plates. In some embodiments, the angled bars 832, 834 can be welded, press fit or threaded onto respective first and second vise plates. In some embodiments, each of the angled bars 832, 834 can be received in a clamp (e.g., in an external fixator assembly), thereby forming a secure construct.

Figure 38:
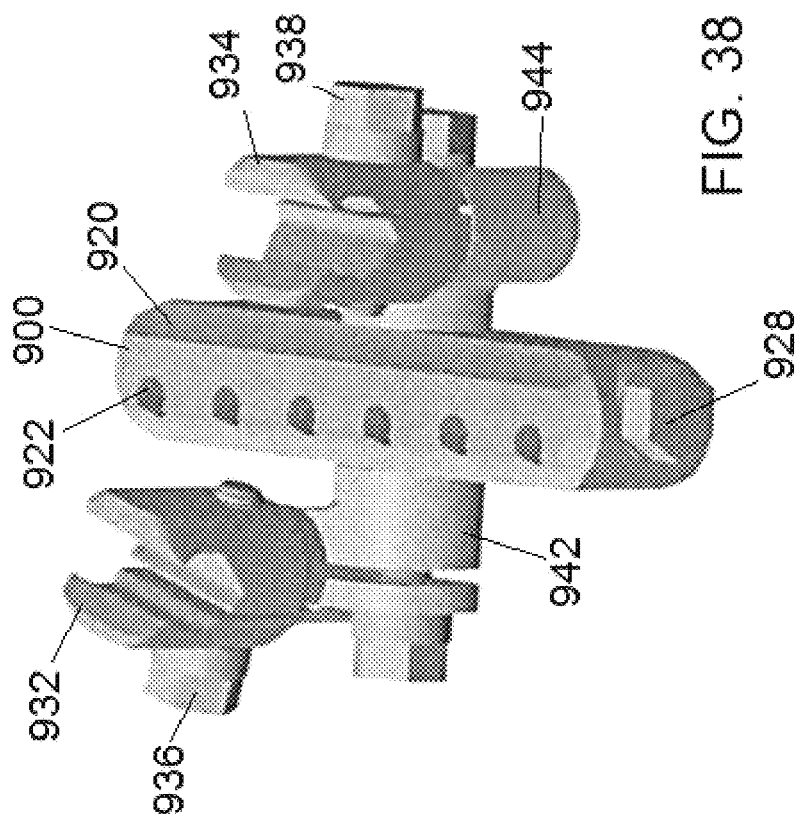
FIG. 38 is a top perspective view of an alternative multi-pin clamp with offset tightening nut in accordance with some embodiments.

FIG. 38 is a top perspective view of an alternative multi-pin clamp with offset tightening nut in accordance with some embodiments. Like the multi-pin clamp in FIG. 29, the multi-pin clamp 900 comprises a body 920 including openings 922 for receiving one or more bone pins 60 therein. The body 920 encloses a moveable internal member 960 that can be controlled by a tightening nut 928. In the present embodiment, the tightening nut 928 is offset from a central longitudinal axis of the body 920. In contrast to the multi-pin clamp in FIG. 29 in which the internal sliding member translates vertically along a longitudinal axis of the body, in the present embodiment, the moveable internal member 960 rotates. As the internal member 960 rotates, one or more cams 926 formed along the moveable internal member 960 engage bone pins 60 received in the body 920, thereby securing the bone pins 60 therein.

As shown in FIG. 38, the body 920 of the multi-pin clamp 900 is attached to a pair of joints 942, 944, one on each sidewall of the body 920. The first joint 942 is attached to a first U-shaped clamp 932 having a pair of jaws that are operated via a first clamp bolt 936. The second joint 944 is attached to a second U-shaped clamp 934 having a pair of jaws that are operated via a second clamp bolt 938.

FIG. 39 is a top cross-sectional view of the multi-pin clamp of FIG. 38 including cam in accordance with some embodiments. From this view, one can see an inner cam 926 of the moveable internal member 960, which is configured to engage a bone pin 60 upon rotation of the moveable internal member 960. The offset tightening nut 928 (shown in FIG. 38) provides a unique means to secure one or more bone pins 60 within a body 920 of the multi-pin clamp 900.

To assist in assembling the external fixator assemblies, one or more tools can be provided. These tools can be used to perform one or more of the following functions: (i) initial tightening of a cap or ratchet assembly of an external fixator assembly; (ii) final tightening of a cap or ratchet assembly of an external fixator assembly; and (iii) advancement or installation of one or more bone pins in an external fixator assembly. In some embodiments, multiple instruments (e.g., three) can be used to perform each of these functions. However, it can be burdensome to carry and exchange one instrument for another. Accordingly, the multi-purpose instrument may perform each of the three functions described above. This multi-purpose instrument includes features that can accommodate each of the three functions described herein, thereby reducing the number of instruments in a kit.

FIG. 40 shows a multi-purpose tool or instrument performing three different functions in accordance with some embodiments. The multi-purpose instrument 1000 is capable of performing multiple functions, including (1) initial tightening of a cap or ratchet assembly 470 of an external fixator assembly 400; (2) final tightening of a cap or ratchet assembly 470 of an external fixator assembly 400; and (3) advancement or installation of one or more bone pins 60 in an external fixator assembly. These functions are discussed below.

First, the multi-purpose instrument 1000 can be used for initial tightening of a cap or ratchet assembly 470 of an external fixator assembly 400. After a pin 60 or rod 50 is received and provisionally held within the external fixator assembly 400, a distal end of the multi-purpose instrument can engage a nut of the cap or ratchet assembly 470 to cause rotation of the cap or ratchet assembly 470. This rotation causes the clamps of the first clamp assembly 420 and the second clamp assembly 450 to compress and tighten on any pin 60 or rod 50 held in the external fixator assembly 400.

Second, the multi-purpose instrument 1000 can be used for final tightening of a cap or ratchet assembly 470 of an external fixator assembly. Following the initial tightening, it may be desirable to further tighten the cap or ratchet assembly 470 via rotation of the nut. The multi-purpose instrument 1000 can be oriented such that a wrench portion 1020 (shown in FIG. 41) is capable of tightening the nut of the cap or ratchet assembly 470 further. This helps to provide further compression to any pin 60 or rod 50 that is held in the external fixator assembly 400.

Third, the multi-purpose instrument 1000 can be used to advance or install one or more bone pins 60 in an external fixator assembly. As shown in FIG. 40, a distal end of the multi-purpose instrument 1000 is configured to engage an end of the bone pin 60 (e.g., via an AO connect). The multi-purpose instrument 1000 is then able to translate and/or rotate the bone pin 60, such that it is moveable relative to the external fixator assembly 400. The multi-purpose instrument 1000 is capable of installing a bone pin 60 within the external fixator assembly 400 and/or moving a bone pin 60 that is already received within the external fixator assembly 400.

FIG. 41 is a top perspective view of a multi-purpose instrument in accordance with some embodiments. The multi-purpose instrument 1000 comprises a proximal portion and a distal portion. The proximal portion includes a handle 1010. The distal portion includes a nut driver 1020, a wrench portion 1030, and an AO drive adapter 1040. Each of these features may help to perform one of the three functions discussed above.

The nut driver 1020 comprises a driver on a distal end of the multi-purpose instrument 1000. As shown in FIG. 41, the nut driver 1020 can be in the shape of a hex driver or any other suitable driver capable of turning a nut of the cap or ratchet assembly 470. The nut driver 1020 is capable of initially tightening a nut of the cap or ratchet assembly 470. The multi-purpose instrument 1000 can attach to the nut, whereby the instrument can be rotated axially to accomplish the initial tightening.

The wrench portion 1030 comprises a wrench between the proximal and distal end of the multi-purpose instrument 1000. The wrench portion 1030 is further capable of turning a nut on the cap or ratchet assembly 470 to further tighten the clamps of the externa fixator assembly 400.

The AO drive adapter 1040 comprises an inner lumen that is formed proximally relative to the nut driver 1020. The adapter 1040 (shown best in FIG. 43) is capable of receiving and connecting to a pin 60 therein. Axial rotation of the driver causes a pin 60 in the adapter 1040 to translate and/or rotate relative to the clamps of the external fixator assembly.

FIG. 42 is a front view of the multi-purpose instrument of FIG. 41. From this view, one can see the contours of the nut driver 1020 and the inner AO drive adapter 1040. The contours are of different shapes to accommodate different components. In the present embodiment, the nut driver 1020 is contoured to accommodate a hex nut of the cap or ratchet assembly 470, while the inner AO drive adapter 1040 is partially rounded and partially flat to accommodate an AO connect of a pin 60.

Figure 43:
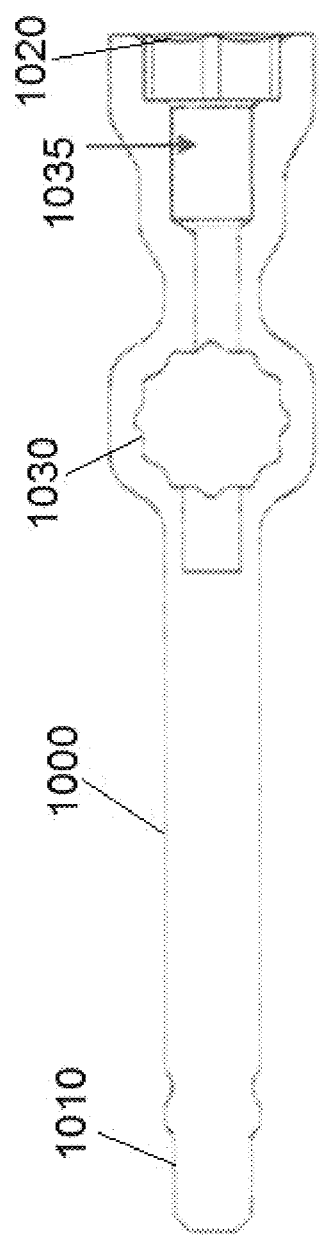
FIG. 43 is a side cross-sectional view of the multi-purpose instrument of FIG. 41.

FIG. 43 is a side cross-sectional view of the multi-purpose instrument of FIG. 41. From this view, one can see all three of the features described above, including the nut driver 1020, the AO drive adapter 1040, and the wrench portion 1030. The nut driver 1020 is connected to the AO drive adapter 1040 via a clearance lumen 1035.

Figure 44:
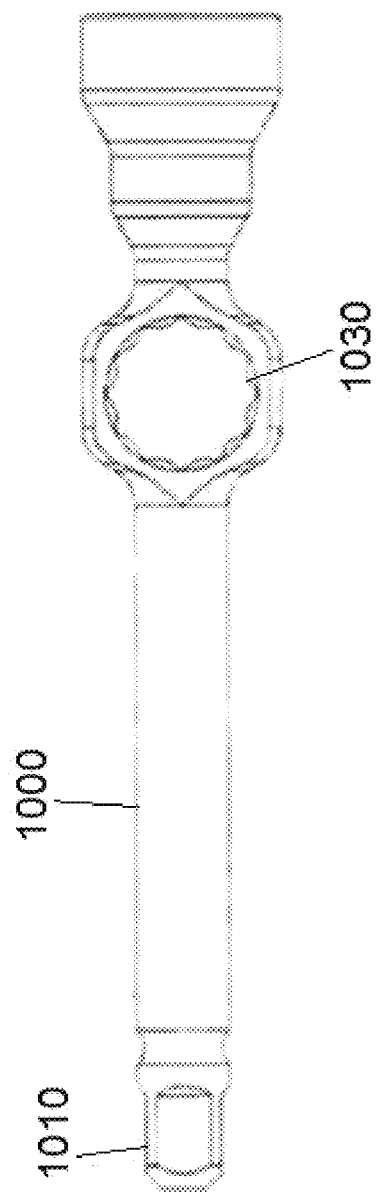
FIG. 44 is a side view of the multi-purpose instrument of FIG. 41.
Figure 45:
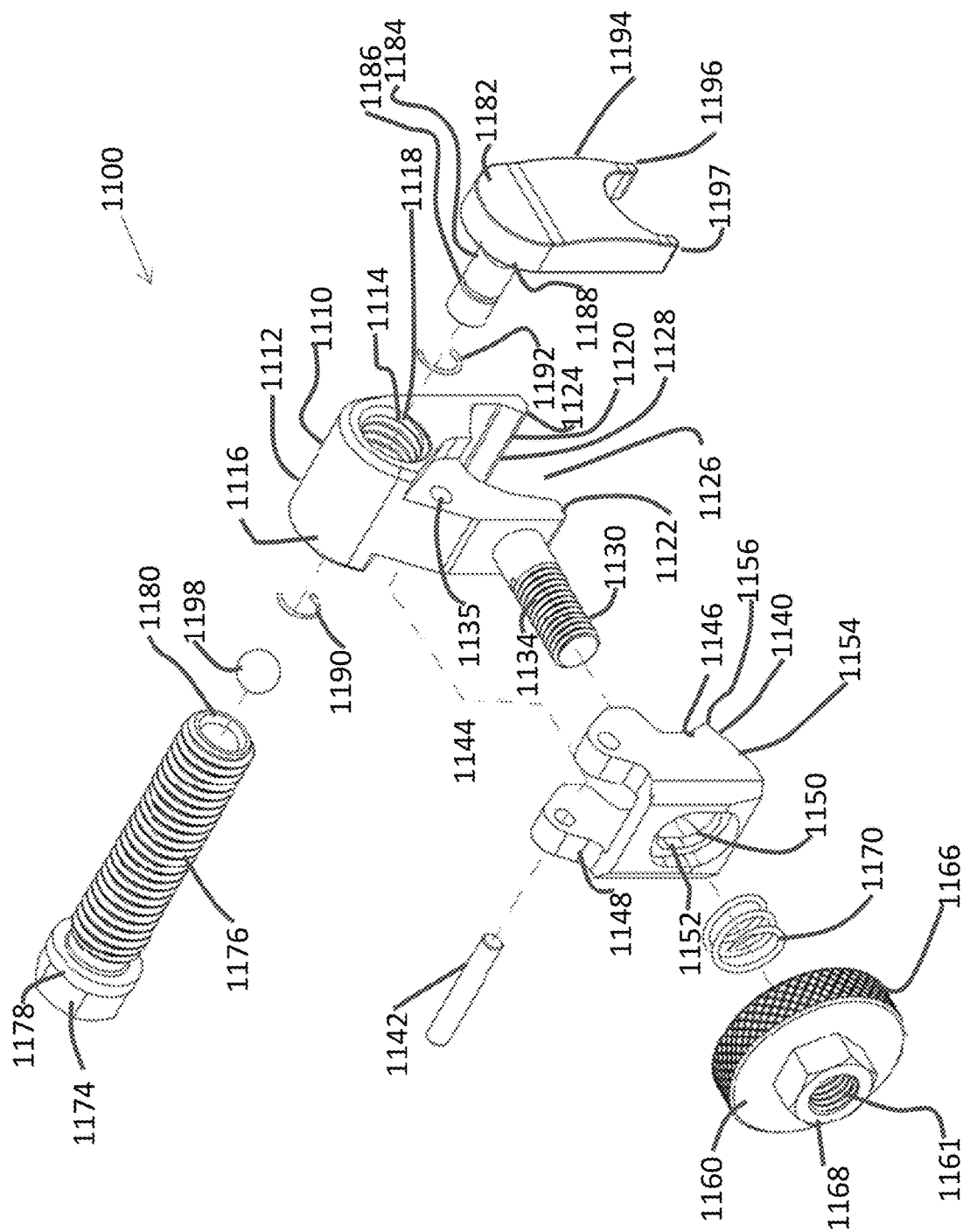
FIG. 45 is an exploded view of an exemplary embodiment of a compression/distractor instrument.

FIG. 44 is a side view of the multi-purpose instrument of FIG. 41. From this view, one can see the outer surface of the multi-purpose instrument 1000, which includes a wrench portion 1030.

FIGS. 45-52 show another exemplary embodiment of a distraction/compression instrument 1100 ("instrument 1100"). Typical distractor/compressor designs must be placed onto a construct and then tightened into place. The instrument 1110 allows for the distractor to be snapped onto the construct and remain in position. The instrument 1110 can then be tightened to remain rigidly affixed while in use.

The instrument 1100 improves attachment to a construct by integrating a snap-on mechanism and can be attached to a construct, such as rod 50, with one hand for easy repositioning. Final tightening can be achieved with a single hand tool (not shown). The instrument 1100 is used to adjust the location of a clamp 90 (shown in FIGS. 48 and 49) along the length of the rod 50.

The instrument 1100 includes a generally U-shaped frame 1110 having a superior connector portion 1112 that includes a female threaded through-passage 1114 extending therethrough. The through-passage 1114 has a first end 1116 and a second end 1118. An inferior portion 1120 includes a first leg 1122 and a second leg 1124 extending from the superior connector portion 1112. The first leg 1122 extends inwardly from the superior portion 1112 and has a first width. The second leg 1124 has a width that is generally the same size as the length of the through-passage 1114. A rod passage 1126 is formed between the first leg 1122 and the second leg 1124. The rod passage 1124 is provided to receive and retain the rod 50. The second leg 1124 includes a tip 1128 that extends into the rod passage 1126.

The first leg 1122 includes a stud 1130 extending outwardly from the first leg 1122, away from the second leg 1124 and transverse relative to the through-passage 1114. The stud 1130 has a threaded end portion 1134. The first leg 1122 also includes a pivot pin passage 1135 between the superior connector portion 1112 and the first leg 1122

A jaw 1140 is pivotally connected to the frame 1110 via a pivot pin 1142 that extends through the pivot pin passage 1135. The jaw 1140 has a first portion 1144 that extends along a first side of the first leg 1122 and a second portion 1146 that extends along an opposing side of the first leg 1122. The jaw 1140 has an engagement face 1148 that connects the first portion 1144 and the second portion 1146 to each other. The engagement face 1148 has a through-opening 1150 that is sized such that the stud 1130 extends through the through-opening 1150. The jaw 1140 also includes a recess 1152 formed in the engagement face 1148

Figures 50, 51, 52:
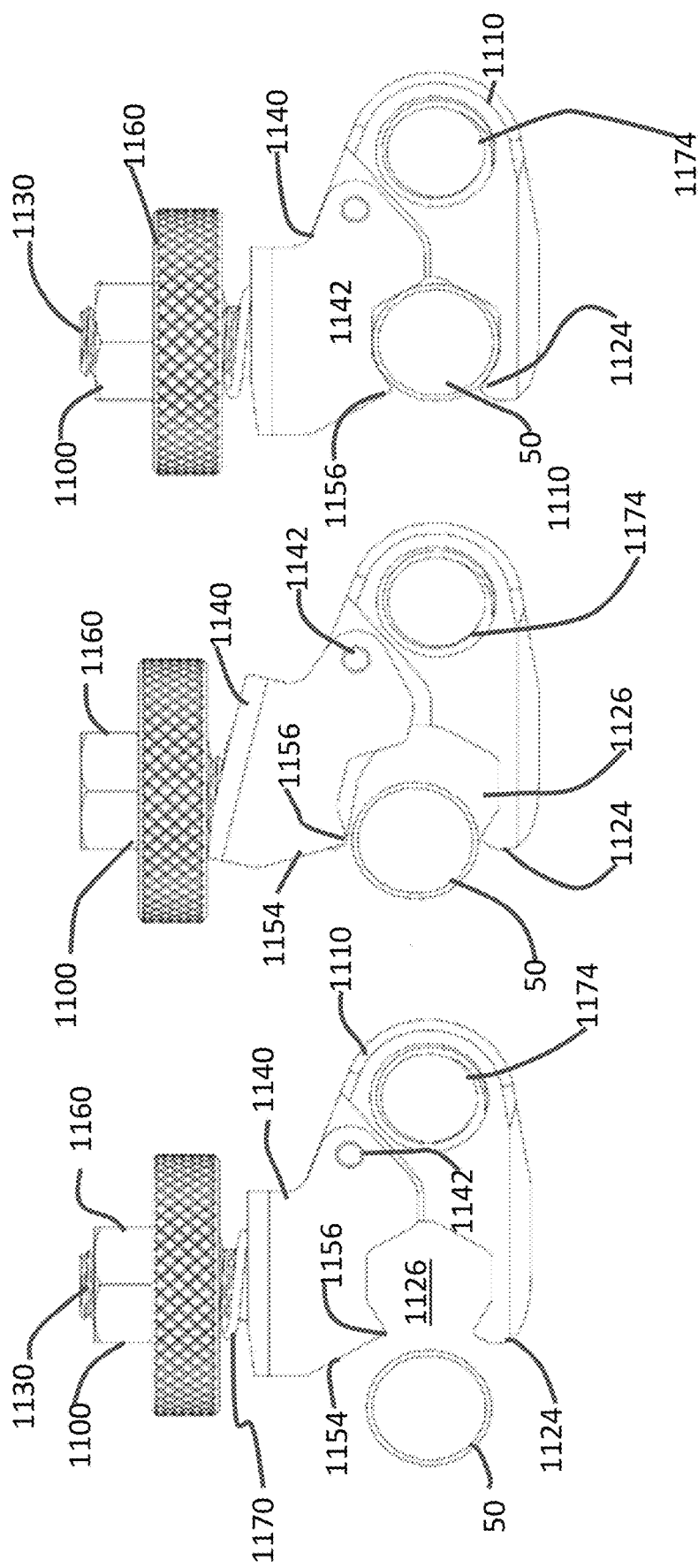
FIG. 50 is a side elevational view of the instrument of FIG. 45 with a rod construct just prior to insertion inserted therein.
FIG. 51 is a side elevational view of the instrument and rod construct of FIG. 50 with the rod construct being inserted therein.
FIG. 52 is a side elevational view of the instrument and rod construct of FIG. 51 with the rod construct having been inserted therein.

Each of first portion 1144 and second portion 1146 has an oblique face 1154 at the bottom thereof that extends downwardly toward engagement face 1148 such that, when instrument 1100 is placed over rod 50 and pushed down onto rod 50, rod 50 engages both oblique faces 1154 to pivot jaw 1140 away from rod 50 so that rod 50 can be inserted into rod passage 1124. Oblique face 1154 includes a tip 1156 that extends into rod passage 1126, as shown in FIGS. 50-52.

A securing device in the form of a nut 1160 is threadingly mounted on the stud 1130. A female threaded passage 1161 extends through the nut 1160 and threadingly engages with the threaded end portion 1134 on the stud 1130. The nut 1160 has a securing face 1162 that is adapted for engagement with the engagement face 1148 of the jaw 1140 such that, when the nut 1160 is advanced along the stud 1130 toward the frame 1110, the engagement face 1148 engages the securing face 1162 to provide a relatively large area for frictional contact between the jaw 1140 and the nut 1160. Similar to the jaw 1140, the nut 1160 also includes a recess 1164 formed in the securing face 1162.

The nut 1160 includes a round, knurled dial 1166 that can be grasped by a user's fingers (not shown) to rotate the nut 1160 on the stud 1130 to advance the first portion 1144 and the second portion 1146 of the jaw 1140 into the rod passage 1124. While the dial 1166 provides for hand tightening of the nut 1160, the nut 1160 also includes a hex face 1168 adjacent to the dial 1166 and outwardly from the jaw 140 so that, after the nut 1160 is hand tightened, the user can use a wrench (not shown) on the hex face 1168 to further tighten the nut 1160 onto the stud 1130.

A biasing member in the form of a helical spring 1170 is mounted on the stud 1130 and is held captive on the stud 1130 between the jaw 1140 and the nut 160. The spring 1170 biases the jaw 1140 away from the securing device 116 so that the first portion 1144 and the second portion 1146 of the jaw 1140 are biased into the rod passage 1124. The spring 1170 is also sized to be able to fit into at least one of the recess 1152 in the jaw 1140 or the recess 1164 in the nut 1160. As shown in FIG. 47, a portion of the spring 1170 fits into the recess 1152, while the remainder of the spring 1170 fits into the recess 1164, thus allowing for engagement between the engagement face 1148 and the securing face 1162.

A distraction bolt 1174 having male threads 1176 that are complementary to the threads in the female threaded through-passage 1114 extends from the first end 1116 of the through-passage 1114, through the through-passage 1114, and out the second end 1118 of the through-passage 1114. The distraction bolt 1174 has a hex head 1178 and a hollow end portion 1180, distal from the hex head 1178.

A foot plate 1182 is located at the second end 1114b of the through-passage 1114. The foot plate 1182 includes a generally cylindrical insert 1184 that extends into the hollow end portion 1180 of the distraction bolt 1174. The insert 1184 includes a pair of parallel annular grooves 1186, 1188 that receive respective C-clips 1190, 1192. The C-clips 1190, 1192 fit into corresponding grooves (not shown) formed in the hollow end portion 1180 of the distraction bolt 1174 such that, when the insert 1184 is inserted into the hollow end portion 1180, the C-clips snap into those grooves to retain the insert 1184 in the hollow end portion 1180 such that the insert 1184 is rotatably secured to the distraction bolt 1174.

The foot plate 1182 also includes a distraction face 1194 that is adapted to engage the clamp 90 to slide the clamp 90 along the rod 50. The distraction face 1190 includes a pair of face legs 1196, 1197 that extend along either side of the rod 50 so that, as the distraction bolt 1174 advances the foot plate 1182 against the clamp 90, the face legs 1196, 1197 prevent the foot plate 1182 from rotating.

A friction reducer in the form of a ball bearing 1198 is located inside the hollow end portion 1180 and engages the insert 1184. The ball bearing 1198 can be constructed from stainless steel, or a low friction material, such as, for example, nylon, Delrin®, or other suitable low friction materials. In axial compression, the ball bearing 1198 permits free axial rotation between the foot plate 1182 and the distraction bolt 1174.

An exemplary method of using the instrument 1110 to advance a member, such as the clamp 90, along the rod 50 includes the step of securing the clamp 90 to the rod 50 and attaching the instrument 1110 to the rod 50 proximate to the clamp 90, such as is shown in FIG. 48. The rod 50 is inserted into the rod passage 1124 such that the oblique face 1154 and the tip 1156 engage the rod 50. The rod 50 rides along the oblique face 1154 toward the tip 1128, as shown in FIG. 51. The jaw 1140 has sufficient clearance with respect to the nut 1160 so that, due to the action along the oblique face 1154, the jaw 1140 can be biased to pivot open toward the nut 1160 as the rod 50 is inserted into the rod passage 1124. As shown in FIG. 52, when the rod 50 is inserted into the rod passage 1124, the spring 1170 biases the jaw 1140 against the rod 50. Next, the nut 1160 is advanced from the position shown in FIG. 46 to the position shown in FIG. 47 toward the first leg 1122 to lock the jaw 1140 in position such that the first portion 1144 and the second portion 1146 each engages the rod 50 to secure the instrument 1100 to the rod 50.

As shown in FIG. 47, the fixator assembly 1100 may grip the rod 50 in at least six places over an arc that snaps over 180 degrees, providing a firm grip by the fixator assembly 1100 onto the rod 50.

After securing the instrument 1100 to the rod 50, the instrument 1100 is used to slide the clamp 90 along the rod from the location shown in FIG. 48 to the location shown in FIG. 49 by rotating and thus advancing the distraction bolt 1174 through the through-opening 1114 and linearly urging the foot plate 1182 against the clamp 90 such that the clamp 90 slides along the rod 50, repositioning the clamp 90 to a desired location.

Without limitation, an advantage of the instrument 1110 may include the snap action produced by the spring 1170 in conjunction with the jaw 1140. The sprung-closed pivoting jaw 1140 pivots to allow the rod 50 to be captured by the tip 1128 and the tip 1156.

Referring now to FIGS. 53-56, an exemplary nut assembly 1200 is shown. The nut assembly 1200 can be the same as the nut 1160 discussed above or, alternatively, the nut 1160 can be a unitary, single piece nut.

The nut assembly 1200 is a ratcheting tightening nut that allows for the nut assembly 1200 to be pushed down a center bolt, such as stud 1130 (shown in FIG. 46, for quick application and provisional hold of a device or instrument (not shown) onto a rod, pin, or both (not shown). Applying a final tightening torque on the nut assembly 1200 ensures a final strong hold.

The nut assembly 1200 includes a top hex portion 1220, a knurled flange component 1240, and an internal flexing thread portion 1260. The configuration can be constructed from two components, with the top hex portion 1220 and the knurled flange component 1240 being integrally formed as one component, with the internal flexing thread portion 1260 pressed into the one component.

The top hex portion 1220 includes a top end 1222 having a hex head 1224 and a bottom end 1226. The top end 1222 has an opening 1223 that is larger than the diameter of the stud 1130 so that the stud 1130 can fit through the opening 1223. The bottom end 1226 has male threads 1228. The threads 1228 are sized to fit into the knurled flange component 1240, as will be discussed in detail later herein.

A hollow passage 1230 extends axially through the top hex portion 1220 between the top end 1222 and the bottom end 1226. The hollow passage 1230 is tapered, with the portion at the top end 1222 being wider, and narrowing down to a smaller diameter at the bottom end 1226.

The knurled flange component 1240 is generally annular in shape, with a knurled outer perimeter 1242 and inner perimeter 1244. A top portion 1246 of the inner perimeter 1244 includes a threaded portion 1248. The threaded portion 1248 is sized to threadingly engage with the threaded portion 1228 on the top hex portion 1220, as shown in FIG. 54. A bottom portion 1250 of the inner perimeter 1244 is unthreaded and includes a radial lip 1252 with a smaller diameter than the perimeter of the threaded portion 1248. The bottom portion 1250, however, is larger than the diameter of the stud 1130 so that the stud 1130 can fit through the knurled flange component 1240.

The internal flexing thread portion 1260 ("portion 1260") is split in order to allow for radial compression and outward flexure of the portion 1260. The outer perimeter 1262 of the portion 1260 is tapered with generally the same degree of taper as the hollow passage 1230. This taper allows for the portion 1260 to flex when the nut assembly 1200 is pushed downward along the stud 1130.

The portion 1260 also includes a pair of diametrically opposed shoulders 1264 extending outwardly from the outer perimeter 1262. The shoulders 1264 are used to frictionally grip the wall of the hollow passage 1230 when securing the nut assembly 1200 onto the stud 1130.

The portion 1260 also includes an inner perimeter 1266 that has internal threads 1268 extending only partially therearound. This feature allows the portion 1260 to "ratchet down" onto the stud 1130 when the nut assembly 1200 is initially inserted over the stud 1130.

The portion 1260 is press fit into the top hex portion 1220 from the bottom. The top hex portion 1220 is then threaded onto the knurled flange component 1240, thereby encapsulating the portion 1260 in the passage 1230. A weld (not shown) is then be added across the top hex portion 1220 and the knurled flange component 1240 in order to seal the connection between the top hex portion 1220 and the knurled flange component 1240.

To secure the nut assembly 120 to the stud 1130, axial force is applied on the nut assembly 1200. The portion 1260 translates towards the top of the hex portion 1220, as shown in FIG. 55, where the portion 1260 flexes open, allowing the nut assembly 1200 to ratchet down the stud 1130. When final tightening is applied to the nut assembly 1200 as shown in FIG. 56, the threads 1268 of the portion 1260 catch onto the stud 1130 and tighten down the entire nut assembly 1200.

Torque is transmitted from the hex portion 1220 or the knurled flange component 1240 through the shoulders 1264, translating the portion 1260 along the center stud 1130, disabling the ratcheting feature. Alternative methods can be used to transmit the torque such as pins, hex geometry, or another female blocker method.

At all times, the nut assembly 1200 is allowed to thread on and off the stud 1130 for revision. Optionally, a spring (not shown) can bias the portion 1260 into the threading position until axial force is applied.

Figure 63:
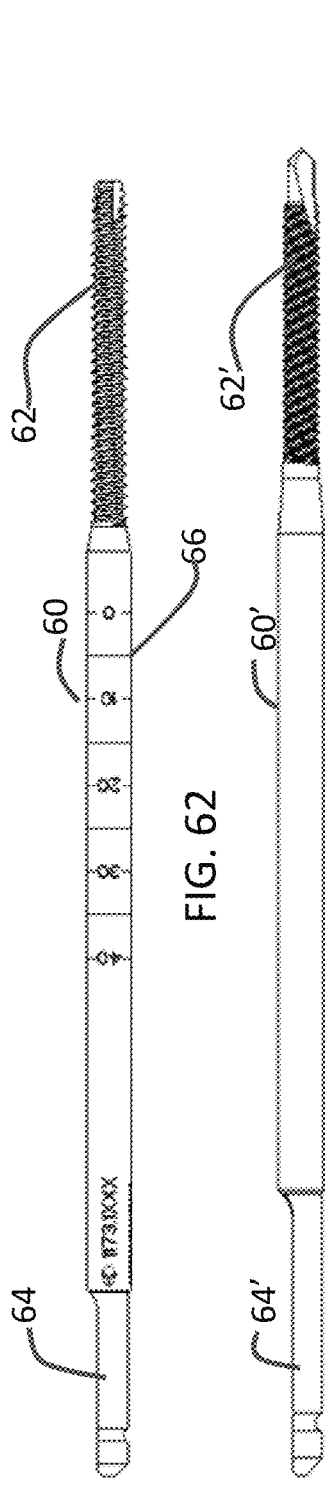
FIG. 63 is a side elevational view of an alternative embodiment of the pin of FIG. 59.
Figure 64:
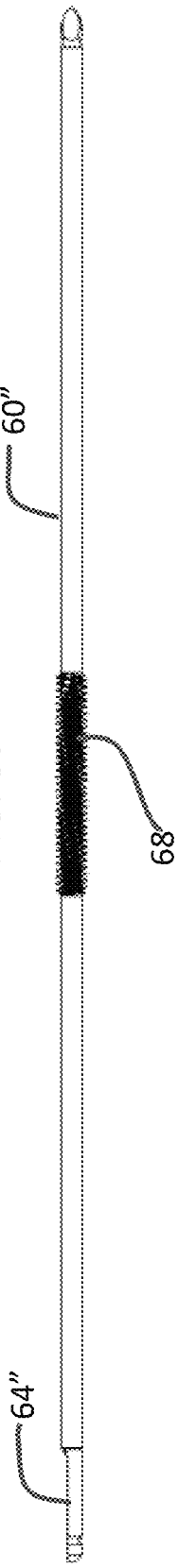
FIG. 64 is a side elevational view of still another alternative embodiment of the pin of FIG. 59.
Figure 66:
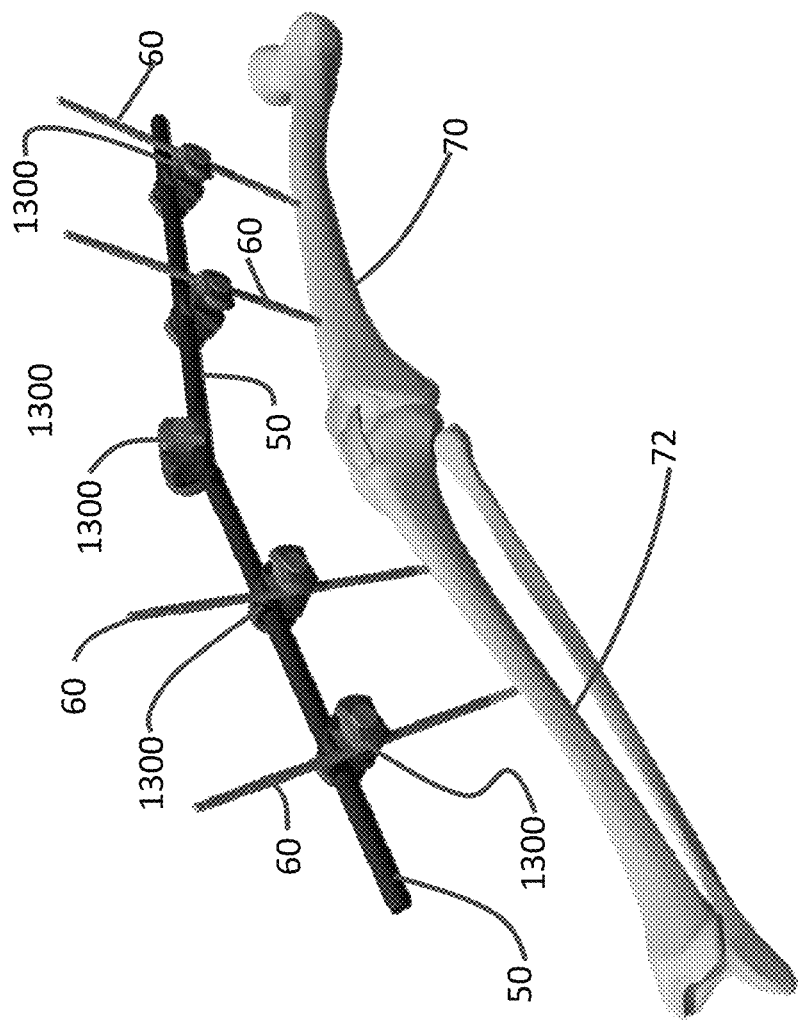
FIG. 66 is a perspective view showing the external fixator assembly, rods, and pins of FIG. 57 attached to two adjacent bones.
Figure 65:
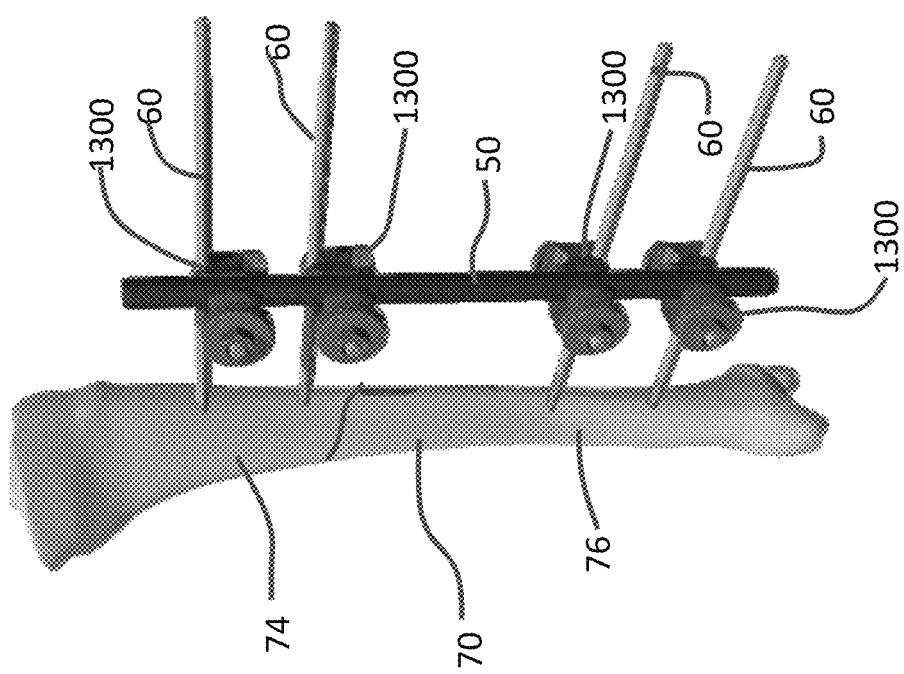
FIG. 65 is a perspective view showing the external fixator assembly, rods, and pins of FIG. 57 attached to bone segments.
Figure 70:
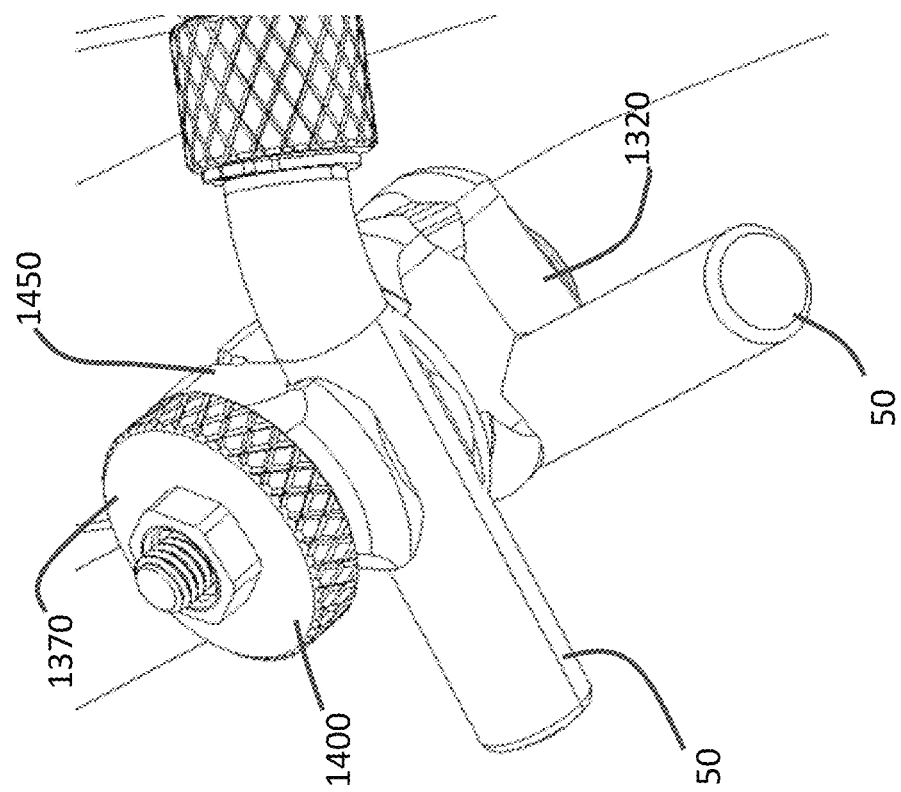
FIG. 70 is a perspective view of the external fixator assembly of FIG. 67 connected to two rods.
Figure 67:
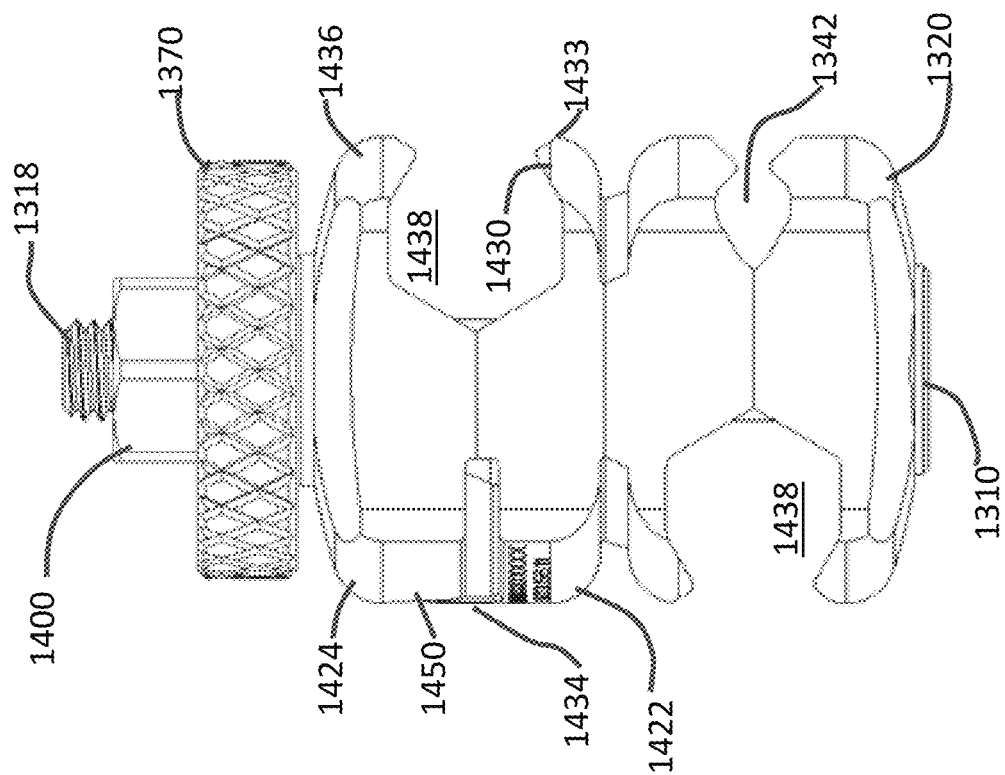
FIG. 67 is a side elevational view of an alternative embodiment of an external fixator assembly.
Figure 68:
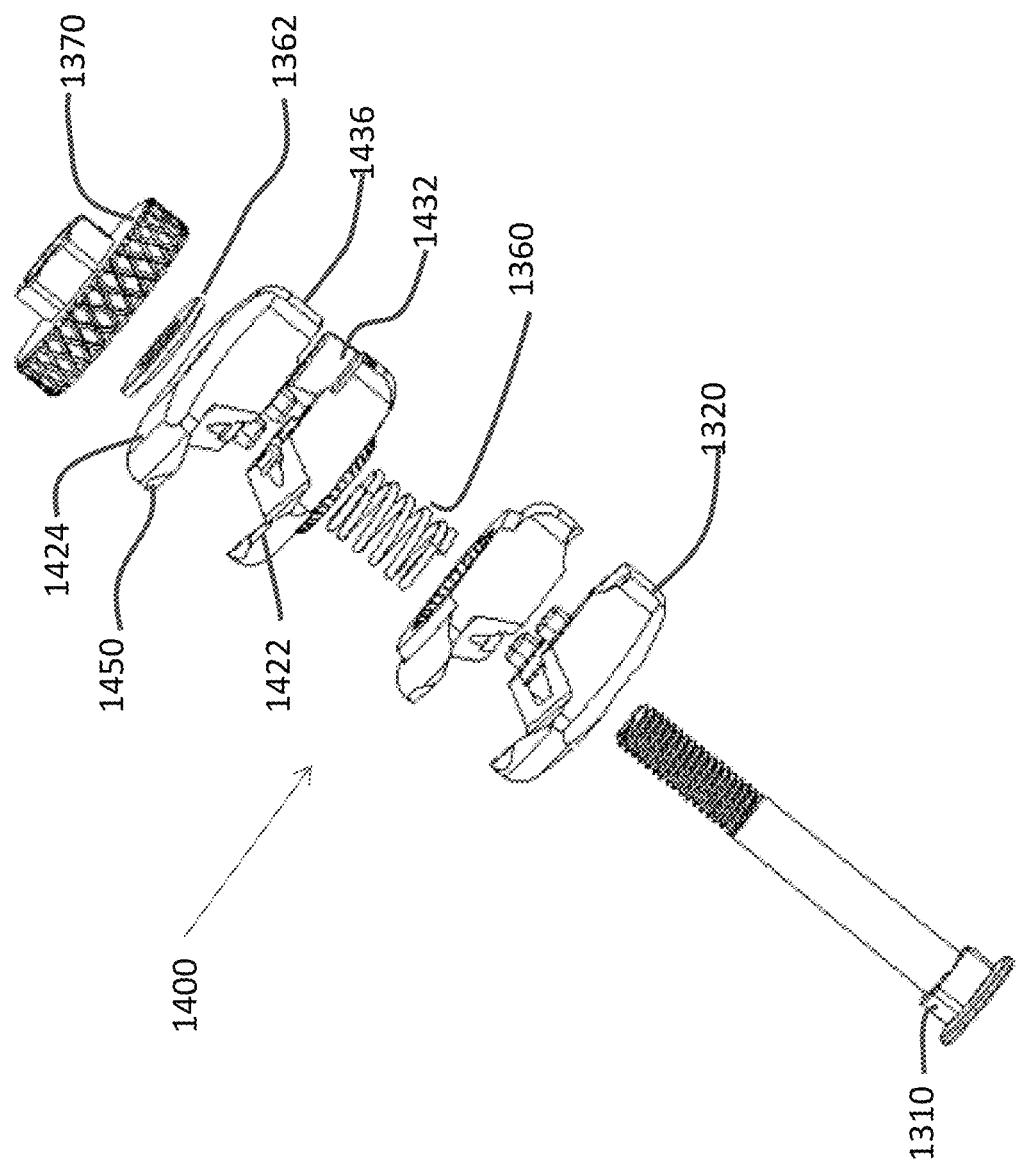
FIG. 68 is an exploded perspective view of the external fixator assembly of FIG. 67.
Figure 69:
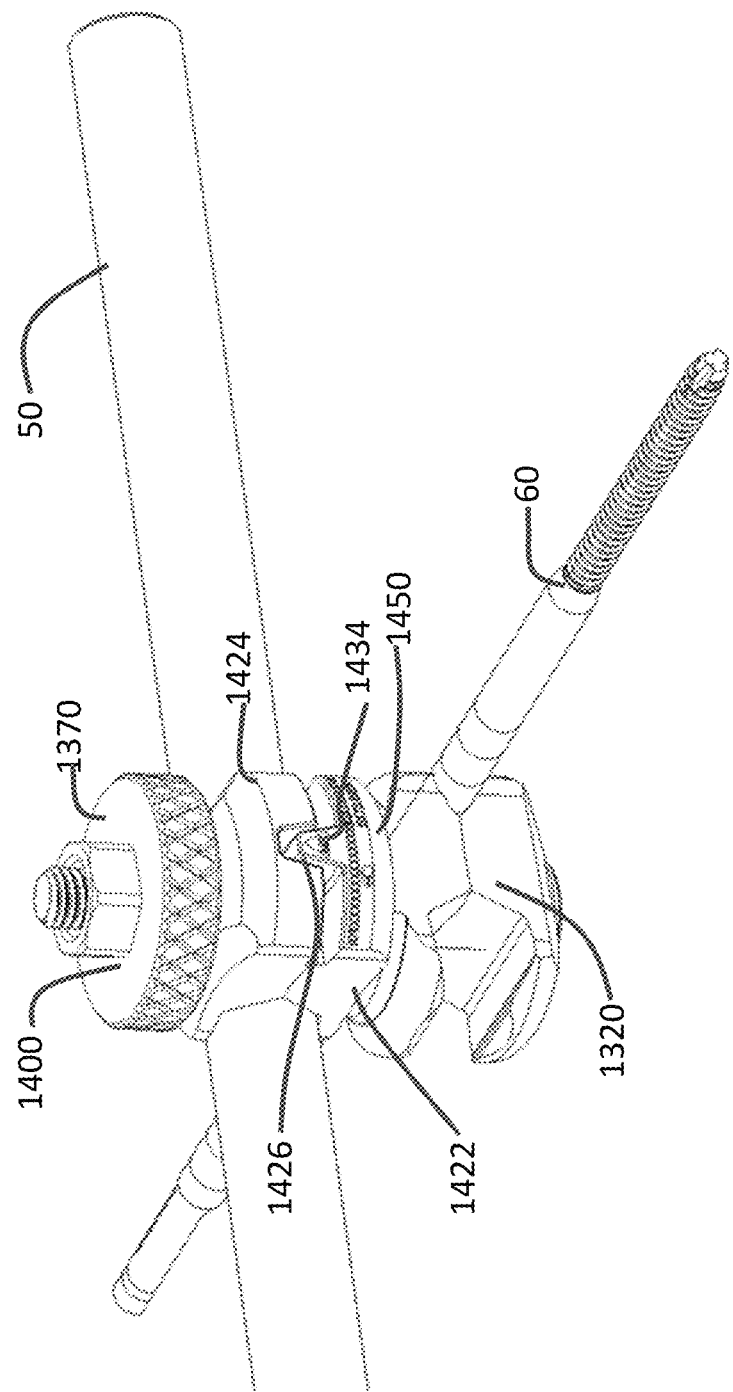
FIG. 69 is a perspective view of the external fixator assembly of FIG. 67 connected to a rod and to a pin.

Referring to FIGS. 57-66, an exemplary external fixator assembly 1300 ("fixator assembly 1300") is shown. As shown specifically in FIGS. 59, 65, and 66, the fixator assembly 1300 is used in conjunction with rods 50 and pins 60 to secure and stabilize adjacent bones 70, 72 (shown in FIG. 66) or to stabilize broken pieces 74, 76 of the same bone 70 (shown in FIG. 65). While a tibia 72 and a femur 70 are shown in FIGS. 65 and 66, those skilled in the art will recognize that the fixator assembly 1300, along with rods 50 and pins 60, can be used to fixate other bones, and other bone pairs as well.

Figure 59:
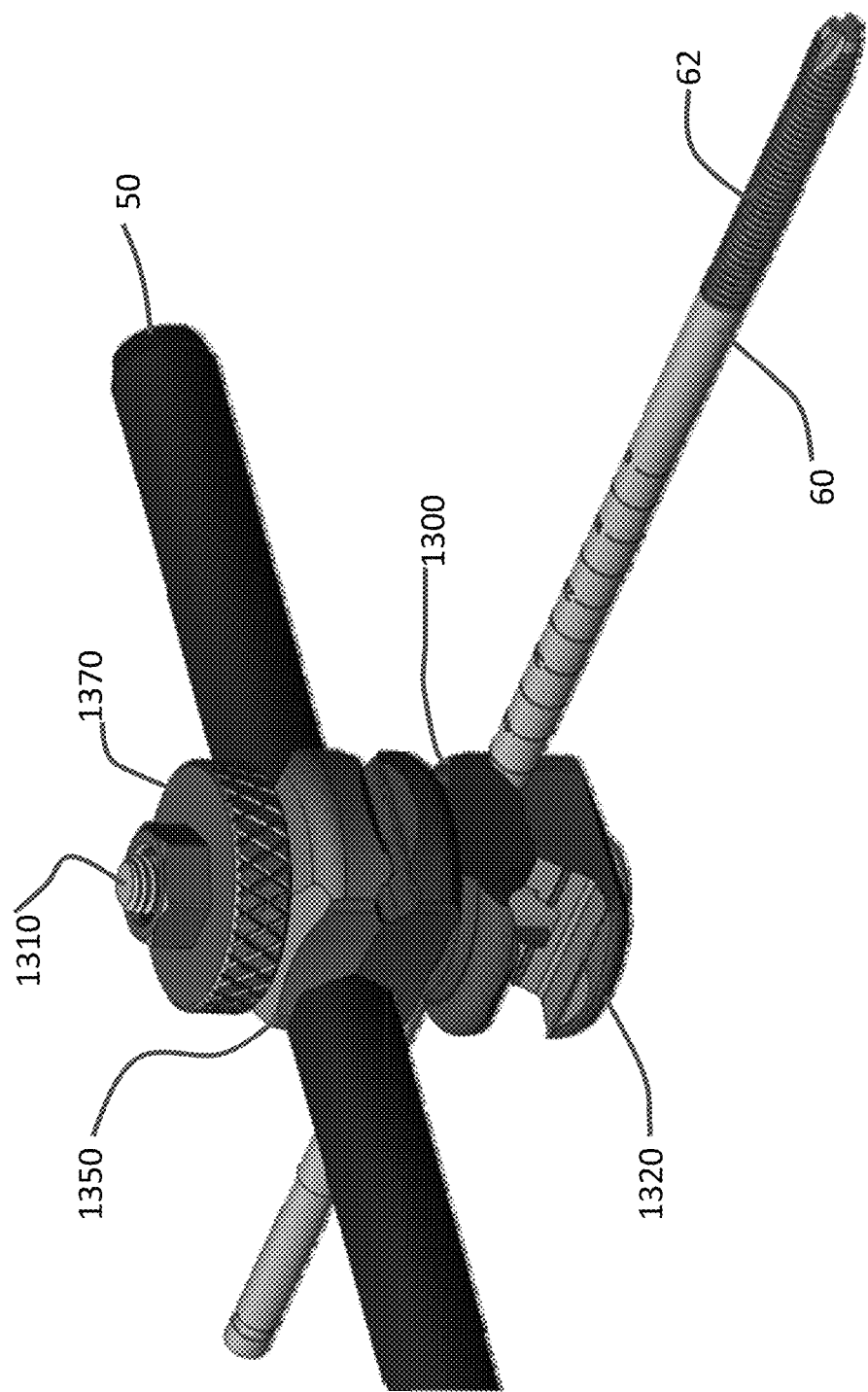
FIG. 59 is a perspective view showing the external fixator assembly of FIG. 57 connected to a rod and a pin.
Figure 60:
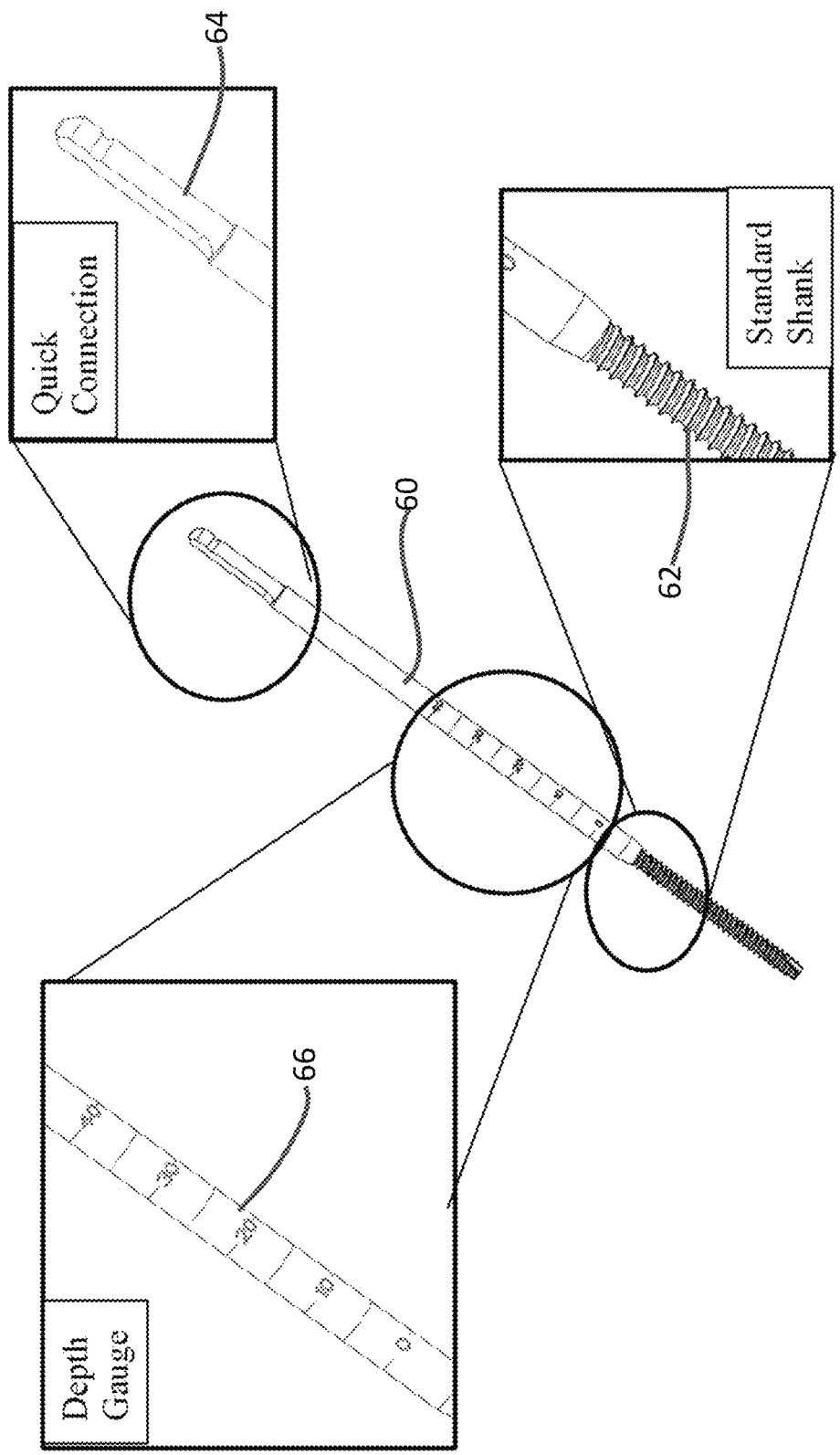
FIG. 60 is a perspective view of the pin of FIG. 59 with enlarged views of aspects of the pin.
Figure 61:
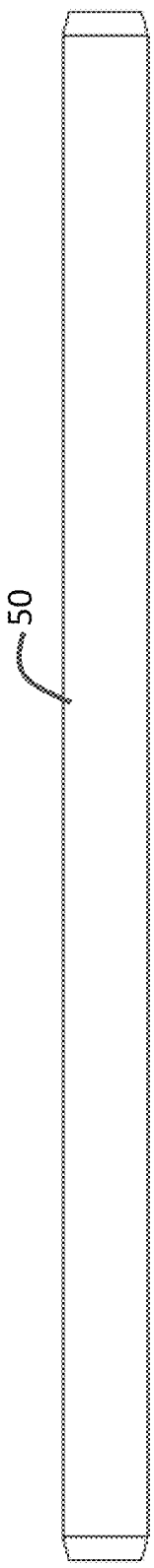
FIG. 61 is a side elevational view of the rod of FIG. 59.
Figure 62:
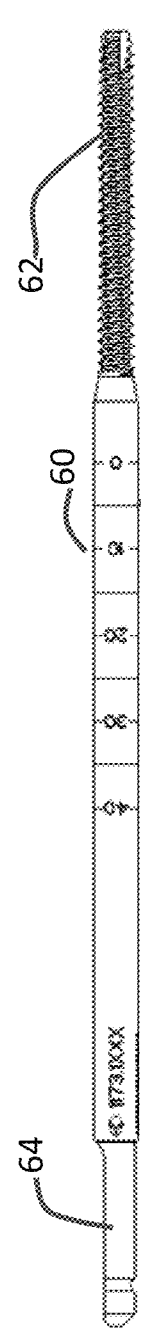
FIG. 62 is a side elevational view of the pin of FIG. 59.

As shown in FIG. 59, the fixator assembly 1300 can be used to releasably secure the rod 50 and the pin 60 through the use of a plurality of connector assemblies. In an exemplary embodiment, the rod 50 can be constructed from a rigid material, such as, for example, a carbon fiber, and can optionally be coated with a material, such as, for example, titanium, to make the rod 50 more compatible with MRI or other radiographic use. The rod 50 has a first diameter. The length of the rod 50 can be varied depending on the need for a particular application.

The pin 60 can include a self-tapping end 62 that is inserted into bone 70, 72. Optionally, the end 62 can be coated with an antimicrobial material, such as, for example, silver or silver ions, in order to reduce the likelihood of infection. The pin 60 has a second diameter, smaller than the first diameter of the rod 50. The length and diameter of the pin 60 can vary, depending on the patient or the injury, as well as surgeon preference.

While FIG. 59 shows fixator assembly 1300 being used to secure a single rod 50 and a single pin 60, those skilled in the art will recognize that the fixator assembly 1300 can, depending upon the particular situation and injury, be used to connect two rods 50, as shown in FIG. 66, or even two pins 60 (not shown).

Figure 57:
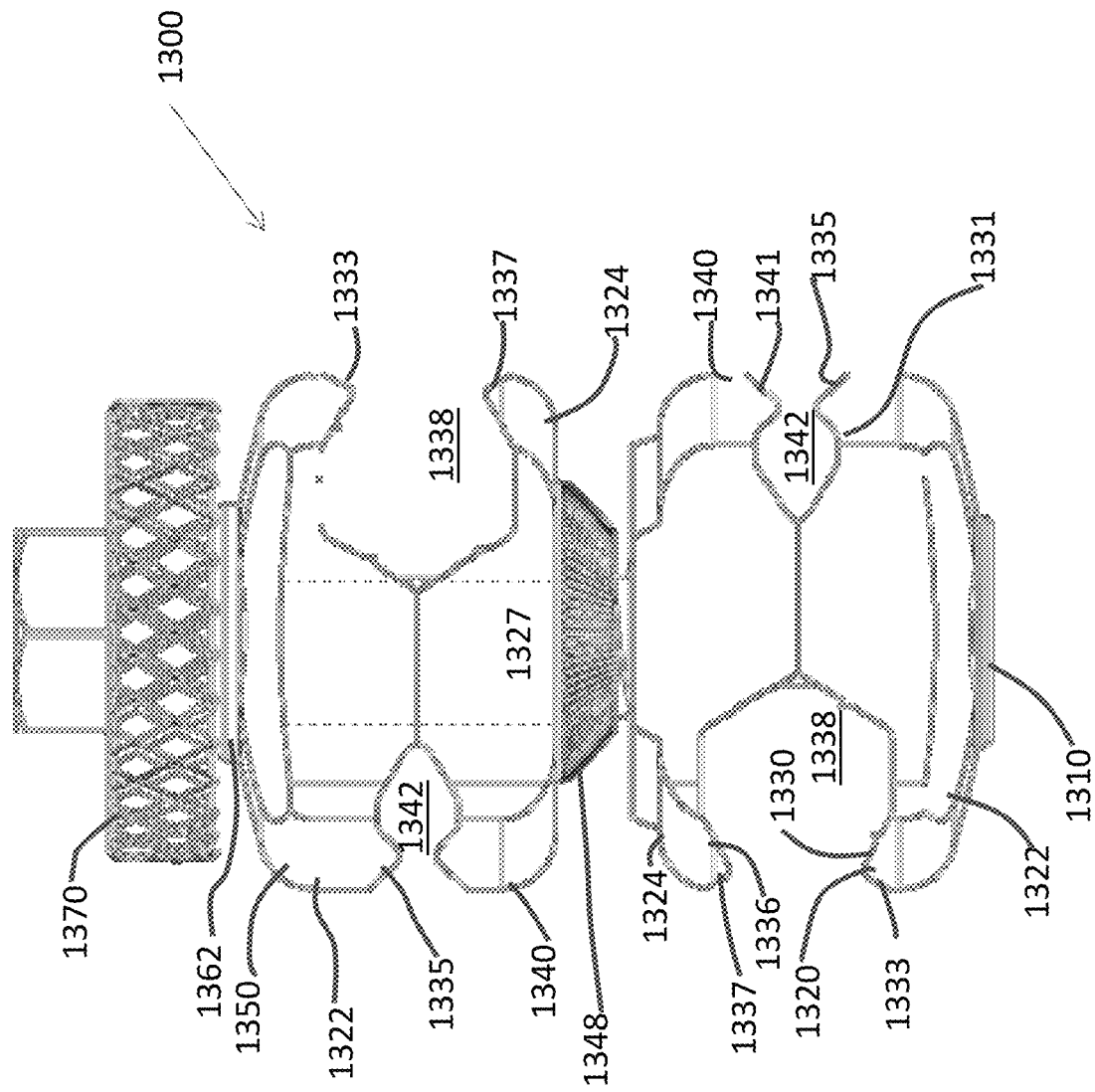
FIG. 57 is a side elevational view of an alternative embodiment of an external fixator assembly.
Figure 58:
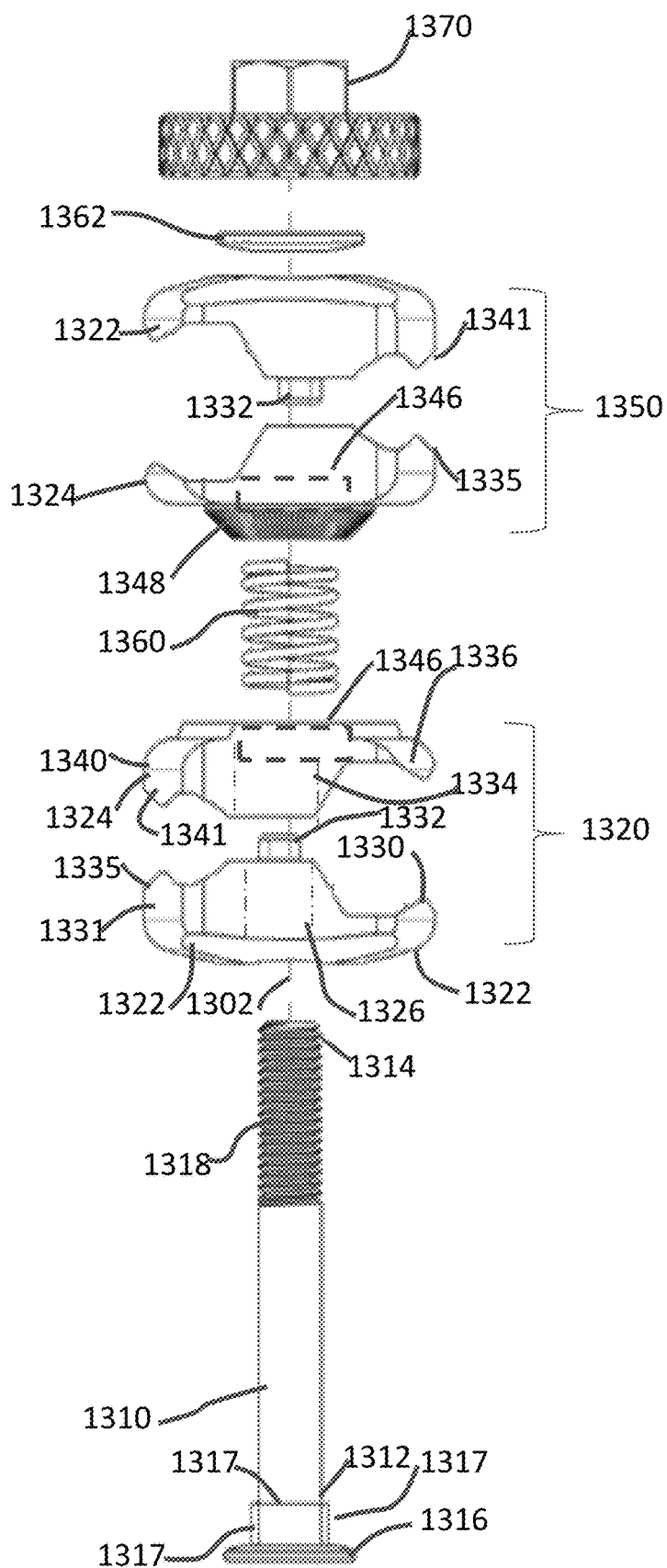
FIG. 58 is an exploded view of the external fixator assembly of FIG. 57.

As shown in FIG. 58, the fixator assembly 1300 includes a longitudinal axis 1302 extending therethrough. Referring now to FIGS. 57 and 58, the fixator assembly 1300 includes a shaft 1310 and a plurality of clamp assemblies 1320, 1350 extending along the shaft 1310. The shaft 110 extends along the longitudinal axis 102. The shaft 1310 can be constructed from a medical grade material, such as medical grade stainless steel, for example, Biodur® 108 stainless steel.

A biasing member 1360 is disposed between adjacent of the plurality of clamp assemblies 1320, 1350. The biasing member 1360 may be, for example, a spring, such as a helical spring. The biasing member 1360 may also be constructed form a medical grade material, such as stainless steel.

A cap, or ratchet, assembly 1370 secures the clamp assemblies 1320, 1350 onto shaft 1310. Ratchet assembly 1370 can be the same as any of ratchet assembly 170, nut 1160, or nut assembly 1200 as described above.

The shaft 1310 has a distal end 1312 and a proximal end 1314 extending away from the distal and 1312. The distal end 1312 includes a radially extending flange 1316 and at least one flat surface 1317 extending proximally of flange 1316. While FIG. 58 shows three flat surfaces 1317, those skilled in the art will recognize that shaft 1310 can include more or less than three flat surfaces 1317.

The proximal end 1314 of the shaft 1310 has at least one external thread 1318. Optionally, a length of the shaft 1315 between the distal end 1312 and the proximal end 1314 can be generally circular, that is, devoid of any flat surfaces or threads. The shaft 1310 is sufficiently long to allow for the insertion of the clamp assemblies 1320, 1350 and the ratchet assembly 1370 thereon.

The clamp assemblies 1320, 1350 extend along the shaft 1310 from the distal end 1312 toward the proximal end 1314 such that the clamp assembly 1320 engages the flange 1316 and the clamp assembly 1350 engages the clamp assembly 1320. While two clamp assemblies 1320, 1350 are shown, those skilled in the art will recognize that more than two clamp assemblies 1320, 1350 can be used with the fixator assembly 1300. Alternatively, it can be envisioned that only a single clamp assembly 1320 is used with fixator assembly 1300.

The clamp assemblies 1320, 1350 can be, although are not necessarily, identical to each other. The clamp assembly 1320 includes a lower member 1322 and an upper member 1324 extending proximally of the lower member 1322. The lower member 1322 includes an axially extending passage 1326 that is sized to allow the shaft 1310 to extend therethrough. The passage 1326 can include internal flat surfaces (not shown) that are adapted to engage with the flat surfaces 1317 on the shaft 1310 to prevent the lower member 1322 of the clamp assembly 1320 from rotating with respect to the shaft 1310.

The lower member 1322 includes a first generally U-shaped portion 1330 having a radius that is sized to receive a portion of the rod 50. The first generally U-shaped portion 1330 has an oblique face 1333 that acts as a lead-in to enhance ease of insertion of the rod 50 into the first generally U-shaped portion 1330.

The lower member 1322 also includes a second generally U-shaped portion 1331, radially disposed away from the first concave portion 1330, having a radius that is sized to receive a portion of the pin 60. The second generally U-shaped portion 1310 has an oblique face 1335 that acts as a lead-in to enhance ease of insertion of the pin 60 into the second generally U-shaped portion 1331. As shown in FIG. 58, the lower member 1322 also includes a tang 1332 extending outwardly therefrom in a proximal direction toward the upper member 1324.

The upper member 1324 includes an axially extending passage 1334 that is sized to allow the shaft 1310 to extend therethrough. The upper member 1324 further includes a first generally inverted U-shaped portion 1336 having a radius that is sized to receive a portion of the rod 50, such that, when the upper member 1324 is biased toward the lower member 1322, the rod 50 is received in a cavity 1338 that is formed by the first generally U-shaped portion 1330 of the lower member 1322 and the first generally inverted U-shaped portion 1336 of the upper member 1324. The first generally inverted U-shaped portion 1336 has an oblique face 1337 that acts as a lead-in to enhance ease of insertion of the rod 50 into the first generally inverted U-shaped portion 1336.

The geometry of the U-shaped portions 1330, 1336 are sized to maximize the contact area between the U-shaped portions 1330, 1336 and the rod 50 to reduce translation or rotation of the rod 50 relative to the clamp assembly 1320 when part of a construct.

The upper member 1324 also includes a second generally inverted U-shaped portion 1340, radially disposed away from the first generally inverted U-shaped portion 1336, having a radius that is sized to receive a portion of the pin 60, such that, when the upper member 1324 is biased toward lower member 1322, the pin 60 is received in a cavity 1342 formed by the second generally inverted U-shaped portion 1331 of the lower member 1322 and the second generally inverted U-shaped 1340 of the upper member 1324. The second generally inverted U-shaped portion 1340 has an oblique face 1341 that acts as a lead-in to enhance ease of insertion of the pin 60 into the first generally inverted U-shaped portion 1340.

The upper member 1324 also includes a slot (not shown) formed therein, such that the slot is adapted to releasably receive the tang 1332 from the lower member 1322, thereby preventing the upper member 1324 from rotating about the longitudinal axis 1302 relative to the lower member 1322. The slot is sufficiently large to allow the tang 1332 to angulate to receive the rod 50.

The upper member 1324 also includes a spring cavity 1346 that is sized to receive the biasing member 1360. A toothed locking half (not shown) surrounds the spring cavity 1346.

The second clamp assembly 1350 is similar to the first clamp assembly 1320 with the exception that, instead of internal flat surfaces, the clamp assembly 1350 has an axially extending passage 1327 that is sufficiently larger than the diameter of the shaft 1310 such that the clamp assembly 1350 is freely rotatable about the shaft 1310 and is also rotatable relative to the clamp assembly 1320. As shown in FIGS. 57 and 58, the second clamp assembly 1350 is inserted over the shaft 1310 "upside down" relative to the 1320 such that the toothed locking half 1348 of the clamp assembly 1350 is engageable with the locking half of the first clamp assembly 1320 such that, when the clamp assembly 1350 is biased against the clamp assembly 1320, the toothed locking half 1348 of the clamp assembly 1350 engages the toothed locking half of the clamp assembly 1320, preventing rotation of the clamp assembly 1350 with respect to the clamp assembly 1320.

The locking halves form a star grind, as described above with respect to external fixator assembly100. Locking half 1348 is conical in shape with the locking half in first clamp assembly 1320 having a mating shape. The angle formed by the cone aids with the initial alignment of the clamp assemblies 1320, 1350 as the clamp assemblies 1320, 1350 are tightened and guides the locking halves together. When fully tightened, the star grind forms a rigid connection between the clamp assemblies 1320, 1350.

In an exemplary embodiment, each toothed locking half 1348 includes a plurality of teeth, for example, about 90 teeth, such that the clamp assembly 1350 can be indexed with respect to the clamp assembly 1320 about 4°. Those skilled in the art, however, will recognize that each toothed locking half 1348 can include more or less than 90 teeth (e.g., 50-150 teeth, 75-125 teeth, or 80-100 teeth), such that the amount or degree of indexing of the clamp assembly 1350 with respect the clamp assembly 1320 is adjustable accordingly (e.g., 1-20°, 1-10°, or 2-6°).

As shown in FIG. 58, the biasing member 1360 is disposed between the clamp assembly 1320 and the clamp assembly 1350 and is retained between the clamp assembly 1320 and the clamp assembly 1350 within spring cavities 1346. In an exemplary embodiment, the biasing member 1360 is a helical spring, although those skilled in the art will recognize that other types of biasing members can be used. The biasing member 1360 biases the clamp assembly 1320 and the clamp assembly 1350 apart from each other, such that the clamp assembly 1320 and the clamp assembly 1350 securely engage a rod 50 that may be inserted into the cavity 1338 and/or a pin 60 that may be inserted into the cavity 1342.

Referring to FIGS. 57 and 58, the ratchet assembly 1370 is disposed over the proximal end 1314 of the shaft 1310, such that the ratchet assembly 170 biases the clamp assemblies 1320, 1350 toward the distal end 1312 of the shaft 1310 and flange 1316 so that the clamp assemblies 1320, 1350 are not rotatable with respect to each other. A conical washer 1362 is axially disposed between the second clamp assembly 1350 and ratchet assembly 1370 to distribute compressive forces applied by the ratchet assembly 1370 onto the second clamp assembly 1350. The conical shape of the washer 1362 allows for changes in the angulation of the second clamp assembly 1350 relative to the ratchet assembly 1370.

To assemble the fixator assembly 1300, the first clamp assembly 1320 is slid from the proximal end 1314 of the shaft 1310 to the distal end 1312 of the shaft 1310, bottoming out on the flange 1316. The first clamp assembly 1320 is aligned such that the toothed locking half 1348 is facing the proximal end 1314 of the shaft 1300. Next, the biasing member 1360 is slid along the shaft 1310 such that at least a portion of the biasing member 1360 is seated within the spring cavity 1346.

The second clamp assembly 1350 is then slid from the proximal end 1314 of the shaft 1310 toward the first clamp assembly 1320. The second clamp assembly 1350 is aligned such that the toothed locking half 1348 is facing the distal end 1312 of the shaft 1310 so that at least a remaining portion of the biasing member 1360 is seated within the spring cavity 1346 in the second clamp assembly 1350 and so that the toothed locking half 1348 of the second clamp assembly 1350 is facing the toothed locking half 1348 of the first clamp assembly 1320.

The washer 1362 is slid over the shaft 1310. The ratchet assembly 1370 is then slid over the shaft 1310. At this point, the cavities 1338, 1342 are sufficiently large to allow the rod 50 be slid into the cavity 1338 and the pin 60 to be slid into the cavity 1342 and also to allow the second clamp assembly 1350 to axially rotate relative to the first clamp assembly 1320.

In this condition, the surgeon can align the rod 50 and the pin 60 in desired positions with respect to the fixator assembly 1300. The surgeon can then provisionally tighten the ratchet assembly 1370 by further sliding the ratchet assembly 1370 distally along the shaft 1310 and then perform a final tightening of the fixator assembly 1300 by applying a wrench or other court applying device (not shown) to the ratchet assembly 1370 and rotating the ratchet assembly 1370 relative to the shaft 1310.

The ratchet assembly 1370 allows for the rapid application of the clamp assemblies 1320, 1350 onto the rod 50 (shown in FIG. 61) and/or the pin 60. The ratchet assembly 1370 also provides a quick method for provisional tightening of the fixator assembly 1300 while the surgeon is assembling the fixator assembly 1300 with the bar(s) 50 and pin(s) 60. Once set, a final tightening of the ratchet assembly 170 can be applied using a torque limiting adapter under power.

As shown in FIGS. 60 and 62-64, pins 60 can have different configurations. For example, in FIGS. 60 and 62, pin 60 can have the self-tapping end 62 and a quick connection end 64, with laser etched graduations 66 that correspond to a depth insertion of the pin 60 into a bone to help with placement.

As shown in FIG. 63 a pin 60' can have a self-drilling/self-tapping end 62' and, as shown in FIG. 64, a pin 60" can have a centrally threaded portion 68. Pins 60, 60', 60" have standardized shanks 64, 64', 64" that allow for a single external fixator assembly 1300 to be used for any pin 60, 60', 60" when assembling a construct.

With external fixation assembly 1300, rods 50, and pins 60, a surgeon can assembly the external fixator assembly 1300 in a variety of ways, depending on the injury. With the ability to connect to both rods 50 and pins 60, a wide range of constructs can be built. For spanning a large distance, as shown in FIG. 66, a rod-to-rod connection can be made.

Figure 72:
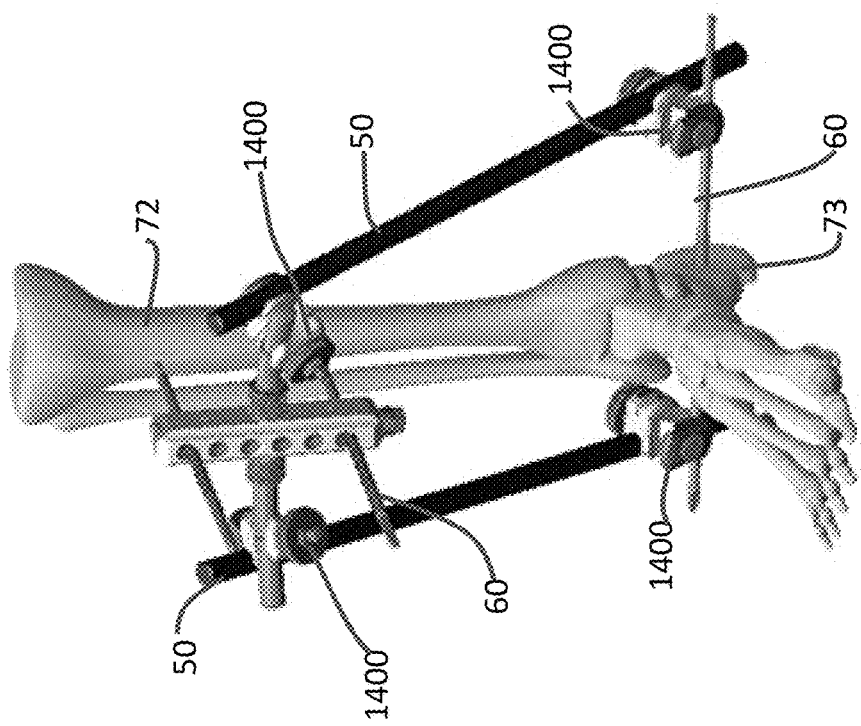
FIG. 72 is a perspective view of the external fixator assembly with rods and pins of FIG. 69 attached to two adjacent bones.
Figure 71:
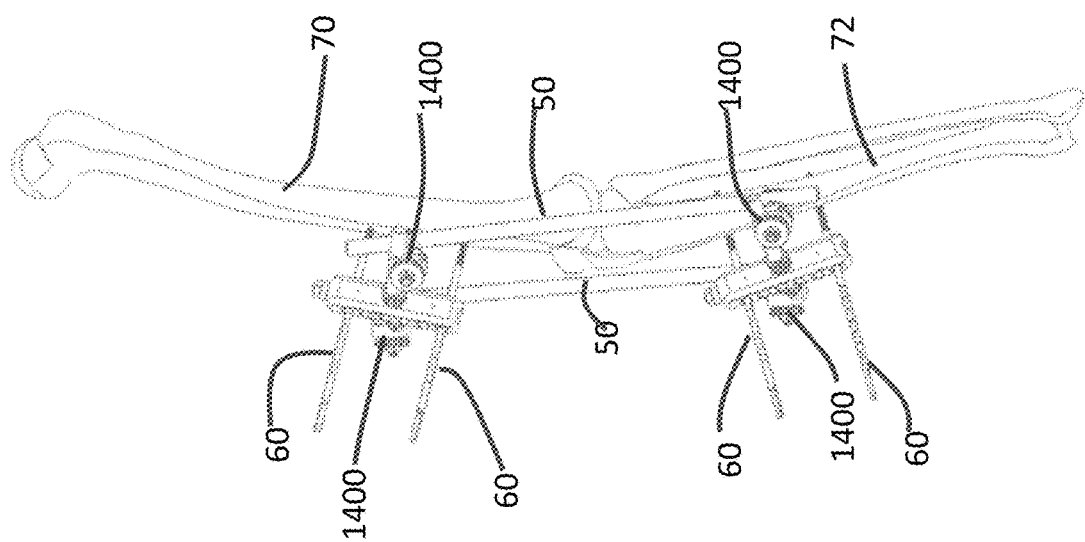
FIG. 71 is a perspective view of the external fixator assembly with rods and pins of FIG. 69 attached to two adjacent bones.

Referring now to FIGS. 67-72, an exemplary external fixator assembly 1400 is provided. The fixator assembly 1400 is similar to the fixator assembly 1300 described above with the difference that, instead of the second clamp assembly 1350 being configured to accept both a rod 50 and a pin 60, the second clamp assembly 1450 in the fixator assembly 1400 is configured to accept only the rod 50. As shown in FIGS. 71 and 72, however, the fixator assembly 1400 can be used in conjunction with rods 50 and pins 60 to secure and stabilize adjacent bones 70, 72 (shown in FIG. 71) or adjacent bones 72, 73 (shown in FIG. 72).

The second clamp assembly 1450 includes a lower member 1422 and an upper member 1424 that mate together to receive and retain a rod 50. Lower member 1422 has a first generally U-shaped portion 1430 having a radius that is sized to receive a portion of the rod 50. The first generally U-shaped portion 1430 has an oblique face 1433 that acts as a lead-in to enhance ease of insertion of the rod 50 into the first generally U-shaped portion 1430.

The lower member 1422 also includes a tang 1432 extending outwardly therefrom in a proximal direction toward the upper member 1424.

The upper member 1424 includes a first generally inverted U-shaped portion 1436 having a radius that is sized to receive a portion of the rod 50, such that, when the upper member 1424 is biased toward the lower member 1422, the rod 50 is received in a cavity 1438 that is formed by the first generally U-shaped portion 1430 of the lower member 1422 and the first generally inverted U-shaped portion 1436 of the upper member 1424. The first generally inverted U-shaped portion 1436 has an oblique face 1437 that acts as a lead-in to enhance ease of insertion of the rod 50 into the first generally inverted U-shaped portion 1436.

The geometry of the U-shaped portions 1430, 1436 are sized to maximize the contact area between the U-shaped portions 1430, 1436 and the rod 50 to reduce translation or rotation of the rod 50 relative to the clamp assembly 1450 when part of a construct.

The upper member 1424 includes a recess 1426 that is sized and shaped to receive the protrusion 1434. Engagement of the tang 1432 into the recess 1426 prevents the upper member 1424 from rotating about the longitudinal axis 1302 relative to the lower member 1422.

It will be further understood that various changes in the details, materials, and arrangements of the parts which have been described and illustrated in order to explain the nature of this invention may be made by those skilled in the art without departing from the scope of the invention as expressed in the following claims.

What is claimed is:

1. A method of advancing a member along a rod construct, the method comprising:
   providing a distractor/compression instrument comprising:
      a frame having:
         a rod passage;
         a superior section having a through-passage extending therethrough along a longitudinal axis; and
         an inferior section having a stud extending transverse relative to the through-passage;
      a jaw pivotally attached to the frame, the jaw having a through-opening configured to engage the stud;
      a distraction bolt extending through the through-passage;
      a foot plate having an insert engaged with the distraction bolt;
   securing the member to the rod construct;
   inserting the rod construct into a rod passage such that the foot plate engages the member;
   engaging the jaw against the rod construct; and
   advancing the distraction bolt through the through-passage and urging the foot plate against the member such that the member slides along the rod construct.

2. The method of claim 1, wherein the through-passage has a female thread and the distraction bolt has a male thread, complementary to the female thread.

3. The method of instrument of claim 1, wherein an inferior portion of the frame includes a first leg, such that the stud extends from the first leg, a second leg, and an open passage formed between the first leg and the second leg.

4. The method of claim 1, wherein the stud has a threaded portion, further comprising a securing nut threadingly mounted on the threaded portion.

5. The method of claim 4, wherein the distraction/compression instrument includes a biasing member disposed over the stud between the jaw and the securing nut, the biasing member being adapted to bias the jaw away from the securing nut.

6. The method of claim 5, wherein at least one of the jaw and the securing nut has a recess sized to accommodate the biasing member such that when the securing nut is fully tightened on the stud, the securing nut engages the jaw.

7. The method of claim 1, wherein the distraction/compression instrument includes a ball bearing located inside a hollow end portion and engaging the insert.

8. The method of claim 1, wherein the insert is rotatably secured to the distraction bolt.

9. A method of advancing a member along a rod construct, the method comprising:
   providing a distractor/compression instrument including:
      a frame having a first leg and a second leg, wherein the first leg includes a stud, and wherein the first leg and second leg form a rod passage therebetween;
      a connector section having a through-passage along a longitudinal axis;
      a jaw pivotally attached to the frame between the first leg and the connector section along a pivot axis parallel to the longitudinal axis of the through-passage;
      a securing device mounted on the stud;
      a distraction bolt extending through the through-passage; and
      a foot plate configured to engage with the distraction bolt;
   securing the member to the rod construct;
   inserting the rod construct into the rod passage such that the foot plate engages the member;
   advancing the securing device toward the first leg such that the jaw engages the rod construct; and
   advancing the distraction bolt through the through-passage and urging the foot plate against the member such that the member slides along the rod construct.

10. The method of claim 9, wherein the stud has a threaded end portion.

11. The method of claim 10, wherein the securing device is threadingly mounted on the stud.

12. The method of claim 9, wherein the distractor/compression instrument includes a biasing member mounted on the stud between the jaw and the securing device, the biasing member biasing the jaw away from the securing device.

13. The method of claim 12, wherein when the securing device is advanced along the stud toward the frame, an engagement face engages a securing face.

14. The method of claim 9, wherein the distraction bolt is threadingly inserted through the through-passage.

15. The method of claim 9, wherein the distractor/compression instrument includes a friction reducer inserted into a hollow end portion of the distraction bolt.

16. The method of claim 9, wherein a rod passage is formed between the first leg and the second leg.

17. The method of claim 16, wherein the jaw has a first portion extending along a first side of the first leg and a second portion extending along an opposing side of the first leg, wherein the securing device advances the first portion and the second portion into the rod passage.

* * * * *